(12) United States Patent
Eilers

(10) Patent No.: US 7,322,810 B2
(45) Date of Patent: Jan. 29, 2008

(54) METHOD FOR IDENTIFYING COMPOUNDS THAT INHIBIT THE ACTIVITY OF MYC

(75) Inventor: Martin Eilers, Marburg-Cappel (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/128,572

(22) Filed: May 13, 2005

(65) Prior Publication Data

US 2005/0266513 A1     Dec. 1, 2005

(30) Foreign Application Priority Data

May 14, 2004   (EP) ................................. 04011505

(51) Int. Cl.
*C12Q 1/48*       (2006.01)

(52) U.S. Cl. ....................................................... 425/15

(58) Field of Classification Search .................... None
See application file for complete search history.

(56) References Cited

U.S. PATENT DOCUMENTS

| 6,087,122 A | 7/2000 | Hustad et al. |
| 2002/0042083 A1* | 4/2002 | Issakani et al. |
| 2002/0192160 A1 | 12/2002 | Callaghan et al. |

FOREIGN PATENT DOCUMENTS

WO    WO 03/012102 A2    2/2003

OTHER PUBLICATIONS

Gross-Mesilaty et al. Basal and Human Papillomavirus E6 Oncoprotein-Induced Degradation of Myc Proteins by the Ubiquitin Pathway; Proc. Natl. Acad. Sci. vol. 95 (1998) pp. 8058-8063.*

Jianping Jin et al. "A License to Kill: Transcritptional Activation and Enhanced Turnover of Myc by the SCFSkp2 Ubiquitin Ligase", Cancer Cell, 2003, vol. 3, No. 6, pp. 517-518 XP002298705.

So Young Kim et al., "Skp2 Regulates Myc Protein Stability and Activity", Molecular Cell, vol. 11, 2003, pp. 1177-1188 XP002298704.

Bruno Amati "Myc Degradation: Dancing with Ubiquitin Ligases", Proceedings of the National Academy of Sciences of the USA, vol. 101, No. 24, 2004, pp. 8843-8844 XP002298706.

Yi Sun "Targeting E3 Ubiquitin Ligases for Cancer Therapy", Cancer Biology & Therapy, vol. 2, No 6, 2003, pp. 623-629 XP009037246.

J.B. Almond, et al. "The Proteasome: a novel target for cancer chemotherapy", Leukemia, vol. 16, 2002, pp. 433-443 XP002298703.

Shlomit Gross-Mesilaty, et al. "Basal and human papillomavirus E6 oncoprotein-induced degradation of Myc proteins by the ubiquitin pathway", Proceedings from the National Academy of Sciences USA, vol. 95, pp. 8058-8063, 1998.

Adhikary S. et al.: "The ubiquitin ligase HectH9 regulates transcriptional activation by myc and is essential for tumor cell proliferation." CELL, vol. 123, Nov. 4, 2005, pp. 409-421, XP002365065.

* cited by examiner

*Primary Examiner*—Jon Weber
*Assistant Examiner*—Paul Martin
(74) *Attorney, Agent, or Firm*—Michael Morris; Mary-Ellen M. Devlin; David Dow

(57) ABSTRACT

Method for identifying compounds useful for the therapy of cancers in which the activity of Myc is causally involved. The method is based on measuring the activity of the E3 ligase HectH9, which is required for ubiquitination and activation of Myc.

9 Claims, 19 Drawing Sheets pSUPER pSUPER
HectH9

SEQUENCE LISTING

```
<160> NUMBER OF SEQ ID NOS: 2

<210> SEQ ID NO 1
<211> LENGTH: 13671
<212> TYPE: DNA
<213> ORGANISM: Homo sapiens
<220> FEATURE:
<221> NAME/KEY: CDS
<222> LOCATION: (1)..(13125)
<223> OTHER INFORMATION:

<400> SEQUENCE: 1 atg aaa gta gac agg act aaa ctg aag aag aca cct act gag gct cct        48
Met Lys Val Asp Arg Thr Lys Leu Lys Lys Thr Pro Thr Glu Ala Pro
1               5                   10                  15 gca gac tgc aga gcc tta ata gac aaa ctc aaa gtt tgt aat gat gag        96
Ala Asp Cys Arg Ala Leu Ile Asp Lys Leu Lys Val Cys Asn Asp Glu
                20                  25                  30 caa ctt ctc ttg gaa ctg cag cag atc aaa aca tgg aac att gga aag       144
Gln Leu Leu Leu Glu Leu Gln Gln Ile Lys Thr Trp Asn Ile Gly Lys
            35                  40                  45 tgc gag tta tat cac tgg gtg gac ctg ttg gac cgc ttc gat gga ata       192
Cys Glu Leu Tyr His Trp Val Asp Leu Leu Asp Arg Phe Asp Gly Ile
        50                  55                  60 ctg gca gat gct gga cag aca gtg gag aat atg tca tgg atg ctc gta       240
Leu Ala Asp Ala Gly Gln Thr Val Glu Asn Met Ser Trp Met Leu Val
65                  70                  75                  80 tgt gat agg cca gaa aga gag caa ctg aaa atg ctt ctc ttg gct gtg       288
Cys Asp Arg Pro Glu Arg Glu Gln Leu Lys Met Leu Leu Leu Ala Val
                85                  90                  95 ttg aac ttc aca gcc ttg ctc att gag tac agc ttt tcc cgg cat ctg       336
Leu Asn Phe Thr Ala Leu Leu Ile Glu Tyr Ser Phe Ser Arg His Leu
```

```
                 100                 105                 110
tac agt tcc ata gag cat ttg aca act tta ttg gct tcc tct gat atg      384
Tyr Ser Ile Glu His Leu Thr Thr Leu Leu Ala Ser Ser Asp Met
        115                 120                 125 caa gtg gtg ctg gca gtc ctc aat ctc cta tat gta ttt agc aaa aga      432
Gln Val Val Leu Ala Val Leu Asn Leu Leu Tyr Val Phe Ser Lys Arg
    130                 135                 140 tca aac tac atc act cgt ctg gga tct gac aag agg acc ccg ctg cta      480
Ser Asn Tyr Ile Thr Arg Leu Gly Ser Asp Lys Arg Thr Pro Leu Leu
145                 150                 155                 160 act cgg cta caa cat ttg gca gag agc tgg ggt gga aag gag aat ggc      528
Thr Arg Leu Gln His Leu Ala Glu Ser Trp Gly Gly Lys Glu Asn Gly
                165                 170                 175 ttt gga ctt gca gaa tgt tgc aga gac ttg cat atg atg aaa tat cca      576
Phe Gly Leu Ala Glu Cys Cys Arg Asp Leu His Met Met Lys Tyr Pro
        180                 185                 190 ccc agt gca act aca cta cac ttt gaa ttc tat gca gat cct ggg gcc      624
Pro Ser Ala Thr Thr Leu His Phe Glu Phe Tyr Ala Asp Pro Gly Ala
    195                 200                 205 gag gtc aaa att gag aaa agg aca act agt aac aca cta cat tat att      672
Glu Val Lys Ile Glu Lys Arg Thr Thr Ser Asn Thr Leu His Tyr Ile
210                 215                 220 cac ata gag caa ctt gac aag att tca gaa agc cct tct gaa atc atg      720
His Ile Glu Gln Leu Asp Lys Ile Ser Glu Ser Pro Ser Glu Ile Met
225                 230                 235                 240 gaa tct ctt acc aaa atg tac agc att cct aag gat aag cag atg ctg      768
Glu Ser Leu Thr Lys Met Tyr Ser Ile Pro Lys Asp Lys Gln Met Leu
                245                 250                 255 tta ttt aca cac ata cga ctg gcc cat ggc ttt tct aat cac agg aag      816
Leu Phe Thr His Ile Arg Leu Ala His Gly Phe Ser Asn His Arg Lys
        260                 265                 270 cga ttg cag gca gtt cag gcc aga ctg cat gca ata tct ata tta gtg      864
Arg Leu Gln Ala Val Gln Ala Arg Leu His Ala Ile Ser Ile Leu Val
    275                 280                 285 tat tcc aat gcc ttg cag gaa tca gca aac agt atc ttg tat aat ggc      912
Tyr Ser Asn Ala Leu Gln Glu Ser Ala Asn Ser Ile Leu Tyr Asn Gly
290                 295                 300 ttg ata gag gag ttg gta gat gtc ctt cag ata acg gat aag cag ctt      960
Leu Ile Glu Glu Leu Val Asp Val Leu Gln Ile Thr Asp Lys Gln Leu
305                 310                 315                 320 atg gag att aaa gca gct tct tta cga aca tta aca tca att gtc cac     1008
Met Glu Ile Lys Ala Ala Ser Leu Arg Thr Leu Thr Ser Ile Val His
                325                 330                 335 ttg gag aga act ccc aaa ctc agc agt att att gac tgt act gga act     1056
Leu Glu Arg Thr Pro Lys Leu Ser Ser Ile Ile Asp Cys Thr Gly Thr
        340                 345                 350 gcc tcc tac cat gga ttt ttg cca gtg ctt gta agg aac tgt atc cag     1104
Ala Ser Tyr His Gly Phe Leu Pro Val Leu Val Arg Asn Cys Ile Gln
    355                 360                 365 gcc atg att gat cct tcc atg gat cca tac cct cac cag ttt gcc act     1152
Ala Met Ile Asp Pro Ser Met Asp Pro Tyr Pro His Gln Phe Ala Thr
370                 375                 380 gct ctc ttc tct ttt tta tac cat ctg gcc agc tac gat gct ggt ggt     1200
Ala Leu Phe Ser Phe Leu Tyr His Leu Ala Ser Tyr Asp Ala Gly Gly
385                 390                 395                 400 gaa gcc ttg gtc tcc tgt gga atg atg gaa gcc tta ttg aag gtc ata     1248
Glu Ala Leu Val Ser Cys Gly Met Met Glu Ala Leu Leu Lys Val Ile
                405                 410                 415 aag ttt ctt ggc gat gaa cag gac cag ata aca ttt gtc acc aga gcc     1296
```

| | | |
|---|---|---|
| Lys Phe Leu Gly Asp Glu Gln Asp Gln Ile Thr Phe Val Thr Arg Ala<br>420                  425                430 | | |
| gtc aga gtg gtt gac ctt atc acc aac ctg gat atg gca gct ttt caa<br>Val Arg Val Val Asp Leu Ile Thr Asn Leu Asp Met Ala Ala Phe Gln<br>          435                440                445 | 1344 | |
| tcc cat agt gga ctt tct atc ttc att tat aga ctt gag cat gaa gta<br>Ser His Ser Gly Leu Ser Ile Phe Ile Tyr Arg Leu Glu His Glu Val<br>450                  455                460 | 1392 | |
| gat ttg tgc cga aaa gaa tgt ccg ttt gtg atc aag cca aag atc cag<br>Asp Leu Cys Arg Lys Glu Cys Pro Phe Val Ile Lys Pro Lys Ile Gln<br>465              470                475              480 | 1440 | |
| aga ccc aat act aca caa gaa gga gag gaa atg gaa act gat atg gat<br>Arg Pro Asn Thr Thr Gln Glu Gly Glu Glu Met Glu Thr Asp Met Asp<br>                      485                490              495 | 1488 | |
| gga gtc cag tgt att cca caa cga gca gca ctt ctg aaa tcc atg ttg<br>Gly Val Gln Cys Ile Pro Gln Arg Ala Ala Leu Leu Lys Ser Met Leu<br>                  500                505              510 | 1536 | |
| aat ttc ctc aag aag gcc atc caa gac cct gct ttc tca gat ggc ata<br>Asn Phe Leu Lys Lys Ala Ile Gln Asp Pro Ala Phe Ser Asp Gly Ile<br>          515                520                525 | 1584 | |
| cga cat gtg atg gat ggt tct ctg cct acc tcc ctg aaa cac atc atc<br>Arg His Val Met Asp Gly Ser Leu Pro Thr Ser Leu Lys His Ile Ile<br>530                  535                540 | 1632 | |
| agc aat gca gaa tac tat ggc cca tca ctc ttc ctc cta gct act gaa<br>Ser Asn Ala Glu Tyr Tyr Gly Pro Ser Leu Phe Leu Leu Ala Thr Glu<br>545                  550                555              560 | 1680 | |
| gtg gtg act gtg ttt gta ttt caa gaa cca tca ctg ctc tcc tca ctc<br>Val Val Thr Val Phe Val Phe Gln Glu Pro Ser Leu Leu Ser Ser Leu<br>                  565                570              575 | 1728 | |
| cag gac aat gga ttg aca gat gtc atg ctg cat gca ctg ctt atc aaa<br>Gln Asp Asn Gly Leu Thr Asp Val Met Leu His Ala Leu Leu Ile Lys<br>              580                585                590 | 1776 | |
| gat gtt cct gct acc cgt gaa gtc ctt ggc tcc ctc cca aat gta ttc<br>Asp Val Pro Ala Thr Arg Glu Val Leu Gly Ser Leu Pro Asn Val Phe<br>          595                600                605 | 1824 | |
| agt gca ctc tgt ttg aat gcc cga ggt ctt cag tct ttt gtt cag tgt<br>Ser Ala Leu Cys Leu Asn Ala Arg Gly Leu Gln Ser Phe Val Gln Cys<br>610                  615                620 | 1872 | |
| cag cct ttt gaa cgc ctc ttc aaa gtt ctt ctg tct cca gat tac ctc<br>Gln Pro Phe Glu Arg Leu Phe Lys Val Leu Leu Ser Pro Asp Tyr Leu<br>625                  630                635              640 | 1920 | |
| cca gcc atg cgg agg agg aga agt tct gat ccc ctt ggg gat act gca<br>Pro Ala Met Arg Arg Arg Arg Ser Ser Asp Pro Leu Gly Asp Thr Ala<br>                  645                650              655 | 1968 | |
| tcc aac ctg ggg agt gct gtc gat gag ctc atg aga cat cag ccc acc<br>Ser Asn Leu Gly Ser Ala Val Asp Glu Leu Met Arg His Gln Pro Thr<br>              660                665                670 | 2016 | |
| ctt aaa aca gat gca acg act gcc atc atc aag tta ctt gaa gaa atc<br>Leu Lys Thr Asp Ala Thr Thr Ala Ile Ile Lys Leu Leu Glu Glu Ile<br>          675                680                685 | 2064 | |
| tgt aat ctt gga agg gac ccc aaa tac atc tgt cag aag cca tca atc<br>Cys Asn Leu Gly Arg Asp Pro Lys Tyr Ile Cys Gln Lys Pro Ser Ile<br>690                  695                700 | 2112 | |
| cag aag gca gat ggc act gcc act gct cct ccc cca agg tct aat cat<br>Gln Lys Ala Asp Gly Thr Ala Thr Ala Pro Pro Pro Arg Ser Asn His<br>705                  710                715              720 | 2160 | |
| gcc gca gaa gaa gcc tct agt gag gat gag gag gaa gag gaa gta cag<br>Ala Ala Glu Glu Ala Ser Ser Glu Asp Glu Glu Glu Glu Glu Val Gln<br>                  725                730              735 | 2208 | |

```
gcc atg cag agc ttt aat tct acc cag caa aat gaa act gag cct aat    2256
Ala Met Gln Ser Phe Asn Ser Thr Gln Gln Asn Glu Thr Glu Pro Asn
        740                 745                 750 cag cag gtt gtt ggt aca gag gaa cgt att cct att ccc ctc atg gat    2304
Gln Gln Val Val Gly Thr Glu Glu Arg Ile Pro Ile Pro Leu Met Asp
            755                 760                 765 tac atc ctt aat gtg atg aaa ttt gtg gaa tct att ctg agc aac aat    2352
Tyr Ile Leu Asn Val Met Lys Phe Val Glu Ser Ile Leu Ser Asn Asn
770                 775                 780 aca aca gat gac cac tgc cag gaa ttt gtg aat cag aaa gga ctg ttg    2400
Thr Thr Asp Asp His Cys Gln Glu Phe Val Asn Gln Lys Gly Leu Leu
785                 790                 795                 800 cct ttg gtt acc att ttg ggt ctt ccc aat ctg ccc att gac ttt ccc    2448
Pro Leu Val Thr Ile Leu Gly Leu Pro Asn Leu Pro Ile Asp Phe Pro
                805                 810                 815 aca tct gct gcc tgt cag gct gtt gca ggt gtc tgc aaa tcc ata ttg    2496
Thr Ser Ala Ala Cys Gln Ala Val Ala Gly Val Cys Lys Ser Ile Leu
            820                 825                 830 aca ctg tca cat gaa ccc aaa gtc ctt caa gag ggt ctc ctt cag ttg    2544
Thr Leu Ser His Glu Pro Lys Val Leu Gln Glu Gly Leu Leu Gln Leu
        835                 840                 845 gac tcc atc ctc tcc tcc ctg gag ccc tta cac cgc ccc att gaa tcc    2592
Asp Ser Ile Leu Ser Ser Leu Glu Pro Leu His Arg Pro Ile Glu Ser
850                 855                 860 cct ggg ggc tca gtg ttg ttg cga gaa ctg gct tgc gca ggc aat gtt    2640
Pro Gly Gly Ser Val Leu Leu Arg Glu Leu Ala Cys Ala Gly Asn Val
865                 870                 875                 880 gct gat gct acc ctc tca gcc cag gcc aca cct ctg ctg cat gca ctc    2688
Ala Asp Ala Thr Leu Ser Ala Gln Ala Thr Pro Leu Leu His Ala Leu
                885                 890                 895 act gct gcc cat gcc tac atc atg atg ttt gtt cat act tgc aga gtt    2736
Thr Ala Ala His Ala Tyr Ile Met Met Phe Val His Thr Cys Arg Val
            900                 905                 910 gga cag agt gaa att cgt tcc atc tcc gta aac cag tgg ggc tct caa    2784
Gly Gln Ser Glu Ile Arg Ser Ile Ser Val Asn Gln Trp Gly Ser Gln
        915                 920                 925 ttg ggt ctg agt gtt ttg agc aag ctg agc cag tta tac tgt tcc ctg    2832
Leu Gly Leu Ser Val Leu Ser Lys Leu Ser Gln Leu Tyr Cys Ser Leu
930                 935                 940 gtg tgg gaa agc act gtc ctc ctc tct ctg tgt acc cca aac agc cta    2880
Val Trp Glu Ser Thr Val Leu Leu Ser Leu Cys Thr Pro Asn Ser Leu
945                 950                 955                 960 cca tct ggg tgt gaa ttt ggc cag gca gat atg cag aaa ctg gtt cca    2928
Pro Ser Gly Cys Glu Phe Gly Gln Ala Asp Met Gln Lys Leu Val Pro
                965                 970                 975 aag gat gag aag gca ggt acg acc cag ggc gga aaa aga tca gat ggg    2976
Lys Asp Glu Lys Ala Gly Thr Thr Gln Gly Gly Lys Arg Ser Asp Gly
            980                 985                 990 gaa cag gat gga gca gct gga agt  atg gat gct tct acc  cag ggc tta  3024
Glu Gln Asp Gly Ala Ala Gly Ser  Met Asp Ala Ser Thr  Gln Gly Leu
        995                 1000                1005 tta gaa  ggc att ggg cta gat  ggt gac aca ttg gct  ccc atg gag     3069
Leu Glu  Gly Ile Gly Leu Asp  Gly Asp Thr Leu Ala  Pro Met Glu
         1010                 1015                 1020 aca gat  gaa cct act gct tca  gac tct aag ggc aaa  tct aaa atc     3114
Thr Asp  Glu Pro Thr Ala Ser  Asp Ser Lys Gly Lys  Ser Lys Ile
         1025                 1030                 1035 aca cca  gca atg gct gcc aga  att aag caa atc aag  cct ttg tta     3159
Thr Pro  Ala Met Ala Ala Arg  Ile Lys Gln Ile Lys  Pro Leu Leu
         1040                 1045                 1050
```

-continued

| | | | | | | | | | | | | | | |
|---|---|---|---|---|---|---|---|---|---|---|---|---|---|---|
| tca | gct | tcc | tcc | aga | tta | ggc | cga | gca | ctt | gct | gag | cta | ttt | gga | 3204 |
| Ser | Ala | Ser | Ser | Arg | Leu | Gly | Arg | Ala | Leu | Ala | Glu | Leu | Phe | Gly | |
| 1055 | | | | | 1060 | | | | | 1065 | | | | | |
| ctt | ctt | gtt | aaa | ctt | tgt | gtg | gga | tct | cct | gtc | cgc | cag | aga | agg | 3249 |
| Leu | Leu | Val | Lys | Leu | Cys | Val | Gly | Ser | Pro | Val | Arg | Gln | Arg | Arg | |
| 1070 | | | | | 1075 | | | | | 1080 | | | | | |
| agc | cat | cat | gct | gcc | agc | acc | act | aca | gca | ccg | aca | cct | gcc | gcg | 3294 |
| Ser | His | His | Ala | Ala | Ser | Thr | Thr | Thr | Ala | Pro | Thr | Pro | Ala | Ala | |
| 1085 | | | | | 1090 | | | | | 1095 | | | | | |
| cga | tca | aca | gcc | tca | gct | ctc | act | aag | ctc | ttg | act | aag | ggg | tta | 3339 |
| Arg | Ser | Thr | Ala | Ser | Ala | Leu | Thr | Lys | Leu | Leu | Thr | Lys | Gly | Leu | |
| 1100 | | | | | 1105 | | | | | 1110 | | | | | |
| tct | tgg | cag | ccc | cca | cca | tat | aca | cct | act | ccc | cga | ttc | agg | ctg | 3384 |
| Ser | Trp | Gln | Pro | Pro | Pro | Tyr | Thr | Pro | Thr | Pro | Arg | Phe | Arg | Leu | |
| 1115 | | | | | 1120 | | | | | 1125 | | | | | |
| aca | ttc | ttc | atc | tgt | tca | gtt | ggt | ttc | aca | tcc | cca | atg | ctg | ttt | 3429 |
| Thr | Phe | Phe | Ile | Cys | Ser | Val | Gly | Phe | Thr | Ser | Pro | Met | Leu | Phe | |
| 1130 | | | | | 1135 | | | | | 1140 | | | | | |
| gat | gag | agg | aag | tat | ccc | tac | cac | ctc | atg | ctg | caa | aaa | ttt | ctc | 3474 |
| Asp | Glu | Arg | Lys | Tyr | Pro | Tyr | His | Leu | Met | Leu | Gln | Lys | Phe | Leu | |
| 1145 | | | | | 1150 | | | | | 1155 | | | | | |
| tgc | tcc | gga | ggc | cac | aat | gct | ctt | ttt | gaa | act | ttc | aac | tgg | gct | 3519 |
| Cys | Ser | Gly | Gly | His | Asn | Ala | Leu | Phe | Glu | Thr | Phe | Asn | Trp | Ala | |
| 1160 | | | | | 1165 | | | | | 1170 | | | | | |
| ctg | tcc | atg | gga | ggt | aaa | gtt | cct | gtt | tct | gag | gga | ttg | gaa | cac | 3564 |
| Leu | Ser | Met | Gly | Gly | Lys | Val | Pro | Val | Ser | Glu | Gly | Leu | Glu | His | |
| 1175 | | | | | 1180 | | | | | 1185 | | | | | |
| tca | gac | ttg | cct | gat | ggc | aca | gga | gaa | ttc | cta | gat | gcc | tgg | ctt | 3609 |
| Ser | Asp | Leu | Pro | Asp | Gly | Thr | Gly | Glu | Phe | Leu | Asp | Ala | Trp | Leu | |
| 1190 | | | | | 1195 | | | | | 1200 | | | | | |
| atg | ctg | gtg | gag | aag | atg | gtg | aat | ccc | acc | acg | gtg | ctt | gaa | tct | 3654 |
| Met | Leu | Val | Glu | Lys | Met | Val | Asn | Pro | Thr | Thr | Val | Leu | Glu | Ser | |
| 1205 | | | | | 1210 | | | | | 1215 | | | | | |
| cca | cat | tcg | ctg | cct | gcc | aaa | ttg | cct | gga | ggt | gtc | cag | aac | ttt | 3699 |
| Pro | His | Ser | Leu | Pro | Ala | Lys | Leu | Pro | Gly | Gly | Val | Gln | Asn | Phe | |
| 1220 | | | | | 1225 | | | | | 1230 | | | | | |
| ccc | cag | ttc | agt | gca | ctg | cgc | ttc | ctt | gtg | gta | act | cag | aaa | gca | 3744 |
| Pro | Gln | Phe | Ser | Ala | Leu | Arg | Phe | Leu | Val | Val | Thr | Gln | Lys | Ala | |
| 1235 | | | | | 1240 | | | | | 1245 | | | | | |
| gcc | ttt | act | tgc | atc | aaa | aac | tta | tgg | aac | cgg | aaa | ccc | ctg | aag | 3789 |
| Ala | Phe | Thr | Cys | Ile | Lys | Asn | Leu | Trp | Asn | Arg | Lys | Pro | Leu | Lys | |
| 1250 | | | | | 1255 | | | | | 1260 | | | | | |
| gta | tat | ggt | gga | cga | atg | gct | gaa | tcg | atg | ctg | gcc | att | cta | tgc | 3834 |
| Val | Tyr | Gly | Gly | Arg | Met | Ala | Glu | Ser | Met | Leu | Ala | Ile | Leu | Cys | |
| 1265 | | | | | 1270 | | | | | 1275 | | | | | |
| cac | atc | ctc | cga | gga | gaa | cct | gtg | att | cga | gag | aga | cta | agc | aag | 3879 |
| His | Ile | Leu | Arg | Gly | Glu | Pro | Val | Ile | Arg | Glu | Arg | Leu | Ser | Lys | |
| 1280 | | | | | 1285 | | | | | 1290 | | | | | |
| gag | aag | gag | ggg | tct | cga | gga | gaa | gag | gat | aca | ggg | caa | gag | gaa | 3924 |
| Glu | Lys | Glu | Gly | Ser | Arg | Gly | Glu | Glu | Asp | Thr | Gly | Gln | Glu | Glu | |
| 1295 | | | | | 1300 | | | | | 1305 | | | | | |
| ggt | ggc | tcc | cgc | cgg | gaa | cct | caa | gtc | aac | cag | caa | caa | ctg | caa | 3969 |
| Gly | Gly | Ser | Arg | Arg | Glu | Pro | Gln | Val | Asn | Gln | Gln | Gln | Leu | Gln | |
| 1310 | | | | | 1315 | | | | | 1320 | | | | | |
| cag | ctc | atg | gac | atg | ggc | ttc | aca | agg | gaa | cat | gca | atg | gag | gca | 4014 |
| Gln | Leu | Met | Asp | Met | Gly | Phe | Thr | Arg | Glu | His | Ala | Met | Glu | Ala | |
| 1325 | | | | | 1330 | | | | | 1335 | | | | | |
| ctg | ttg | aac | acc | agc | acc | atg | gag | cag | gcc | aca | gag | tac | ctt | tta | 4059 |
| Leu | Leu | Asn | Thr | Ser | Thr | Met | Glu | Gln | Ala | Thr | Glu | Tyr | Leu | Leu | |

-continued

|  |  |  |  |  |  |  |  |  |  |  |
|---|---|---|---|---|---|---|---|---|---|---|
|  | 1340 |  |  |  | 1345 |  |  |  | 1350 |  |

| acc<br>Thr | cac<br>His<br>1355 | cct<br>Pro | cct<br>Pro | cca<br>Pro | atc<br>Ile<br>1360 | atg<br>Met | gga<br>Gly | gga<br>Gly | gtt<br>Val | gtt<br>Val<br>1365 | cgg<br>Arg | gat<br>Asp | ctc<br>Leu | agc<br>Ser | 4104 |
|---|---|---|---|---|---|---|---|---|---|---|---|---|---|---|---|
| atg<br>Met | tct<br>Ser<br>1370 | gaa<br>Glu | gag<br>Glu | gac<br>Asp | cag<br>Gln<br>1375 | atg<br>Met | atg<br>Met | aga<br>Arg | gca<br>Ala | att<br>Ile<br>1380 | gct<br>Ala | atg<br>Met | tct<br>Ser | ctg<br>Leu | 4149 |
| gga<br>Gly | cag<br>Gln<br>1385 | gat<br>Asp | att<br>Ile | cca<br>Pro | atg<br>Met<br>1390 | gat<br>Asp | caa<br>Gln | agg<br>Arg | gca<br>Ala | gag<br>Glu<br>1395 | tca<br>Ser | cct<br>Pro | gag<br>Glu | gaa<br>Glu | 4194 |
| gtt<br>Val | gct<br>Ala<br>1400 | tgc<br>Cys | cgg<br>Arg | aag<br>Lys | gag<br>Glu<br>1405 | gaa<br>Glu | gag<br>Glu | gaa<br>Glu | cgg<br>Arg | aaa<br>Lys<br>1410 | gct<br>Ala | cgg<br>Arg | gaa<br>Glu | aag<br>Lys | 4239 |
| cag<br>Gln | gag<br>Glu<br>1415 | gag<br>Glu | gaa<br>Glu | gag<br>Glu | gct<br>Ala<br>1420 | aaa<br>Lys | tgt<br>Cys | cta<br>Leu | gag<br>Glu | aag<br>Lys<br>1425 | ttc<br>Phe | cag<br>Gln | gat<br>Asp | gct<br>Ala | 4284 |
| gac<br>Asp | ccg<br>Pro<br>1430 | ttg<br>Leu | gaa<br>Glu | caa<br>Gln | gat<br>Asp<br>1435 | gag<br>Glu | ctc<br>Leu | cac<br>His | act<br>Thr | ttc<br>Phe<br>1440 | aca<br>Thr | gat<br>Asp | act<br>Thr | atg<br>Met | 4329 |
| ttg<br>Leu | cca<br>Pro<br>1445 | ggc<br>Gly | tgc<br>Cys | ttc<br>Phe | cac<br>His<br>1450 | ctt<br>Leu | ctt<br>Leu | gat<br>Asp | gag<br>Glu | ctg<br>Leu<br>1455 | cca<br>Pro | gac<br>Asp | aca<br>Thr | gta<br>Val | 4374 |
| tac<br>Tyr | cgt<br>Arg<br>1460 | gtg<br>Val | tgt<br>Cys | gac<br>Asp | ctg<br>Leu<br>1465 | atc<br>Ile | atg<br>Met | aca<br>Thr | gca<br>Ala | atc<br>Ile<br>1470 | aaa<br>Lys | cgt<br>Arg | aat<br>Asn | gga<br>Gly | 4419 |
| gca<br>Ala | gat<br>Asp<br>1475 | tat<br>Tyr | cgt<br>Arg | gac<br>Asp | atg<br>Met<br>1480 | att<br>Ile | ctg<br>Leu | aag<br>Lys | caa<br>Gln | gta<br>Val<br>1485 | gtc<br>Val | aat<br>Asn | cag<br>Gln | gtg<br>Val | 4464 |
| tgg<br>Trp | gaa<br>Glu<br>1490 | gct<br>Ala | gct<br>Ala | gat<br>Asp | gta<br>Val<br>1495 | ttg<br>Leu | atc<br>Ile | aaa<br>Lys | gct<br>Ala | gct<br>Ala<br>1500 | ctt<br>Leu | ccc<br>Pro | ctg<br>Leu | aca<br>Thr | 4509 |
| aca<br>Thr | agt<br>Ser<br>1505 | gac<br>Asp | aca<br>Thr | aaa<br>Lys | acc<br>Thr<br>1510 | gtg<br>Val | tca<br>Ser | gag<br>Glu | tgg<br>Trp | ata<br>Ile<br>1515 | agt<br>Ser | cag<br>Gln | atg<br>Met | gcc<br>Ala | 4554 |
| aca<br>Thr | ctg<br>Leu<br>1520 | ccc<br>Pro | cag<br>Gln | gcc<br>Ala | tcc<br>Ser<br>1525 | aat<br>Asn | ttg<br>Leu | gct<br>Ala | act<br>Thr | aga<br>Arg<br>1530 | atc<br>Ile | ttg<br>Leu | ctt<br>Leu | tta<br>Leu | 4599 |
| acg<br>Thr | cta<br>Leu<br>1535 | ctt<br>Leu | ttt<br>Phe | gag<br>Glu | gag<br>Glu<br>1540 | ttg<br>Leu | aag<br>Lys | cta<br>Leu | cct<br>Pro | tgt<br>Cys<br>1545 | gct<br>Ala | tgg<br>Trp | gtg<br>Val | gtt<br>Val | 4644 |
| gaa<br>Glu | tca<br>Ser<br>1550 | agt<br>Ser | ggc<br>Gly | atc<br>Ile | ctt<br>Leu<br>1555 | aat<br>Asn | gtc<br>Val | cta<br>Leu | atc<br>Ile | aaa<br>Lys<br>1560 | ctc<br>Leu | ttg<br>Leu | gaa<br>Glu | gtg<br>Val | 4689 |
| gtt<br>Val | cag<br>Gln<br>1565 | ccc<br>Pro | tgc<br>Cys | ctc<br>Leu | cag<br>Gln<br>1570 | gca<br>Ala | gcc<br>Ala | aag<br>Lys | gag<br>Glu | cag<br>Gln<br>1575 | aag<br>Lys | gaa<br>Glu | gtc<br>Val | cag<br>Gln | 4734 |
| acc<br>Thr | cca<br>Pro<br>1580 | aag<br>Lys | tgg<br>Trp | atc<br>Ile | aca<br>Thr<br>1585 | cca<br>Pro | gtg<br>Val | ttg<br>Leu | ctc<br>Leu | ctg<br>Leu<br>1590 | att<br>Ile | gat<br>Asp | ttc<br>Phe | tat<br>Tyr | 4779 |
| gaa<br>Glu | aag<br>Lys<br>1595 | aca<br>Thr | gcc<br>Ala | atc<br>Ile | tcc<br>Ser<br>1600 | tca<br>Ser | aaa<br>Lys | agg<br>Arg | aga<br>Arg | gcc<br>Ala<br>1605 | cag<br>Gln | atg<br>Met | act<br>Thr | aag<br>Lys | 4824 |
| tac<br>Tyr | ctg<br>Leu<br>1610 | caa<br>Gln | tcc<br>Ser | aac<br>Asn | agc<br>Ser<br>1615 | aac<br>Asn | aac<br>Asn | tgg<br>Trp | cgc<br>Arg | tgg<br>Trp<br>1620 | ttt<br>Phe | gat<br>Asp | gat<br>Asp | cgc<br>Arg | 4869 |
| tct<br>Ser | ggg<br>Gly<br>1625 | cgt<br>Arg | tgg<br>Trp | tgt<br>Cys | agt<br>Ser<br>1630 | tac<br>Tyr | agt<br>Ser | gca<br>Ala | agc<br>Ser | aac<br>Asn<br>1635 | aat<br>Asn | agc<br>Ser | act<br>Thr | att<br>Ile | 4914 |
| gat<br>Asp | tct<br>Ser | gcc<br>Ala | tgg<br>Trp | aaa<br>Lys | tct<br>Ser | gga<br>Gly | gag<br>Glu | aca<br>Thr | agc<br>Ser | gtg<br>Val | cga<br>Arg | ttc<br>Phe | act<br>Thr | gca<br>Ala | 4959 |

|  |  |  |  |  |  |  |  |  |  |  |  |  |
|---|---|---|---|---|---|---|---|---|---|---|---|---|
| Asp | Ser | Ala | Trp | Lys | Ser | Gly | Glu | Thr | Ser | Val | Arg | Phe Thr Ala |
|  1640 |  |  |  |  | 1645 |  |  |  |  | 1650 |  |  |

```
ggc cga aga aga tac acg gtc caa ttc act aca atg gtg cag gtt    5004
Gly Arg Arg Arg Tyr Thr Val Gln Phe Thr Thr Met Val Gln Val
    1655                1660                1665 aat gag gaa aca ggg aac cga cgc cct gtg atg ctg act ctc ctc    5049
Asn Glu Glu Thr Gly Asn Arg Arg Pro Val Met Leu Thr Leu Leu
1670            1675                1680 agg gta cct cgg ctg aat aaa aat tca aaa aac agc aat gga cag    5094
Arg Val Pro Arg Leu Asn Lys Asn Ser Lys Asn Ser Asn Gly Gln
        1685                1690                1695 gaa cta gag aag acg ctg gaa gaa agc aaa gaa atg gat atc aaa    5139
Glu Leu Glu Lys Thr Leu Glu Glu Ser Lys Glu Met Asp Ile Lys
1700                1705                1710 cgt aaa gaa aat aaa ggc aat gat acc cct ttg gcc cta gag agt    5184
Arg Lys Glu Asn Lys Gly Asn Asp Thr Pro Leu Ala Leu Glu Ser
    1715                1720                1725 aca aac act gaa aag gag aca agc ctg gag gaa aca aaa atc ggg    5229
Thr Asn Thr Glu Lys Glu Thr Ser Leu Glu Glu Thr Lys Ile Gly
        1730                1735                1740 gag atc ctg atc cag ggc ttg aca gaa gat atg gtg act gtt tta    5274
Glu Ile Leu Ile Gln Gly Leu Thr Glu Asp Met Val Thr Val Leu
1745                1750                1755 atc cgg gcc tgc gtg agc atg ctg gga gtc cct gtg gac cca gat    5319
Ile Arg Ala Cys Val Ser Met Leu Gly Val Pro Val Asp Pro Asp
    1760                1765                1770 act ttg cat gcc acc ctt cgt ctc tgt ctg agg ctc acc cgg gac    5364
Thr Leu His Ala Thr Leu Arg Leu Cys Leu Arg Leu Thr Arg Asp
        1775                1780                1785 cac aaa tat gcc atg atg ttt gca gaa ctg aag agt acc cgc atg    5409
His Lys Tyr Ala Met Met Phe Ala Glu Leu Lys Ser Thr Arg Met
1790                1795                1800 atc ttg aat ttg acc cag agc tca ggc ttc aat ggg ttt act ccc    5454
Ile Leu Asn Leu Thr Gln Ser Ser Gly Phe Asn Gly Phe Thr Pro
    1805                1810                1815 ctg gtc acc ctt ctc tta aga cac atc att gag gac ccc tgt acc    5499
Leu Val Thr Leu Leu Leu Arg His Ile Ile Glu Asp Pro Cys Thr
        1820                1825                1830 ctt cgt cat acc atg gaa aag gtt gtt cgc tca gca gct aca agt    5544
Leu Arg His Thr Met Glu Lys Val Val Arg Ser Ala Ala Thr Ser
1835                1840                1845 gga gct ggt agc act acc tct ggt gtt gtg tct ggc agc ctc ggc    5589
Gly Ala Gly Ser Thr Thr Ser Gly Val Val Ser Gly Ser Leu Gly
    1850                1855                1860 tct cgg gag atc aac tac atc ctt cgt gtc ctt ggg cca gcc gca    5634
Ser Arg Glu Ile Asn Tyr Ile Leu Arg Val Leu Gly Pro Ala Ala
        1865                1870                1875 tgc cgc aat cca gac ata ttc aca gaa gtg gcc aac tgc tgt atc    5679
Cys Arg Asn Pro Asp Ile Phe Thr Glu Val Ala Asn Cys Cys Ile
1880                1885                1890 cgc atc gcc ctt cct gcc cct cga ggc tca gga act gct tca gat    5724
Arg Ile Ala Leu Pro Ala Pro Arg Gly Ser Gly Thr Ala Ser Asp
    1895                1900                1905 gat gaa ttt gag aat ctt aga att aaa ggc cct aat gct gta cag    5769
Asp Glu Phe Glu Asn Leu Arg Ile Lys Gly Pro Asn Ala Val Gln
        1910                1915                1920 ctg gtg aag acc acc cct ttg aag ccc tca cct ctg cct gtc atc    5814
Leu Val Lys Thr Thr Pro Leu Lys Pro Ser Pro Leu Pro Val Ile
1925                1930                1935
```

-continued

| | | |
|---|---|---|
| cct gat act atc aag gaa gtg atc tat gat atg ctg aat gct ctg<br>Pro Asp Thr Ile Lys Glu Val Ile Tyr Asp Met Leu Asn Ala Leu<br>1940                    1945                    1950 | 5859 |
| gct gca tac cat gct cca gag gaa gca gat aaa tct gat cct aaa<br>Ala Ala Tyr His Ala Pro Glu Glu Ala Asp Lys Ser Asp Pro Lys<br>1955                    1960                    1965 | 5904 |
| cct ggg gtt atg acc caa gag gtt ggc cag ctc ctg caa gac atg<br>Pro Gly Val Met Thr Gln Glu Val Gly Gln Leu Leu Gln Asp Met<br>1970                    1975                    1980 | 5949 |
| ggt gat gat gta tac cag cag tac cgg tca ctt acg cgt cag agc<br>Gly Asp Asp Val Tyr Gln Gln Tyr Arg Ser Leu Thr Arg Gln Ser<br>1985                    1990                    1995 | 5994 |
| agt gac ttt gat acg cag tca ggt ttt tcc att aat agt cag gtc<br>Ser Asp Phe Asp Thr Gln Ser Gly Phe Ser Ile Asn Ser Gln Val<br>2000                    2005                    2010 | 6039 |
| ttt gct gca gat ggt gcc tcc act gag act tcc gca tct ggg acc<br>Phe Ala Ala Asp Gly Ala Ser Thr Glu Thr Ser Ala Ser Gly Thr<br>2015                    2020                    2025 | 6084 |
| tcc caa gga gag gct tca act cca gag gag tct cga gat ggg aag<br>Ser Gln Gly Glu Ala Ser Thr Pro Glu Glu Ser Arg Asp Gly Lys<br>2030                    2035                    2040 | 6129 |
| aaa gat aaa gaa ggg gac cgg gcc tct gag gaa ggc aaa cag aaa<br>Lys Asp Lys Glu Gly Asp Arg Ala Ser Glu Glu Gly Lys Gln Lys<br>2045                    2050                    2055 | 6174 |
| ggc aag ggc agc aaa cct tta atg cct acc tcc act atc ctt cgt<br>Gly Lys Gly Ser Lys Pro Leu Met Pro Thr Ser Thr Ile Leu Arg<br>2060                    2065                    2070 | 6219 |
| ctt ctg gca gag ttg gtg agg tcc tat gtt ggt att gct acc ctg<br>Leu Leu Ala Glu Leu Val Arg Ser Tyr Val Gly Ile Ala Thr Leu<br>2075                    2080                    2085 | 6264 |
| att gcc aac tac agc tac act gtg ggc cag tct gaa ctg atc aaa<br>Ile Ala Asn Tyr Ser Tyr Thr Val Gly Gln Ser Glu Leu Ile Lys<br>2090                    2095                    2100 | 6309 |
| gag gac tgc agt gtg cta gct ttt gtt ctg gac cac ctg ctc cca<br>Glu Asp Cys Ser Val Leu Ala Phe Val Leu Asp His Leu Leu Pro<br>2105                    2110                    2115 | 6354 |
| cat acc cag aat gca gaa gac aag gac acc cct gcc ttg gcc cgc<br>His Thr Gln Asn Ala Glu Asp Lys Asp Thr Pro Ala Leu Ala Arg<br>2120                    2125                    2130 | 6399 |
| ctg ttc ctc gca agc ctg gct gct gca ggg agt ggc aca gat gcc<br>Leu Phe Leu Ala Ser Leu Ala Ala Ala Gly Ser Gly Thr Asp Ala<br>2135                    2140                    2145 | 6444 |
| cag gtg gcc cta gtg aat gaa gta aaa gca gcc ctt gga cgg gca<br>Gln Val Ala Leu Val Asn Glu Val Lys Ala Ala Leu Gly Arg Ala<br>2150                    2155                    2160 | 6489 |
| ctg gct atg gct gag agt aca gag aaa cat gcc agg ctt cag gca<br>Leu Ala Met Ala Glu Ser Thr Glu Lys His Ala Arg Leu Gln Ala<br>2165                    2170                    2175 | 6534 |
| gtg atg tgt atc atc agt act atc atg gag tcc tgc ccc tcc acc<br>Val Met Cys Ile Ile Ser Thr Ile Met Glu Ser Cys Pro Ser Thr<br>2180                    2185                    2190 | 6579 |
| tcc agc ttc tac agc agt gcc aca gcg aag acc cag cac aat ggc<br>Ser Ser Phe Tyr Ser Ser Ala Thr Ala Lys Thr Gln His Asn Gly<br>2195                    2200                    2205 | 6624 |
| atg aac aac atc att cgg ctt ttc ctg aag aag gga ctg gtt aat<br>Met Asn Asn Ile Ile Arg Leu Phe Leu Lys Lys Gly Leu Val Asn<br>2210                    2215                    2220 | 6669 |
| gac ctg gcc aga gta cct cac agc tta gac ctg tcc agt ccc aac<br>Asp Leu Ala Arg Val Pro His Ser Leu Asp Leu Ser Ser Pro Asn<br>2225                    2230                    2235 | 6714 |

-continued

| | |
|---|---|
| atg gcc aac aca gtc aat gct gct ctg aag cct ttg gaa aca ctt<br>Met Ala Asn Thr Val Asn Ala Ala Leu Lys Pro Leu Glu Thr Leu<br>2240                 2245                            2250 | 6759 |
| tcc cgg att gtg aac cag ccc agt agc ctt ttt ggc agc aag agt<br>Ser Arg Ile Val Asn Gln Pro Ser Ser Leu Phe Gly Ser Lys Ser<br>2255                 2260                            2265 | 6804 |
| gct tct agc aag aac aag tct gag cag gat gcc caa gga gcc tct<br>Ala Ser Ser Lys Asn Lys Ser Glu Gln Asp Ala Gln Gly Ala Ser<br>2270                 2275                            2280 | 6849 |
| caa gat tcc agt agc aac cag cag gac cca ggc gag cct ggg gaa<br>Gln Asp Ser Ser Ser Asn Gln Gln Asp Pro Gly Glu Pro Gly Glu<br>2285                 2290                            2295 | 6894 |
| gca gaa gtg cag gag gag gat cat gat gtc act cag aca gag gtg<br>Ala Glu Val Gln Glu Glu Asp His Asp Val Thr Gln Thr Glu Val<br>2300                 2305                            2310 | 6939 |
| gca gat ggg gat atc atg gat ggg gag gct gaa acc gac tca gtg<br>Ala Asp Gly Asp Ile Met Asp Gly Glu Ala Glu Thr Asp Ser Val<br>2315                 2320                            2325 | 6984 |
| gtg att gct ggg cag cct gag gtg ctc agt tca caa gag atg cag<br>Val Ile Ala Gly Gln Pro Glu Val Leu Ser Ser Gln Glu Met Gln<br>2330                 2335                            2340 | 7029 |
| gtt gag aat gag ctg gag gac ctg ata gat gag ttg ctt gag agg<br>Val Glu Asn Glu Leu Glu Asp Leu Ile Asp Glu Leu Leu Glu Arg<br>2345                 2350                            2355 | 7074 |
| gat ggc gga tct ggg aac agt aca att ata gtg agc aga agt gga<br>Asp Gly Gly Ser Gly Asn Ser Thr Ile Ile Val Ser Arg Ser Gly<br>2360                 2365                            2370 | 7119 |
| gag gat gaa tca caa gag gac gtg ctg atg gat gaa gct cct tcc<br>Glu Asp Glu Ser Gln Glu Asp Val Leu Met Asp Glu Ala Pro Ser<br>2375                 2380                            2385 | 7164 |
| aac ctc agc caa gct tcc acc ttg cag gcc aac cga gaa gat tcc<br>Asn Leu Ser Gln Ala Ser Thr Leu Gln Ala Asn Arg Glu Asp Ser<br>2390                 2395                            2400 | 7209 |
| atg aat atc ctg gac cct gag gat gag gag gag cac act cag gaa<br>Met Asn Ile Leu Asp Pro Glu Asp Glu Glu Glu His Thr Gln Glu<br>2405                 2410                            2415 | 7254 |
| gag gac agc agt ggc agt aac gag gat gag gat gat agt cag gat<br>Glu Asp Ser Ser Gly Ser Asn Glu Asp Glu Asp Asp Ser Gln Asp<br>2420                 2425                            2430 | 7299 |
| gaa gag gag gag gag gag gaa gat gag gaa gat gat cag gag gat<br>Glu Glu Glu Glu Glu Glu Glu Asp Glu Glu Asp Asp Gln Glu Asp<br>2435                 2440                            2445 | 7344 |
| gat gaa ggt gaa gag gga gat gaa gac gat gac gac gat ggc tct<br>Asp Glu Gly Glu Glu Gly Asp Glu Asp Asp Asp Asp Gly Ser<br>2450                 2455                            2460 | 7389 |
| gag atg gaa ttg gat gag gat tat cct gat atg aac gct tct ccc<br>Glu Met Glu Leu Asp Glu Asp Tyr Pro Asp Met Asn Ala Ser Pro<br>2465                 2470                            2475 | 7434 |
| ttg gtc cga ttt gag cgc ttt gac cgg gag gat gat ctc atc att<br>Leu Val Arg Phe Glu Arg Phe Asp Arg Glu Asp Asp Leu Ile Ile<br>2480                 2485                            2490 | 7479 |
| gag ttt gac aac atg ttc tcc agt gct aca gac atc ccc cca tcc<br>Glu Phe Asp Asn Met Phe Ser Ser Ala Thr Asp Ile Pro Pro Ser<br>2495                 2500                            2505 | 7524 |
| cca gga aat atc cct acc acc cat cca ctg atg gtg cgc cat gca<br>Pro Gly Asn Ile Pro Thr Thr His Pro Leu Met Val Arg His Ala<br>2510                 2515                            2520 | 7569 |
| gac cac agt tct ctg aca ctg ggc agt ggc tct tca aca act cgt<br>Asp His Ser Ser Leu Thr Leu Gly Ser Gly Ser Ser Thr Thr Arg | 7614 |

-continued

| | | | | | | | | | | |
|---|---|---|---|---|---|---|---|---|---|---|
| | | 2525 | | | 2530 | | | | 2535 | |
| ctc | acc | cag | ggc | atc | ggg | cgc | agt | cag | agg | acc | cta | agg | cag | ctg | 7659 |
| Leu | Thr | Gln | Gly | Ile | Gly | Arg | Ser | Gln | Arg | Thr | Leu | Arg | Gln | Leu | |
| | 2540 | | | | 2545 | | | | | 2550 | | | | | |

| acg | gcc | aat | act | ggc | cac | acc | att | cat | gtt | cac | tac | cct | ggg | aat | 7704 |
|---|---|---|---|---|---|---|---|---|---|---|---|---|---|---|---|
| Thr | Ala | Asn | Thr | Gly | His | Thr | Ile | His | Val | His | Tyr | Pro | Gly | Asn | |
| 2555 | | | | | 2560 | | | | | 2565 | | | | | |

| cgc | cag | ccc | aac | cct | cct | ctt | ata | ctg | cag | agg | ttg | ctt | ggt | ccc | 7749 |
|---|---|---|---|---|---|---|---|---|---|---|---|---|---|---|---|
| Arg | Gln | Pro | Asn | Pro | Pro | Leu | Ile | Leu | Gln | Arg | Leu | Leu | Gly | Pro | |
| 2570 | | | | | 2575 | | | | | 2580 | | | | | |

| tca | gct | gct | gct | gac | atc | ctt | cag | ctg | agc | agc | agc | ctt | ccc | cta | 7794 |
|---|---|---|---|---|---|---|---|---|---|---|---|---|---|---|---|
| Ser | Ala | Ala | Ala | Asp | Ile | Leu | Gln | Leu | Ser | Ser | Ser | Leu | Pro | Leu | |
| 2585 | | | | | 2590 | | | | | 2595 | | | | | |

| caa | agc | cgg | ggt | cgg | gcc | cgc | ctc | ctg | gta | ggc | aac | gat | gac | gtc | 7839 |
|---|---|---|---|---|---|---|---|---|---|---|---|---|---|---|---|
| Gln | Ser | Arg | Gly | Arg | Ala | Arg | Leu | Leu | Val | Gly | Asn | Asp | Asp | Val | |
| 2600 | | | | | 2605 | | | | | 2610 | | | | | |

| cac | atc | atc | gcc | cgt | tct | gat | gat | gag | ctg | ctg | gat | gac | ttt | ttc | 7884 |
|---|---|---|---|---|---|---|---|---|---|---|---|---|---|---|---|
| His | Ile | Ile | Ala | Arg | Ser | Asp | Asp | Glu | Leu | Leu | Asp | Asp | Phe | Phe | |
| 2615 | | | | | 2620 | | | | | 2625 | | | | | |

| cat | gat | cag | agc | aca | gct | acc | agc | caa | gca | gga | acc | ctg | tcc | agc | 7929 |
|---|---|---|---|---|---|---|---|---|---|---|---|---|---|---|---|
| His | Asp | Gln | Ser | Thr | Ala | Thr | Ser | Gln | Ala | Gly | Thr | Leu | Ser | Ser | |
| 2630 | | | | | 2635 | | | | | 2640 | | | | | |

| atc | ccc | aca | gcc | ctg | acc | cgc | tgg | aca | gaa | gaa | tgc | aaa | gtt | ctc | 7974 |
|---|---|---|---|---|---|---|---|---|---|---|---|---|---|---|---|
| Ile | Pro | Thr | Ala | Leu | Thr | Arg | Trp | Thr | Glu | Glu | Cys | Lys | Val | Leu | |
| 2645 | | | | | 2650 | | | | | 2655 | | | | | |

| gat | gct | gag | agc | atg | cat | gac | tgt | gtt | tca | gtg | gtt | aaa | gtg | tcc | 8019 |
|---|---|---|---|---|---|---|---|---|---|---|---|---|---|---|---|
| Asp | Ala | Glu | Ser | Met | His | Asp | Cys | Val | Ser | Val | Val | Lys | Val | Ser | |
| 2660 | | | | | 2665 | | | | | 2670 | | | | | |

| att | gtc | aat | cac | ctg | gaa | ttc | ctg | agg | gat | gag | gag | ctg | gaa | gaa | 8064 |
|---|---|---|---|---|---|---|---|---|---|---|---|---|---|---|---|
| Ile | Val | Asn | His | Leu | Glu | Phe | Leu | Arg | Asp | Glu | Glu | Leu | Glu | Glu | |
| 2675 | | | | | 2680 | | | | | 2685 | | | | | |

| agg | cga | gag | aag | cgc | agg | aaa | caa | ctg | gct | gag | gaa | gaa | aca | aag | 8109 |
|---|---|---|---|---|---|---|---|---|---|---|---|---|---|---|---|
| Arg | Arg | Glu | Lys | Arg | Arg | Lys | Gln | Leu | Ala | Glu | Glu | Glu | Thr | Lys | |
| 2690 | | | | | 2695 | | | | | 2700 | | | | | |

| ata | act | gat | aaa | ggc | aaa | gaa | gat | aag | gag | aac | agg | gat | cag | agt | 8154 |
|---|---|---|---|---|---|---|---|---|---|---|---|---|---|---|---|
| Ile | Thr | Asp | Lys | Gly | Lys | Glu | Asp | Lys | Glu | Asn | Arg | Asp | Gln | Ser | |
| 2705 | | | | | 2710 | | | | | 2715 | | | | | |

| gca | cag | tgt | act | gca | tct | aag | tca | aat | gac | tcc | act | gaa | cag | aat | 8199 |
|---|---|---|---|---|---|---|---|---|---|---|---|---|---|---|---|
| Ala | Gln | Cys | Thr | Ala | Ser | Lys | Ser | Asn | Asp | Ser | Thr | Glu | Gln | Asn | |
| 2720 | | | | | 2725 | | | | | 2730 | | | | | |

| ctc | tca | gat | ggg | acg | cct | atg | cct | gac | agc | tac | cca | aca | acc | cca | 8244 |
|---|---|---|---|---|---|---|---|---|---|---|---|---|---|---|---|
| Leu | Ser | Asp | Gly | Thr | Pro | Met | Pro | Asp | Ser | Tyr | Pro | Thr | Thr | Pro | |
| 2735 | | | | | 2740 | | | | | 2745 | | | | | |

| tct | tca | act | gat | gca | gct | aca | tct | gag | tcc | aag | gag | acc | ctt | ggc | 8289 |
|---|---|---|---|---|---|---|---|---|---|---|---|---|---|---|---|
| Ser | Ser | Thr | Asp | Ala | Ala | Thr | Ser | Glu | Ser | Lys | Glu | Thr | Leu | Gly | |
| 2750 | | | | | 2755 | | | | | 2760 | | | | | |

| act | ctg | caa | tcc | tca | caa | cag | caa | cca | aca | ctc | cca | acc | cca | cca | 8334 |
|---|---|---|---|---|---|---|---|---|---|---|---|---|---|---|---|
| Thr | Leu | Gln | Ser | Ser | Gln | Gln | Gln | Pro | Thr | Leu | Pro | Thr | Pro | Pro | |
| 2765 | | | | | 2770 | | | | | 2775 | | | | | |

| gct | ttg | gga | gag | gtt | cct | cag | gag | ctg | cag | tct | cca | gct | gga | gaa | 8379 |
|---|---|---|---|---|---|---|---|---|---|---|---|---|---|---|---|
| Ala | Leu | Gly | Glu | Val | Pro | Gln | Glu | Leu | Gln | Ser | Pro | Ala | Gly | Glu | |
| 2780 | | | | | 2785 | | | | | 2790 | | | | | |

| ggg | ggc | agc | tct | aca | cag | cta | ttg | atg | cct | gta | gag | cca | gag | gaa | 8424 |
|---|---|---|---|---|---|---|---|---|---|---|---|---|---|---|---|
| Gly | Gly | Ser | Ser | Thr | Gln | Leu | Leu | Met | Pro | Val | Glu | Pro | Glu | Glu | |
| 2795 | | | | | 2800 | | | | | 2805 | | | | | |

| ttg | ggt | ccc | aca | agg | cca | agt | ggg | gaa | gca | gaa | aca | act | cag | atg | 8469 |
|---|---|---|---|---|---|---|---|---|---|---|---|---|---|---|---|
| Leu | Gly | Pro | Thr | Arg | Pro | Ser | Gly | Glu | Ala | Glu | Thr | Thr | Gln | Met | |
| 2810 | | | | | 2815 | | | | | 2820 | | | | | |

| gag | tta | tcc | cca | gct | ccc | act | ata | acc | tca | ctt | tcc | cca | gag | aga | 8514 |
|---|---|---|---|---|---|---|---|---|---|---|---|---|---|---|---|

-continued

| | | | | | | | | | | | |
|---|---|---|---|---|---|---|---|---|---|---|---|
| Glu | Leu | Ser | Pro | Ala | Pro | Thr | Ile | Thr | Ser | Leu | Ser | Pro | Glu | Arg | |
| | 2825 | | | | 2830 | | | | 2835 | | |

| gct | gag | gat | tct | gat | gca | ctg | acg | gct | gtc | agc | agt | cag | cta | gaa | 8559 |
| Ala | Glu | Asp | Ser | Asp | Ala | Leu | Thr | Ala | Val | Ser | Ser | Gln | Leu | Glu | |
| | 2840 | | | | 2845 | | | | 2850 | | |

| ggc | tct | cct | atg | gat | aca | agc | agc | ctg | gct | tcc | tgt | acc | tta | gag | 8604 |
| Gly | Ser | Pro | Met | Asp | Thr | Ser | Ser | Leu | Ala | Ser | Cys | Thr | Leu | Glu | |
| | 2855 | | | | 2860 | | | | 2865 | | |

| gag | gct | gtg | ggt | gac | act | tca | gca | gct | ggc | agt | tct | gag | cag | ccc | 8649 |
| Glu | Ala | Val | Gly | Asp | Thr | Ser | Ala | Ala | Gly | Ser | Ser | Glu | Gln | Pro | |
| | 2870 | | | | 2875 | | | | 2880 | | |

| aga | gca | ggc | agc | tcc | act | cct | ggg | gat | gcc | cca | cca | gct | gtg | gcg | 8694 |
| Arg | Ala | Gly | Ser | Ser | Thr | Pro | Gly | Asp | Ala | Pro | Pro | Ala | Val | Ala | |
| | 2885 | | | | 2890 | | | | 2895 | | |

| gaa | gtg | caa | ggc | agg | agt | gat | ggg | tca | ggg | gaa | tct | gcc | cag | cca | 8739 |
| Glu | Val | Gln | Gly | Arg | Ser | Asp | Gly | Ser | Gly | Glu | Ser | Ala | Gln | Pro | |
| | 2900 | | | | 2905 | | | | 2910 | | |

| cct | gag | gac | agc | tcc | cca | cct | gca | tcc | tct | gag | agc | tct | tcc | acc | 8784 |
| Pro | Glu | Asp | Ser | Ser | Pro | Pro | Ala | Ser | Ser | Glu | Ser | Ser | Ser | Thr | |
| | 2915 | | | | 2920 | | | | 2925 | | |

| aga | gat | tct | gcc | gtg | gcc | att | tct | gga | gca | gat | tcc | cga | gga | atc | 8829 |
| Arg | Asp | Ser | Ala | Val | Ala | Ile | Ser | Gly | Ala | Asp | Ser | Arg | Gly | Ile | |
| | 2930 | | | | 2935 | | | | 2940 | | |

| cta | gaa | gag | ccg | ttg | cct | tca | aca | agc | agt | gaa | gaa | gaa | gat | ccc | 8874 |
| Leu | Glu | Glu | Pro | Leu | Pro | Ser | Thr | Ser | Ser | Glu | Glu | Glu | Asp | Pro | |
| | 2945 | | | | 2950 | | | | 2955 | | |

| ctt | gcg | ggt | atc | agt | ctc | cct | gaa | ggt | gtg | gac | ccc | tct | ttt | ctg | 8919 |
| Leu | Ala | Gly | Ile | Ser | Leu | Pro | Glu | Gly | Val | Asp | Pro | Ser | Phe | Leu | |
| | 2960 | | | | 2965 | | | | 2970 | | |

| gct | gcc | ctg | cct | gat | gac | atc | cgt | cgg | gaa | gtt | cta | cag | aac | cag | 8964 |
| Ala | Ala | Leu | Pro | Asp | Asp | Ile | Arg | Arg | Glu | Val | Leu | Gln | Asn | Gln | |
| | 2975 | | | | 2980 | | | | 2985 | | |

| cta | ggc | att | cgt | cca | cca | acc | cgg | act | gcc | ccc | tcc | aca | aat | agc | 9009 |
| Leu | Gly | Ile | Arg | Pro | Pro | Thr | Arg | Thr | Ala | Pro | Ser | Thr | Asn | Ser | |
| | 2990 | | | | 2995 | | | | 3000 | | |

| tca | gcg | cct | gca | gtg | gtg | ggg | aat | cct | ggt | gtg | act | gaa | gtg | agc | 9054 |
| Ser | Ala | Pro | Ala | Val | Val | Gly | Asn | Pro | Gly | Val | Thr | Glu | Val | Ser | |
| | 3005 | | | | 3010 | | | | 3015 | | |

| cct | gag | ttt | ctg | gct | gcc | ctg | cct | cca | gcc | att | cag | gag | gaa | gta | 9099 |
| Pro | Glu | Phe | Leu | Ala | Ala | Leu | Pro | Pro | Ala | Ile | Gln | Glu | Glu | Val | |
| | 3020 | | | | 3025 | | | | 3030 | | |

| ctg | gca | cag | cag | aga | gct | gag | cag | cag | cga | cga | gaa | cta | gca | cag | 9144 |
| Leu | Ala | Gln | Gln | Arg | Ala | Glu | Gln | Gln | Arg | Arg | Glu | Leu | Ala | Gln | |
| | 3035 | | | | 3040 | | | | 3045 | | |

| aat | gcc | agc | tca | gac | acc | cct | atg | gac | cct | gtg | acc | ttc | atc | cag | 9189 |
| Asn | Ala | Ser | Ser | Asp | Thr | Pro | Met | Asp | Pro | Val | Thr | Phe | Ile | Gln | |
| | 3050 | | | | 3055 | | | | 3060 | | |

| act | ctg | ccc | tca | gac | ctg | cgc | cgt | agt | gtc | cta | gag | gat | atg | gag | 9234 |
| Thr | Leu | Pro | Ser | Asp | Leu | Arg | Arg | Ser | Val | Leu | Glu | Asp | Met | Glu | |
| | 3065 | | | | 3070 | | | | 3075 | | |

| gac | agt | gtg | tta | gct | gtg | atg | cca | cct | gac | att | gca | gct | gag | gct | 9279 |
| Asp | Ser | Val | Leu | Ala | Val | Met | Pro | Pro | Asp | Ile | Ala | Ala | Glu | Ala | |
| | 3080 | | | | 3085 | | | | 3090 | | |

| caa | gcc | ctg | aga | cga | gag | caa | gaa | gcc | cgg | cag | cga | cag | ctc | atg | 9324 |
| Gln | Ala | Leu | Arg | Arg | Glu | Gln | Glu | Ala | Arg | Gln | Arg | Gln | Leu | Met | |
| | 3095 | | | | 3100 | | | | 3105 | | |

| cat | gag | cgt | ctg | ttt | ggg | cac | agt | agc | acc | tcc | gca | ctc | tct | gct | 9369 |
| His | Glu | Arg | Leu | Phe | Gly | His | Ser | Ser | Thr | Ser | Ala | Leu | Ser | Ala | |
| | 3110 | | | | 3115 | | | | 3120 | | |

| | |
|---|---|
| att ctc cga agc ccg gct ttc acc agt cgc tta agt ggc aac cgt<br>Ile Leu Arg Ser Pro Ala Phe Thr Ser Arg Leu Ser Gly Asn Arg<br>3125                            3130                            3135 | 9414 |
| ggg gtc cag tat act cgc ctt gct gtg cag aga ggt ggc acc ttc<br>Gly Val Gln Tyr Thr Arg Leu Ala Val Gln Arg Gly Gly Thr Phe<br>3140                            3145                            3150 | 9459 |
| cag atg ggg ggt agc agc agc cat aac agg cct tct ggc agt aat<br>Gln Met Gly Gly Ser Ser Ser His Asn Arg Pro Ser Gly Ser Asn<br>3155                            3160                            3165 | 9504 |
| gta gat act ctc ctc cgc ctc cga gga cgg ctc ctt ctg gac cac<br>Val Asp Thr Leu Leu Arg Leu Arg Gly Arg Leu Leu Leu Asp His<br>3170                            3175                            3180 | 9549 |
| gaa gcc ctt tct tgt ctc ttg gtc cta ctt ttt gtg gat gag cca<br>Glu Ala Leu Ser Cys Leu Leu Val Leu Leu Phe Val Asp Glu Pro<br>3185                            3190                            3195 | 9594 |
| aag ctc aat act agc cgt cta cac cga gta ctg aga aat ctc tgc<br>Lys Leu Asn Thr Ser Arg Leu His Arg Val Leu Arg Asn Leu Cys<br>3200                            3205                            3210 | 9639 |
| tac cat gcc cag acc cgc cac tgg gtc atc cgc agt ctg ctc tcc<br>Tyr His Ala Gln Thr Arg His Trp Val Ile Arg Ser Leu Leu Ser<br>3215                            3220                            3225 | 9684 |
| atc ttg cag cgc agc agt gag agt gag cta tgc att gaa aca ccc<br>Ile Leu Gln Arg Ser Ser Glu Ser Glu Leu Cys Ile Glu Thr Pro<br>3230                            3235                            3240 | 9729 |
| aaa ctc act aca agt gag gaa aag ggc aaa aag tcg agc aag agc<br>Lys Leu Thr Thr Ser Glu Glu Lys Gly Lys Lys Ser Ser Lys Ser<br>3245                            3250                            3255 | 9774 |
| tgt ggg tca agt agc cat gag aac cgt ccc ctg gac ctg cta cac<br>Cys Gly Ser Ser Ser His Glu Asn Arg Pro Leu Asp Leu Leu His<br>3260                            3265                            3270 | 9819 |
| aag atg gag tca aag agc tcc aac cag ctt tcc tgg ctc tca gta<br>Lys Met Glu Ser Lys Ser Ser Asn Gln Leu Ser Trp Leu Ser Val<br>3275                            3280                            3285 | 9864 |
| tcc atg gat gca gcc cta ggc tgc agg act aat ata ttt cag atc<br>Ser Met Asp Ala Ala Leu Gly Cys Arg Thr Asn Ile Phe Gln Ile<br>3290                            3295                            3300 | 9909 |
| cag cgt tca ggg ggg cgt aaa cat acc gag aag cat gca agc ggt<br>Gln Arg Ser Gly Gly Arg Lys His Thr Glu Lys His Ala Ser Gly<br>3305                            3310                            3315 | 9954 |
| ggc tcc acc gtc cac atc cat ccc caa gct gct cct gtt gtc tgc<br>Gly Ser Thr Val His Ile His Pro Gln Ala Ala Pro Val Val Cys<br>3320                            3325                            3330 | 9999 |
| aga cac gtt ttg gat aca ctc att caa ttg gcc aag gta ttt ccc<br>Arg His Val Leu Asp Thr Leu Ile Gln Leu Ala Lys Val Phe Pro<br>3335                            3340                            3345 | 10044 |
| agc cac ttc aca cag cag cgg acc aaa gaa aca aac tgt gag agt<br>Ser His Phe Thr Gln Gln Arg Thr Lys Glu Thr Asn Cys Glu Ser<br>3350                            3355                            3360 | 10089 |
| gat cgg gaa agg ggc aat aag gcc tgt agc cca tgc tcc tca cag<br>Asp Arg Glu Arg Gly Asn Lys Ala Cys Ser Pro Cys Ser Ser Gln<br>3365                            3370                            3375 | 10134 |
| tcc tcc agc agt ggc att tgc aca gac ttc tgg gac tta ttg gta<br>Ser Ser Ser Ser Gly Ile Cys Thr Asp Phe Trp Asp Leu Leu Val<br>3380                            3385                            3390 | 10179 |
| aaa ctg gac aac atg aat gtc agc cgg aaa ggc aag aac tcc gtg<br>Lys Leu Asp Asn Met Asn Val Ser Arg Lys Gly Lys Asn Ser Val<br>3395                            3400                            3405 | 10224 |
| aag tca gtg cca gtg agc gct ggc ggt gag ggg gaa acc tct cca<br>Lys Ser Val Pro Val Ser Ala Gly Gly Glu Gly Glu Thr Ser Pro<br>3410                            3415                            3420 | 10269 |

```
tac agc ctc gag gcc tct cca ctg ggg cag ctc atg  aac atg ttg         10314
Tyr Ser Leu Glu Ala Ser Pro Leu Gly Gln Leu Met  Asn Met Leu
    3425                3430                     3435 tca cac cca gtc atc cgc cgg agc tct ctc tta act  gag aaa ctc         10359
Ser His Pro Val Ile Arg Arg Ser Ser Leu Leu Thr  Glu Lys Leu
    3440                3445                     3450 ctc aga ctc ctt tct ctc atc tca att gct ctc cca  gaa aac aag         10404
Leu Arg Leu Leu Ser Leu Ile Ser Ile Ala Leu Pro  Glu Asn Lys
    3455                3460                     3465 gtg tca gaa gca cag gct aat tct ggc agc ggt gct  tcc tcc acc         10449
Val Ser Glu Ala Gln Ala Asn Ser Gly Ser Gly Ala  Ser Ser Thr
    3470                3475                     3480 acc act gcc acc tca acc aca tct acc acc acc act  gcc gcc             10494
Thr Thr Ala Thr Ser Thr Thr Ser Thr Thr Thr Thr  Ala Ala
    3485                3490                3495 tcc acc acg ccc aca ccc cct act gca ccc acc cct  gtc act tct         10539
Ser Thr Thr Pro Thr Pro Pro Thr Ala Pro Thr Pro  Val Thr Ser
    3500                3505                     3510 gct cca gcc ctg gtt gct gcc acg gct att tcc acc  att gtc gta         10584
Ala Pro Ala Leu Val Ala Ala Thr Ala Ile Ser Thr  Ile Val Val
    3515                3520                     3525 gct gct tcg acc aca gtg act acc ccc acg act gct  acc act act         10629
Ala Ala Ser Thr Thr Val Thr Thr Pro Thr Thr Ala  Thr Thr Thr
    3530                3535                     3540 gtt tca att tct ccc act act aag ggc agc aaa tct  cca gcg aag         10674
Val Ser Ile Ser Pro Thr Thr Lys Gly Ser Lys Ser  Pro Ala Lys
    3545                3550                     3555 gtg agt gat ggg ggc agc agc agt aca gac ttt aag  atg gtg tcc         10719
Val Ser Asp Gly Gly Ser Ser Ser Thr Asp Phe Lys  Met Val Ser
    3560                3565                     3570 tct ggc ctc act gaa aac cag cta cag ctc tct gta  gag gtg ttg         10764
Ser Gly Leu Thr Glu Asn Gln Leu Gln Leu Ser Val  Glu Val Leu
    3575                3580                     3585 aca tcc cac tct tgt tct gag gaa ggc tta gag gat  gca gcc aac         10809
Thr Ser His Ser Cys Ser Glu Glu Gly Leu Glu Asp  Ala Ala Asn
    3590                3595                     3600 gta cta ctg cag ctc tcc cgg ggg gac tct ggg acc  cgg gac act         10854
Val Leu Leu Gln Leu Ser Arg Gly Asp Ser Gly Thr  Arg Asp Thr
    3605                3610                     3615 gtt ctc aag ctg cta ctg aat gga gcc cgc cat ctg  ggt tat acc         10899
Val Leu Lys Leu Leu Leu Asn Gly Ala Arg His Leu  Gly Tyr Thr
    3620                3625                     3630 ctt tgt aaa caa ata ggt acc ctg ctg gcc gag ctg  cgg gaa tac         10944
Leu Cys Lys Gln Ile Gly Thr Leu Leu Ala Glu Leu  Arg Glu Tyr
    3635                3640                     3645 aac ctc gag cag cag cgg cga gcc caa tgt gaa acc  ctc tct cct         10989
Asn Leu Glu Gln Gln Arg Arg Ala Gln Cys Glu Thr  Leu Ser Pro
    3650                3655                     3660 gat ggc ctg cct gag gag cag cca cag acc acc aag  ctg aag ggc         11034
Asp Gly Leu Pro Glu Glu Gln Pro Gln Thr Thr Lys  Leu Lys Gly
    3665                3670                     3675 aaa atg cag agc agg ttt gac atg gct gag aat gtg  gta att gtg         11079
Lys Met Gln Ser Arg Phe Asp Met Ala Glu Asn Val  Val Ile Val
    3680                3685                     3690 gca tct cag aag cga cct ttg ggt ggc cgg gag ctc  cag ctg cct         11124
Ala Ser Gln Lys Arg Pro Leu Gly Gly Arg Glu Leu  Gln Leu Pro
    3695                3700                     3705 tct atg tcc atg ttg aca tcc aag aca tct acc cag  aag ttc ttc         11169
Ser Met Ser Met Leu Thr Ser Lys Thr Ser Thr Gln  Lys Phe Phe
```

|  |  |
|---|---|
| ttg agg gta cta cag gtc atc atc cag ctc cgg gac gac acg cgc<br>Leu Arg Val Leu Gln Val Ile Ile Gln Leu Arg Asp Asp Thr Arg<br>    3725                         3730                      3735 | 11214 |
| cgg gct aac aag aaa gcc aag cag aca ggc agg cta ggt tcc tcc<br>Arg Ala Asn Lys Lys Ala Lys Gln Thr Gly Arg Leu Gly Ser Ser<br>    3740                         3745                      3750 | 11259 |
| ggt tta ggc tca gct agc agc atc cag gca gct gtt cgg cag ctg<br>Gly Leu Gly Ser Ala Ser Ser Ile Gln Ala Ala Val Arg Gln Leu<br>    3755                         3760                      3765 | 11304 |
| gag gct gag gct gat gcc att ata caa atg gta cgt gag ggt caa<br>Glu Ala Glu Ala Asp Ala Ile Ile Gln Met Val Arg Glu Gly Gln<br>    3770                         3775                      3780 | 11349 |
| agg gcg cgg aga cag caa caa gca gca acg tcg gag tct agc cag<br>Arg Ala Arg Arg Gln Gln Gln Ala Ala Thr Ser Glu Ser Ser Gln<br>    3785                         3790                      3795 | 11394 |
| tca gag gcg tct gtc cgg agg gag gaa tca ccc atg gat gtg gac<br>Ser Glu Ala Ser Val Arg Arg Glu Glu Ser Pro Met Asp Val Asp<br>    3800                         3805                      3810 | 11439 |
| cag cca tct ccc agt gct caa gat act caa tcc att gcc tcc gat<br>Gln Pro Ser Pro Ser Ala Gln Asp Thr Gln Ser Ile Ala Ser Asp<br>    3815                         3820                      3825 | 11484 |
| gga acc cca cag ggg gag aag gaa aag gaa gaa aga cca cct gag<br>Gly Thr Pro Gln Gly Glu Lys Glu Lys Glu Glu Arg Pro Pro Glu<br>    3830                         3835                      3840 | 11529 |
| tta ccc ctg ctc agc gag cag ctg agt ttg gac gag ctg tgg gac<br>Leu Pro Leu Leu Ser Glu Gln Leu Ser Leu Asp Glu Leu Trp Asp<br>    3845                         3850                      3855 | 11574 |
| atg ctt ggg gag tgt cta aag gaa cta gag gaa tcc cat gac cag<br>Met Leu Gly Glu Cys Leu Lys Glu Leu Glu Glu Ser His Asp Gln<br>    3860                         3865                      3870 | 11619 |
| cat gcg gtg cta gtg cta cag cct gct gtc gag gcc ttc ttt ctg<br>His Ala Val Leu Val Leu Gln Pro Ala Val Glu Ala Phe Phe Leu<br>    3875                         3880                      3885 | 11664 |
| gtc cat gcc aca gag cgg gag agc aag cct cct gtc cga gac acc<br>Val His Ala Thr Glu Arg Glu Ser Lys Pro Pro Val Arg Asp Thr<br>    3890                         3895                      3900 | 11709 |
| cgt gag agc cag ctg gca cac atc aag gac gag cct cct cca ctc<br>Arg Glu Ser Gln Leu Ala His Ile Lys Asp Glu Pro Pro Pro Leu<br>    3905                         3910                      3915 | 11754 |
| tcc cct gcc ccc tta acc cca gcc acg cct tcc tcc ctt gac cca<br>Ser Pro Ala Pro Leu Thr Pro Ala Thr Pro Ser Ser Leu Asp Pro<br>    3920                         3925                      3930 | 11799 |
| ttc ttc tcc cgg gag ccc tca tct atg cac atc tcc tca agc ctg<br>Phe Phe Ser Arg Glu Pro Ser Ser Met His Ile Ser Ser Ser Leu<br>    3935                         3940                      3945 | 11844 |
| ccc cct gac aca cag aag ttc ctt cgc ttt gca gag act cac cgc<br>Pro Pro Asp Thr Gln Lys Phe Leu Arg Phe Ala Glu Thr His Arg<br>    3950                         3955                      3960 | 11889 |
| act gtg tta aac cag atc cta cgg cag tcc acg acc cac ctt gct<br>Thr Val Leu Asn Gln Ile Leu Arg Gln Ser Thr Thr His Leu Ala<br>    3965                         3970                      3975 | 11934 |
| gat ggg cct ttt gct gtc ctg gta gac tac att cgt gtc ctc gac<br>Asp Gly Pro Phe Ala Val Leu Val Asp Tyr Ile Arg Val Leu Asp<br>    3980                         3985                      3990 | 11979 |
| ttt gat gtc aag cgc aaa tat ttc cgc caa gag ctg gag cgt tta<br>Phe Asp Val Lys Arg Lys Tyr Phe Arg Gln Glu Leu Glu Arg Leu<br>    3995                         4000                      4005 | 12024 |
| gat gag ggg ctc cgg aaa gaa gac atg gct gtg cat gtc cgt cgt | 12069 |

| | | | | | | | | | | | | |
|---|---|---|---|---|---|---|---|---|---|---|---|---|
| Asp | Glu | Gly | Leu | Arg | Lys | Glu | Asp | Met | Ala | Val | His | Val Arg Arg |
| 4010 | | | | | 4015 | | | | 4020 | | | |

| | | | | | | | | | | | | |
|---|---|---|---|---|---|---|---|---|---|---|---|---|
| gac | cat | gtg | ttt | gaa | gac | tcc | tat | cgt | gag | ctg | cat | cgc aaa tcc | 12114 |
| Asp | His | Val | Phe | Glu | Asp | Ser | Tyr | Arg | Glu | Leu | His | Arg Lys Ser |
| 4025 | | | | | 4030 | | | | 4035 | | | |

| ccc | gaa | gaa | atg | aag | aat | cga | ttg | tat | ata | gta | ttt | gaa gga gaa | 12159 |
|---|---|---|---|---|---|---|---|---|---|---|---|---|
| Pro | Glu | Glu | Met | Lys | Asn | Arg | Leu | Tyr | Ile | Val | Phe | Glu Gly Glu |
| 4040 | | | | | 4045 | | | | 4050 | | | |

| gaa | ggg | cag | gat | gct | ggc | ggg | ctc | ctg | cgg | gag | tgg | tat atg atc | 12204 |
|---|---|---|---|---|---|---|---|---|---|---|---|---|
| Glu | Gly | Gln | Asp | Ala | Gly | Gly | Leu | Leu | Arg | Glu | Trp | Tyr Met Ile |
| 4055 | | | | | 4060 | | | | 4065 | | | |

| atc | tct | cga | gag | atg | ttt | aac | cct | atg | tat | gcc | ttg | ttc cgt acc | 12249 |
|---|---|---|---|---|---|---|---|---|---|---|---|---|
| Ile | Ser | Arg | Glu | Met | Phe | Asn | Pro | Met | Tyr | Ala | Leu | Phe Arg Thr |
| 4070 | | | | | 4075 | | | | 4080 | | | |

| tca | cct | ggt | gat | cga | gtc | acc | tac | acc | atc | aat | cca | tct tcc cac | 12294 |
|---|---|---|---|---|---|---|---|---|---|---|---|---|
| Ser | Pro | Gly | Asp | Arg | Val | Thr | Tyr | Thr | Ile | Asn | Pro | Ser Ser His |
| 4085 | | | | | 4090 | | | | 4095 | | | |

| tgc | aac | ccc | aac | cac | ctc | agc | tac | ttc | aag | ttt | gtc | gga cgc att | 12339 |
|---|---|---|---|---|---|---|---|---|---|---|---|---|
| Cys | Asn | Pro | Asn | His | Leu | Ser | Tyr | Phe | Lys | Phe | Val | Gly Arg Ile |
| 4100 | | | | | 4105 | | | | 4110 | | | |

| gtg | gcc | aaa | gct | gta | tat | gac | aac | cgt | ctt | ctg | gag | tgc tac ttt | 12384 |
|---|---|---|---|---|---|---|---|---|---|---|---|---|
| Val | Ala | Lys | Ala | Val | Tyr | Asp | Asn | Arg | Leu | Leu | Glu | Cys Tyr Phe |
| 4115 | | | | | 4120 | | | | 4125 | | | |

| act | cga | tcc | ttt | tac | aaa | cac | atc | ttg | ggc | aag | tca | gtc aga tat | 12429 |
|---|---|---|---|---|---|---|---|---|---|---|---|---|
| Thr | Arg | Ser | Phe | Tyr | Lys | His | Ile | Leu | Gly | Lys | Ser | Val Arg Tyr |
| 4130 | | | | | 4135 | | | | 4140 | | | |

| aca | gat | atg | gag | agt | gaa | gat | tac | cac | ttc | tac | caa | ggt ctg gtt | 12474 |
|---|---|---|---|---|---|---|---|---|---|---|---|---|
| Thr | Asp | Met | Glu | Ser | Glu | Asp | Tyr | His | Phe | Tyr | Gln | Gly Leu Val |
| 4145 | | | | | 4150 | | | | 4155 | | | |

| tat | ctg | ctg | gaa | aat | gat | gtc | tcc | aca | cta | ggc | tat | gac ctc acc | 12519 |
|---|---|---|---|---|---|---|---|---|---|---|---|---|
| Tyr | Leu | Leu | Glu | Asn | Asp | Val | Ser | Thr | Leu | Gly | Tyr | Asp Leu Thr |
| 4160 | | | | | 4165 | | | | 4170 | | | |

| ttc | agc | act | gag | gtc | caa | gag | ttt | gga | gtt | tgt | gaa | gtt cgt gac | 12564 |
|---|---|---|---|---|---|---|---|---|---|---|---|---|
| Phe | Ser | Thr | Glu | Val | Gln | Glu | Phe | Gly | Val | Cys | Glu | Val Arg Asp |
| 4175 | | | | | 4180 | | | | 4185 | | | |

| ctc | aaa | ccc | aat | ggg | gcc | aac | atc | ttg | gta | aca | gag | gag aat aag | 12609 |
|---|---|---|---|---|---|---|---|---|---|---|---|---|
| Leu | Lys | Pro | Asn | Gly | Ala | Asn | Ile | Leu | Val | Thr | Glu | Glu Asn Lys |
| 4190 | | | | | 4195 | | | | 4200 | | | |

| aag | gag | tat | gta | cac | ctg | gta | tgc | cag | atg | aga | atg | aca gga gcc | 12654 |
|---|---|---|---|---|---|---|---|---|---|---|---|---|
| Lys | Glu | Tyr | Val | His | Leu | Val | Cys | Gln | Met | Arg | Met | Thr Gly Ala |
| 4205 | | | | | 4210 | | | | 4215 | | | |

| atc | cgc | aag | cag | ttg | gcg | gct | ttc | tta | gaa | ggc | ttc | tat gag atc | 12699 |
|---|---|---|---|---|---|---|---|---|---|---|---|---|
| Ile | Arg | Lys | Gln | Leu | Ala | Ala | Phe | Leu | Glu | Gly | Phe | Tyr Glu Ile |
| 4220 | | | | | 4225 | | | | 4230 | | | |

| att | cca | aag | cgc | ctc | att | tcc | atc | ttc | act | gag | cag | gag tta gag | 12744 |
|---|---|---|---|---|---|---|---|---|---|---|---|---|
| Ile | Pro | Lys | Arg | Leu | Ile | Ser | Ile | Phe | Thr | Glu | Gln | Glu Leu Glu |
| 4235 | | | | | 4240 | | | | 4245 | | | |

| ctg | ctt | ata | tca | gga | ctg | ccc | acc | att | gac | atc | gat | gat ctg aaa | 12789 |
|---|---|---|---|---|---|---|---|---|---|---|---|---|
| Leu | Leu | Ile | Ser | Gly | Leu | Pro | Thr | Ile | Asp | Ile | Asp | Asp Leu Lys |
| 4250 | | | | | 4255 | | | | 4260 | | | |

| tcc | aac | act | gaa | tac | cac | aag | tac | cag | tcc | aac | tct | att cag atc | 12834 |
|---|---|---|---|---|---|---|---|---|---|---|---|---|
| Ser | Asn | Thr | Glu | Tyr | His | Lys | Tyr | Gln | Ser | Asn | Ser | Ile Gln Ile |
| 4265 | | | | | 4270 | | | | 4275 | | | |

| cag | tgg | ttc | tgg | aga | gca | ttg | cgt | tct | ttc | gat | caa | gct gac cgt | 12879 |
|---|---|---|---|---|---|---|---|---|---|---|---|---|
| Gln | Trp | Phe | Trp | Arg | Ala | Leu | Arg | Ser | Phe | Asp | Gln | Ala Asp Arg |
| 4280 | | | | | 4285 | | | | 4290 | | | |

| gcc | aag | ttc | ctc | cag | ttt | gtc | acg | ggt | act | tcc | aag | gta ccc ctg | 12924 |
|---|---|---|---|---|---|---|---|---|---|---|---|---|
| Ala | Lys | Phe | Leu | Gln | Phe | Val | Thr | Gly | Thr | Ser | Lys | Val Pro Leu |
| 4295 | | | | | 4300 | | | | 4305 | | | |

```
caa ggc ttt gct gcc ctc gaa ggc atg aat ggc att cag aag ttt    12969
Gln Gly Phe Ala Ala Leu Glu Gly Met Asn Gly Ile Gln Lys Phe
4310            4315                4320 cag atc cat cga gat gac agg tcc aca gat cgc ctg cct tca gct    13014
Gln Ile His Arg Asp Asp Arg Ser Thr Asp Arg Leu Pro Ser Ala
    4325            4330                4335 cac aca tgt ttt aat cag ctg gat ctg cct gcc tat gag agc ttt    13059
His Thr Cys Phe Asn Gln Leu Asp Leu Pro Ala Tyr Glu Ser Phe
4340            4345                4350 gag aag ctc cgc cac atg cta ctg ttg gct atc cag gag tgc tct    13104
Glu Lys Leu Arg His Met Leu Leu Leu Ala Ile Gln Glu Cys Ser
    4355            4360                4365 gaa ggc ttt ggg ctg gcc taa taaggccctg cccaactccg tggggttttt   13155
Glu Gly Phe Gly Leu Ala
    4370 tttaccattg ttggacctgg ggagggggga gttaaaaaaa gaaccagaaa gaaattgtca   13215 aaaaccaata aatgaaatcc accaactcac cgtgtgtgtc ccagctgccc catcttcccc    13275 agcgcatacc tgttcctctt ctcattctct ccccgccgcc tgtttcctca ccttctctcc    13335 cctttccatg ccgtccatga tccccacccc atgtgtttta aaaggcagt agcctttgca    13395 gggacctgtc tgtcccaact gttttgaacag tgtgctcctc agattctgtg ttcagaagga   13455 tttgctgcat tgagacttga aacctttgga taggggaaaa aattatatat atatatattt    13515 ttttgttctg tttgcatttc ttaatttgtg cttggaatgt gttgatgtgc acagctaatg    13575 attcaatgcg agacaagatt ggcgtctgtg ttgtggaggt ttcaaataaa gagcactctt    13635 cataactcaa aaaaaaaaaa aaaaaaaaaa aaaaaa                             13671
```

<210> SEQ ID NO 2
<211> LENGTH: 4374
<212> TYPE: PRT
<213> ORGANISM: Homo sapiens

<400> SEQUENCE: 2

```
Met Lys Val Asp Arg Thr Lys Leu Lys Lys Thr Pro Thr Glu Ala Pro
1               5                   10                  15

Ala Asp Cys Arg Ala Leu Ile Asp Lys Leu Lys Val Cys Asn Asp Glu
            20                  25                  30

Gln Leu Leu Leu Glu Leu Gln Gln Ile Lys Thr Trp Asn Ile Gly Lys
        35                  40                  45

Cys Glu Leu Tyr His Trp Val Asp Leu Leu Asp Arg Phe Asp Gly Ile
    50                  55                  60

Leu Ala Asp Ala Gly Gln Thr Val Glu Asn Met Ser Trp Met Leu Val
65                  70                  75                  80

Cys Asp Arg Pro Glu Arg Glu Gln Leu Lys Met Leu Leu Leu Ala Val
                85                  90                  95

Leu Asn Phe Thr Ala Leu Leu Ile Glu Tyr Ser Phe Ser Arg His Leu
            100                 105                 110

Tyr Ser Ser Ile Glu His Leu Thr Thr Leu Leu Ala Ser Ser Asp Met
        115                 120                 125

Gln Val Val Leu Ala Val Leu Asn Leu Leu Tyr Val Phe Ser Lys Arg
    130                 135                 140

Ser Asn Tyr Ile Thr Arg Leu Gly Ser Asp Lys Arg Thr Pro Leu Leu
145                 150                 155                 160

Thr Arg Leu Gln His Leu Ala Glu Ser Trp Gly Gly Lys Glu Asn Gly
                165                 170                 175
```

```
Phe Gly Leu Ala Glu Cys Cys Arg Asp Leu His Met Met Lys Tyr Pro
            180                 185                 190

Pro Ser Ala Thr Thr Leu His Phe Glu Phe Tyr Ala Asp Pro Gly Ala
        195                 200                 205

Glu Val Lys Ile Glu Lys Arg Thr Thr Ser Asn Thr Leu His Tyr Ile
    210                 215                 220

His Ile Glu Gln Leu Asp Lys Ile Ser Glu Ser Pro Ser Glu Ile Met
225                 230                 235                 240

Glu Ser Leu Thr Lys Met Tyr Ser Ile Pro Lys Asp Lys Gln Met Leu
                245                 250                 255

Leu Phe Thr His Ile Arg Leu Ala His Gly Phe Ser Asn His Arg Lys
            260                 265                 270

Arg Leu Gln Ala Val Gln Ala Arg Leu His Ala Ile Ser Ile Leu Val
        275                 280                 285

Tyr Ser Asn Ala Leu Gln Glu Ser Ala Asn Ser Ile Leu Tyr Asn Gly
    290                 295                 300

Leu Ile Glu Glu Leu Val Asp Val Leu Gln Ile Thr Asp Lys Gln Leu
305                 310                 315                 320

Met Glu Ile Lys Ala Ala Ser Leu Arg Thr Leu Thr Ser Ile Val His
                325                 330                 335

Leu Glu Arg Thr Pro Lys Leu Ser Ser Ile Ile Asp Cys Thr Gly Thr
            340                 345                 350

Ala Ser Tyr His Gly Phe Leu Pro Val Leu Arg Asn Cys Ile Gln
        355                 360                 365

Ala Met Ile Asp Pro Ser Met Asp Pro Tyr Pro His Gln Phe Ala Thr
    370                 375                 380

Ala Leu Phe Ser Phe Leu Tyr His Leu Ala Ser Tyr Asp Ala Gly Gly
385                 390                 395                 400

Glu Ala Leu Val Ser Cys Gly Met Met Glu Ala Leu Leu Lys Val Ile
                405                 410                 415

Lys Phe Leu Gly Asp Glu Gln Asp Gln Ile Thr Phe Val Thr Arg Ala
            420                 425                 430

Val Arg Val Val Asp Leu Ile Thr Asn Leu Asp Met Ala Ala Phe Gln
        435                 440                 445

Ser His Ser Gly Leu Ser Ile Phe Ile Tyr Arg Leu Glu His Glu Val
    450                 455                 460

Asp Leu Cys Arg Lys Glu Cys Pro Phe Val Ile Lys Pro Lys Ile Gln
465                 470                 475                 480

Arg Pro Asn Thr Thr Gln Glu Gly Glu Glu Met Glu Thr Asp Met Asp
                485                 490                 495

Gly Val Gln Cys Ile Pro Gln Arg Ala Ala Leu Leu Lys Ser Met Leu
            500                 505                 510

Asn Phe Leu Lys Lys Ala Ile Gln Asp Pro Ala Phe Ser Asp Gly Ile
        515                 520                 525

Arg His Val Met Asp Gly Ser Leu Pro Thr Ser Leu Lys His Ile Ile
    530                 535                 540

Ser Asn Ala Glu Tyr Tyr Gly Pro Ser Leu Phe Leu Leu Ala Thr Glu
545                 550                 555                 560

Val Val Thr Val Phe Val Phe Gln Glu Pro Ser Leu Leu Ser Ser Leu
                565                 570                 575

Gln Asp Asn Gly Leu Thr Asp Val Met Leu His Ala Leu Leu Ile Lys
            580                 585                 590

Asp Val Pro Ala Thr Arg Glu Val Leu Gly Ser Leu Pro Asn Val Phe
```

-continued

```
            595                 600                 605
Ser Ala Leu Cys Leu Asn Ala Arg Gly Leu Gln Ser Phe Val Gln Cys
        610                 615                 620
Gln Pro Phe Glu Arg Leu Phe Lys Val Leu Leu Ser Pro Asp Tyr Leu
625                 630                 635                 640
Pro Ala Met Arg Arg Arg Ser Ser Asp Pro Leu Gly Asp Thr Ala
                645                 650                 655
Ser Asn Leu Gly Ser Ala Val Asp Glu Leu Met Arg His Gln Pro Thr
            660                 665                 670
Leu Lys Thr Asp Ala Thr Thr Ala Ile Ile Lys Leu Leu Glu Glu Ile
            675                 680                 685
Cys Asn Leu Gly Arg Asp Pro Lys Tyr Ile Cys Gln Lys Pro Ser Ile
        690                 695                 700
Gln Lys Ala Asp Gly Thr Ala Thr Ala Pro Pro Arg Ser Asn His
705                 710                 715                 720
Ala Ala Glu Glu Ala Ser Ser Glu Asp Glu Glu Glu Glu Val Gln
                725                 730                 735
Ala Met Gln Ser Phe Asn Ser Thr Gln Gln Asn Glu Thr Glu Pro Asn
            740                 745                 750
Gln Gln Val Val Gly Thr Glu Glu Arg Ile Pro Ile Pro Leu Met Asp
        755                 760                 765
Tyr Ile Leu Asn Val Met Lys Phe Val Glu Ser Ile Leu Ser Asn Asn
        770                 775                 780
Thr Thr Asp Asp His Cys Gln Glu Phe Val Asn Gln Lys Gly Leu Leu
785                 790                 795                 800
Pro Leu Val Thr Ile Leu Gly Leu Pro Asn Leu Pro Ile Asp Phe Pro
                805                 810                 815
Thr Ser Ala Ala Cys Gln Ala Val Ala Gly Val Cys Lys Ser Ile Leu
            820                 825                 830
Thr Leu Ser His Glu Pro Lys Val Leu Gln Glu Gly Leu Leu Gln Leu
            835                 840                 845
Asp Ser Ile Leu Ser Ser Leu Glu Pro Leu His Arg Pro Ile Glu Ser
850                 855                 860
Pro Gly Gly Ser Val Leu Leu Arg Glu Leu Ala Cys Ala Gly Asn Val
865                 870                 875                 880
Ala Asp Ala Thr Leu Ser Ala Gln Ala Thr Pro Leu Leu His Ala Leu
                885                 890                 895
Thr Ala Ala His Ala Tyr Ile Met Met Phe Val His Thr Cys Arg Val
            900                 905                 910
Gly Gln Ser Glu Ile Arg Ser Ile Ser Val Asn Gln Trp Gly Ser Gln
            915                 920                 925
Leu Gly Leu Ser Val Leu Ser Lys Leu Ser Gln Leu Tyr Cys Ser Leu
        930                 935                 940
Val Trp Glu Ser Thr Val Leu Leu Ser Leu Cys Thr Pro Asn Ser Leu
945                 950                 955                 960
Pro Ser Gly Cys Glu Phe Gly Gln Ala Asp Met Gln Lys Leu Val Pro
                965                 970                 975
Lys Asp Glu Lys Ala Gly Thr Thr Gln Gly Gly Lys Arg Ser Asp Gly
            980                 985                 990
Glu Gln Asp Gly Ala Ala Gly Ser  Met Asp Ala Ser Thr  Gln Gly Leu
        995                 1000                1005
Leu Glu  Gly Ile Gly Leu Asp  Gly Asp Thr Leu Ala  Pro Met Glu
    1010                1015                1020
```

-continued

```
Thr Asp Glu Pro Thr Ala Ser Asp Ser Lys Gly Lys Ser Lys Ile
    1025                1030                1035

Thr Pro Ala Met Ala Ala Arg Ile Lys Gln Ile Lys Pro Leu Leu
    1040                1045                1050

Ser Ala Ser Ser Arg Leu Gly Arg Ala Leu Ala Glu Leu Phe Gly
    1055                1060                1065

Leu Leu Val Lys Leu Cys Val Gly Ser Pro Val Arg Gln Arg Arg
    1070                1075                1080

Ser His His Ala Ala Ser Thr Thr Ala Pro Thr Pro Ala Ala
    1085                1090                1095

Arg Ser Thr Ala Ser Ala Leu Thr Lys Leu Leu Thr Lys Gly Leu
    1100                1105                1110

Ser Trp Gln Pro Pro Tyr Thr Pro Thr Pro Arg Phe Arg Leu
    1115                1120                1125

Thr Phe Phe Ile Cys Ser Val Gly Phe Thr Ser Pro Met Leu Phe
    1130                1135                1140

Asp Glu Arg Lys Tyr Pro Tyr His Leu Met Leu Gln Lys Phe Leu
    1145                1150                1155

Cys Ser Gly Gly His Asn Ala Leu Phe Glu Thr Phe Asn Trp Ala
    1160                1165                1170

Leu Ser Met Gly Gly Lys Val Pro Val Ser Glu Gly Leu Glu His
    1175                1180                1185

Ser Asp Leu Pro Asp Gly Thr Gly Glu Phe Leu Asp Ala Trp Leu
    1190                1195                1200

Met Leu Val Glu Lys Met Val Asn Pro Thr Thr Val Leu Glu Ser
    1205                1210                1215

Pro His Ser Leu Pro Ala Lys Leu Pro Gly Gly Val Gln Asn Phe
    1220                1225                1230

Pro Gln Phe Ser Ala Leu Arg Phe Leu Val Val Thr Gln Lys Ala
    1235                1240                1245

Ala Phe Thr Cys Ile Lys Asn Leu Trp Asn Arg Lys Pro Leu Lys
    1250                1255                1260

Val Tyr Gly Gly Arg Met Ala Glu Ser Met Leu Ala Ile Leu Cys
    1265                1270                1275

His Ile Leu Arg Gly Glu Pro Val Ile Arg Glu Arg Leu Ser Lys
    1280                1285                1290

Glu Lys Glu Gly Ser Arg Gly Glu Glu Asp Thr Gly Gln Glu Glu
    1295                1300                1305

Gly Gly Ser Arg Arg Glu Pro Gln Val Asn Gln Gln Gln Leu Gln
    1310                1315                1320

Gln Leu Met Asp Met Gly Phe Thr Arg Glu His Ala Met Glu Ala
    1325                1330                1335

Leu Leu Asn Thr Ser Thr Met Glu Gln Ala Thr Glu Tyr Leu Leu
    1340                1345                1350

Thr His Pro Pro Pro Ile Met Gly Gly Val Val Arg Asp Leu Ser
    1355                1360                1365

Met Ser Glu Glu Asp Gln Met Met Arg Ala Ile Ala Met Ser Leu
    1370                1375                1380

Gly Gln Asp Ile Pro Met Asp Gln Arg Ala Glu Ser Pro Glu Glu
    1385                1390                1395

Val Ala Cys Arg Lys Glu Glu Glu Glu Arg Lys Ala Arg Glu Lys
    1400                1405                1410
```

-continued

```
Gln Glu Glu Glu Ala Lys Cys Leu Glu Lys Phe Gln Asp Ala
    1415            1420            1425

Asp Pro Leu Glu Gln Asp Glu Leu His Thr Phe Thr Asp Thr Met
    1430            1435            1440

Leu Pro Gly Cys Phe His Leu Leu Asp Glu Leu Pro Asp Thr Val
    1445            1450            1455

Tyr Arg Val Cys Asp Leu Ile Met Thr Ala Ile Lys Arg Asn Gly
    1460            1465            1470

Ala Asp Tyr Arg Asp Met Ile Leu Lys Gln Val Val Asn Gln Val
    1475            1480            1485

Trp Glu Ala Ala Asp Val Leu Ile Lys Ala Ala Leu Pro Leu Thr
    1490            1495            1500

Thr Ser Asp Thr Lys Thr Val Ser Glu Trp Ile Ser Gln Met Ala
    1505            1510            1515

Thr Leu Pro Gln Ala Ser Asn Leu Ala Thr Arg Ile Leu Leu Leu
    1520            1525            1530

Thr Leu Leu Phe Glu Glu Leu Lys Leu Pro Cys Ala Trp Val Val
    1535            1540            1545

Glu Ser Ser Gly Ile Leu Asn Val Leu Ile Lys Leu Leu Glu Val
    1550            1555            1560

Val Gln Pro Cys Leu Gln Ala Ala Lys Glu Gln Lys Glu Val Gln
    1565            1570            1575

Thr Pro Lys Trp Ile Thr Pro Val Leu Leu Leu Ile Asp Phe Tyr
    1580            1585            1590

Glu Lys Thr Ala Ile Ser Ser Lys Arg Arg Ala Gln Met Thr Lys
    1595            1600            1605

Tyr Leu Gln Ser Asn Ser Asn Asn Trp Arg Trp Phe Asp Asp Arg
    1610            1615            1620

Ser Gly Arg Trp Cys Ser Tyr Ser Ala Ser Asn Asn Ser Thr Ile
    1625            1630            1635

Asp Ser Ala Trp Lys Ser Gly Glu Thr Ser Val Arg Phe Thr Ala
    1640            1645            1650

Gly Arg Arg Arg Tyr Thr Val Gln Phe Thr Thr Met Val Gln Val
    1655            1660            1665

Asn Glu Glu Thr Gly Asn Arg Arg Pro Val Met Leu Thr Leu Leu
    1670            1675            1680

Arg Val Pro Arg Leu Asn Lys Asn Ser Lys Asn Ser Asn Gly Gln
    1685            1690            1695

Glu Leu Glu Lys Thr Leu Glu Glu Ser Lys Glu Met Asp Ile Lys
    1700            1705            1710

Arg Lys Glu Asn Lys Gly Asn Asp Thr Pro Leu Ala Leu Glu Ser
    1715            1720            1725

Thr Asn Thr Glu Lys Glu Thr Ser Leu Glu Glu Thr Lys Ile Gly
    1730            1735            1740

Glu Ile Leu Ile Gln Gly Leu Thr Glu Asp Met Val Thr Val Leu
    1745            1750            1755

Ile Arg Ala Cys Val Ser Met Leu Gly Val Pro Val Asp Pro Asp
    1760            1765            1770

Thr Leu His Ala Thr Leu Arg Leu Cys Leu Arg Leu Thr Arg Asp
    1775            1780            1785

His Lys Tyr Ala Met Met Phe Ala Glu Leu Lys Ser Thr Arg Met
    1790            1795            1800

Ile Leu Asn Leu Thr Gln Ser Ser Gly Phe Asn Gly Phe Thr Pro
```

-continued

|      |      | 1805 |      |      |      | 1810 |      |      |      | 1815 |      |
|------|------|------|------|------|------|------|------|------|------|------|------|

Leu Val Thr Leu Leu Leu Arg His Ile Ile Glu Asp Pro Cys Thr
1820                1825                1830

Leu Arg His Thr Met Glu Lys Val Val Arg Ser Ala Ala Thr Ser
1835                1840                1845

Gly Ala Gly Ser Thr Thr Ser Gly Val Val Ser Gly Ser Leu Gly
1850                1855                1860

Ser Arg Glu Ile Asn Tyr Ile Leu Arg Val Leu Gly Pro Ala Ala
1865                1870                1875

Cys Arg Asn Pro Asp Ile Phe Thr Glu Val Ala Asn Cys Cys Ile
1880                1885                1890

Arg Ile Ala Leu Pro Ala Pro Arg Gly Ser Gly Thr Ala Ser Asp
1895                1900                1905

Asp Glu Phe Glu Asn Leu Arg Ile Lys Gly Pro Asn Ala Val Gln
1910                1915                1920

Leu Val Lys Thr Thr Pro Leu Lys Pro Ser Pro Leu Pro Val Ile
1925                1930                1935

Pro Asp Thr Ile Lys Glu Val Ile Tyr Asp Met Leu Asn Ala Leu
1940                1945                1950

Ala Ala Tyr His Ala Pro Glu Glu Ala Asp Lys Ser Asp Pro Lys
1955                1960                1965

Pro Gly Val Met Thr Gln Glu Val Gly Gln Leu Leu Gln Asp Met
1970                1975                1980

Gly Asp Asp Val Tyr Gln Gln Tyr Arg Ser Leu Thr Arg Gln Ser
1985                1990                1995

Ser Asp Phe Asp Thr Gln Ser Gly Phe Ser Ile Asn Ser Gln Val
2000                2005                2010

Phe Ala Ala Asp Gly Ala Ser Thr Glu Thr Ser Ala Ser Gly Thr
2015                2020                2025

Ser Gln Gly Glu Ala Ser Thr Pro Glu Gly Ser Arg Asp Gly Lys
2030                2035                2040

Lys Asp Lys Glu Gly Asp Arg Ala Ser Glu Glu Gly Lys Gln Lys
2045                2050                2055

Gly Lys Gly Ser Lys Pro Leu Met Pro Thr Ser Thr Ile Leu Arg
2060                2065                2070

Leu Leu Ala Glu Leu Val Arg Ser Tyr Val Gly Ile Ala Thr Leu
2075                2080                2085

Ile Ala Asn Tyr Ser Tyr Thr Val Gly Gln Ser Glu Leu Ile Lys
2090                2095                2100

Glu Asp Cys Ser Val Leu Ala Phe Val Leu Asp His Leu Leu Pro
2105                2110                2115

His Thr Gln Asn Ala Glu Asp Lys Asp Thr Pro Ala Leu Ala Arg
2120                2125                2130

Leu Phe Leu Ala Ser Leu Ala Ala Ala Gly Ser Gly Thr Asp Ala
2135                2140                2145

Gln Val Ala Leu Val Asn Glu Val Lys Ala Ala Leu Gly Arg Ala
2150                2155                2160

Leu Ala Met Ala Glu Ser Thr Glu Lys His Ala Arg Leu Gln Ala
2165                2170                2175

Val Met Cys Ile Ile Ser Thr Ile Met Glu Ser Cys Pro Ser Thr
2180                2185                2190

Ser Ser Phe Tyr Ser Ser Ala Thr Ala Lys Thr Gln His Asn Gly
2195                2200                2205

-continued

```
Met Asn Asn Ile Ile Arg Leu Phe Leu Lys Lys Gly Leu Val Asn
2210                2215                2220

Asp Leu Ala Arg Val Pro His Ser Leu Asp Leu Ser Ser Pro Asn
2225                2230                2235

Met Ala Asn Thr Val Asn Ala Ala Leu Lys Pro Leu Glu Thr Leu
2240                2245                2250

Ser Arg Ile Val Asn Gln Pro Ser Ser Leu Phe Gly Ser Lys Ser
2255                2260                2265

Ala Ser Ser Lys Asn Lys Ser Glu Gln Asp Ala Gln Gly Ala Ser
2270                2275                2280

Gln Asp Ser Ser Ser Asn Gln Gln Asp Pro Gly Glu Pro Gly Glu
2285                2290                2295

Ala Glu Val Gln Glu Glu Asp His Asp Val Thr Gln Thr Glu Val
2300                2305                2310

Ala Asp Gly Asp Ile Met Asp Gly Glu Ala Glu Thr Asp Ser Val
2315                2320                2325

Val Ile Ala Gly Gln Pro Glu Val Leu Ser Ser Gln Glu Met Gln
2330                2335                2340

Val Glu Asn Glu Leu Glu Asp Leu Ile Asp Glu Leu Leu Glu Arg
2345                2350                2355

Asp Gly Gly Ser Gly Asn Ser Thr Ile Ile Val Ser Arg Ser Gly
2360                2365                2370

Glu Asp Glu Ser Gln Glu Asp Val Leu Met Asp Glu Ala Pro Ser
2375                2380                2385

Asn Leu Ser Gln Ala Ser Thr Leu Gln Ala Asn Arg Glu Asp Ser
2390                2395                2400

Met Asn Ile Leu Asp Pro Glu Asp Glu Glu His Thr Gln Glu
2405                2410                2415

Glu Asp Ser Ser Gly Ser Asn Glu Asp Glu Asp Ser Gln Asp
2420                2425                2430

Glu Glu Glu Glu Glu Glu Glu Asp Glu Glu Asp Gln Glu Asp
2435                2440                2445

Asp Glu Gly Glu Glu Gly Asp Glu Asp Asp Asp Asp Gly Ser
2450                2455                2460

Glu Met Glu Leu Asp Glu Asp Tyr Pro Asp Met Asn Ala Ser Pro
2465                2470                2475

Leu Val Arg Phe Glu Arg Phe Asp Arg Glu Asp Asp Leu Ile Ile
2480                2485                2490

Glu Phe Asp Asn Met Phe Ser Ser Ala Thr Asp Ile Pro Pro Ser
2495                2500                2505

Pro Gly Asn Ile Pro Thr Thr His Pro Leu Met Val Arg His Ala
2510                2515                2520

Asp His Ser Ser Leu Thr Leu Gly Ser Gly Ser Ser Thr Thr Arg
2525                2530                2535

Leu Thr Gln Gly Ile Gly Arg Ser Gln Arg Thr Leu Arg Gln Leu
2540                2545                2550

Thr Ala Asn Thr Gly His Thr Ile His Val His Tyr Pro Gly Asn
2555                2560                2565

Arg Gln Pro Asn Pro Pro Leu Ile Leu Gln Arg Leu Leu Gly Pro
2570                2575                2580

Ser Ala Ala Ala Asp Ile Leu Gln Leu Ser Ser Ser Leu Pro Leu
2585                2590                2595
```

-continued

```
Gln Ser Arg Gly Arg Ala Arg Leu Leu Val Gly Asn Asp Asp Val
    2600            2605                2610
His Ile Ile Ala Arg Ser Asp Asp Glu Leu Leu Asp Asp Phe Phe
    2615            2620                2625
His Asp Gln Ser Thr Ala Thr Ser Gln Ala Gly Thr Leu Ser Ser
    2630            2635                2640
Ile Pro Thr Ala Leu Thr Arg Trp Thr Glu Glu Cys Lys Val Leu
    2645            2650                2655
Asp Ala Glu Ser Met His Asp Cys Val Ser Val Lys Val Ser
    2660            2665                2670
Ile Val Asn His Leu Glu Phe Leu Arg Asp Glu Glu Leu Glu Glu
    2675            2680                2685
Arg Arg Glu Lys Arg Lys Gln Leu Ala Glu Glu Thr Lys
    2690            2695                2700
Ile Thr Asp Lys Gly Lys Glu Asp Lys Glu Asn Arg Asp Gln Ser
    2705            2710                2715
Ala Gln Cys Thr Ala Ser Lys Ser Asn Asp Ser Thr Glu Gln Asn
    2720            2725                2730
Leu Ser Asp Gly Thr Pro Met Pro Asp Ser Tyr Pro Thr Thr Pro
    2735            2740                2745
Ser Ser Thr Asp Ala Ala Thr Ser Glu Ser Lys Glu Thr Leu Gly
    2750            2755                2760
Thr Leu Gln Ser Ser Gln Gln Gln Pro Thr Leu Pro Thr Pro Pro
    2765            2770                2775
Ala Leu Gly Glu Val Pro Gln Glu Leu Gln Ser Pro Ala Gly Glu
    2780            2785                2790
Gly Gly Ser Ser Thr Gln Leu Leu Met Pro Val Glu Pro Glu Glu
    2795            2800                2805
Leu Gly Pro Thr Arg Pro Ser Gly Glu Ala Glu Thr Thr Gln Met
    2810            2815                2820
Glu Leu Ser Pro Ala Pro Thr Ile Thr Ser Leu Ser Pro Glu Arg
    2825            2830                2835
Ala Glu Asp Ser Asp Ala Leu Thr Ala Val Ser Ser Gln Leu Glu
    2840            2845                2850
Gly Ser Pro Met Asp Thr Ser Ser Leu Ala Ser Cys Thr Leu Glu
    2855            2860                2865
Glu Ala Val Gly Asp Thr Ser Ala Ala Gly Ser Ser Glu Gln Pro
    2870            2875                2880
Arg Ala Gly Ser Ser Thr Pro Gly Asp Ala Pro Pro Ala Val Ala
    2885            2890                2895
Glu Val Gln Gly Arg Ser Asp Gly Ser Gly Glu Ser Ala Gln Pro
    2900            2905                2910
Pro Glu Asp Ser Ser Pro Pro Ala Ser Ser Glu Ser Ser Ser Thr
    2915            2920                2925
Arg Asp Ser Ala Val Ala Ile Ser Gly Ala Asp Ser Arg Gly Ile
    2930            2935                2940
Leu Glu Glu Pro Leu Pro Ser Thr Ser Ser Glu Glu Glu Asp Pro
    2945            2950                2955
Leu Ala Gly Ile Ser Leu Pro Glu Gly Val Asp Pro Ser Phe Leu
    2960            2965                2970
Ala Ala Leu Pro Asp Asp Ile Arg Arg Glu Val Leu Gln Asn Gln
    2975            2980                2985
Leu Gly Ile Arg Pro Pro Thr Arg Thr Ala Pro Ser Thr Asn Ser
```

-continued

```
              2990            2995            3000
Ser Ala Pro Ala Val Val Gly Asn Pro Gly Val Thr Glu Val Ser
    3005            3010            3015

Pro Glu Phe Leu Ala Ala Leu Pro Pro Ala Ile Gln Glu Glu Val
    3020            3025            3030

Leu Ala Gln Gln Arg Ala Glu Gln Gln Arg Arg Glu Leu Ala Gln
    3035            3040            3045

Asn Ala Ser Ser Asp Thr Pro Met Asp Pro Val Thr Phe Ile Gln
    3050            3055            3060

Thr Leu Pro Ser Asp Leu Arg Arg Ser Val Leu Glu Asp Met Glu
    3065            3070            3075

Asp Ser Val Leu Ala Val Met Pro Pro Asp Ile Ala Ala Glu Ala
    3080            3085            3090

Gln Ala Leu Arg Arg Glu Gln Glu Ala Arg Gln Arg Gln Leu Met
    3095            3100            3105

His Glu Arg Leu Phe Gly His Ser Ser Thr Ser Ala Leu Ser Ala
    3110            3115            3120

Ile Leu Arg Ser Pro Ala Phe Thr Ser Arg Leu Ser Gly Asn Arg
    3125            3130            3135

Gly Val Gln Tyr Thr Arg Leu Ala Val Gln Arg Gly Gly Thr Phe
    3140            3145            3150

Gln Met Gly Gly Ser Ser Ser His Asn Arg Pro Ser Gly Ser Asn
    3155            3160            3165

Val Asp Thr Leu Leu Arg Leu Arg Gly Arg Leu Leu Leu Asp His
    3170            3175            3180

Glu Ala Leu Ser Cys Leu Leu Val Leu Leu Phe Val Asp Glu Pro
    3185            3190            3195

Lys Leu Asn Thr Ser Arg Leu His Arg Val Leu Arg Asn Leu Cys
    3200            3205            3210

Tyr His Ala Gln Thr Arg His Trp Val Ile Arg Ser Leu Leu Ser
    3215            3220            3225

Ile Leu Gln Arg Ser Ser Glu Ser Glu Leu Cys Ile Glu Thr Pro
    3230            3235            3240

Lys Leu Thr Thr Ser Glu Glu Lys Gly Lys Lys Ser Ser Lys Ser
    3245            3250            3255

Cys Gly Ser Ser Ser His Glu Asn Arg Pro Leu Asp Leu Leu His
    3260            3265            3270

Lys Met Glu Ser Lys Ser Ser Asn Gln Leu Ser Trp Leu Ser Val
    3275            3280            3285

Ser Met Asp Ala Ala Leu Gly Cys Arg Thr Asn Ile Phe Gln Ile
    3290            3295            3300

Gln Arg Ser Gly Gly Arg Lys His Thr Glu Lys His Ala Ser Gly
    3305            3310            3315

Gly Ser Thr Val His Ile His Pro Gln Ala Ala Pro Val Val Cys
    3320            3325            3330

Arg His Val Leu Asp Thr Leu Ile Gln Leu Ala Lys Val Phe Pro
    3335            3340            3345

Ser His Phe Thr Gln Gln Arg Thr Lys Glu Thr Asn Cys Glu Ser
    3350            3355            3360

Asp Arg Glu Arg Gly Asn Lys Ala Cys Ser Pro Cys Ser Ser Gln
    3365            3370            3375

Ser Ser Ser Ser Gly Ile Cys Thr Asp Phe Trp Asp Leu Leu Val
    3380            3385            3390
```

-continued

```
Lys Leu Asp Asn Met Asn Val Ser Arg Lys Gly Lys Asn Ser Val
    3395                3400                3405

Lys Ser Val Pro Val Ser Ala Gly Gly Glu Gly Glu Thr Ser Pro
    3410                3415                3420

Tyr Ser Leu Glu Ala Ser Pro Leu Gly Gln Leu Met Asn Met Leu
    3425                3430                3435

Ser His Pro Val Ile Arg Arg Ser Ser Leu Leu Thr Glu Lys Leu
    3440                3445                3450

Leu Arg Leu Leu Ser Leu Ile Ser Ile Ala Leu Pro Glu Asn Lys
    3455                3460                3465

Val Ser Glu Ala Gln Ala Asn Ser Gly Ser Gly Ala Ser Ser Thr
    3470                3475                3480

Thr Thr Ala Thr Ser Thr Thr Ser Thr Thr Thr Thr Thr Ala Ala
    3485                3490                3495

Ser Thr Thr Pro Thr Pro Pro Thr Ala Pro Thr Pro Val Thr Ser
    3500                3505                3510

Ala Pro Ala Leu Val Ala Ala Thr Ala Ile Ser Thr Ile Val Val
    3515                3520                3525

Ala Ala Ser Thr Thr Val Thr Thr Pro Thr Thr Ala Thr Thr Thr
    3530                3535                3540

Val Ser Ile Ser Pro Thr Thr Lys Gly Ser Lys Ser Pro Ala Lys
    3545                3550                3555

Val Ser Asp Gly Gly Ser Ser Ser Thr Asp Phe Lys Met Val Ser
    3560                3565                3570

Ser Gly Leu Thr Glu Asn Gln Leu Gln Leu Ser Val Glu Val Leu
    3575                3580                3585

Thr Ser His Ser Cys Ser Glu Glu Gly Leu Glu Asp Ala Ala Asn
    3590                3595                3600

Val Leu Leu Gln Leu Ser Arg Gly Asp Ser Gly Thr Arg Asp Thr
    3605                3610                3615

Val Leu Lys Leu Leu Leu Asn Gly Ala Arg His Leu Gly Tyr Thr
    3620                3625                3630

Leu Cys Lys Gln Ile Gly Thr Leu Leu Ala Glu Leu Arg Glu Tyr
    3635                3640                3645

Asn Leu Glu Gln Gln Arg Arg Ala Gln Cys Glu Thr Leu Ser Pro
    3650                3655                3660

Asp Gly Leu Pro Glu Glu Gln Pro Gln Thr Thr Lys Leu Lys Gly
    3665                3670                3675

Lys Met Gln Ser Arg Phe Asp Met Ala Glu Asn Val Val Ile Val
    3680                3685                3690

Ala Ser Gln Lys Arg Pro Leu Gly Gly Arg Glu Leu Gln Leu Pro
    3695                3700                3705

Ser Met Ser Met Leu Thr Ser Lys Thr Ser Thr Gln Lys Phe Phe
    3710                3715                3720

Leu Arg Val Leu Gln Val Ile Ile Gln Leu Arg Asp Asp Thr Arg
    3725                3730                3735

Arg Ala Asn Lys Lys Ala Lys Gln Thr Gly Arg Leu Gly Ser Ser
    3740                3745                3750

Gly Leu Gly Ser Ala Ser Ser Ile Gln Ala Ala Val Arg Gln Leu
    3755                3760                3765

Glu Ala Glu Ala Asp Ala Ile Ile Gln Met Val Arg Glu Gly Gln
    3770                3775                3780
```

-continued

| | | | | | | | | | | | |
|---|---|---|---|---|---|---|---|---|---|---|---|
| Arg | Ala | Arg | Arg | Gln | Gln | Gln | Ala | Ala | Thr | Ser | Glu | Ser | Ser | Gln |
| | 3785 | | | | 3790 | | | | 3795 | | |
| Ser | Glu | Ala | Ser | Val | Arg | Arg | Glu | Glu | Ser | Pro | Met | Asp | Val | Asp |
| | 3800 | | | | 3805 | | | | 3810 | | |
| Gln | Pro | Ser | Pro | Ser | Ala | Gln | Asp | Thr | Gln | Ser | Ile | Ala | Ser | Asp |
| | 3815 | | | | 3820 | | | | 3825 | | |
| Gly | Thr | Pro | Gln | Gly | Glu | Lys | Glu | Lys | Glu | Glu | Arg | Pro | Pro | Glu |
| | 3830 | | | | 3835 | | | | 3840 | | |
| Leu | Pro | Leu | Leu | Ser | Glu | Gln | Leu | Ser | Leu | Asp | Glu | Leu | Trp | Asp |
| | 3845 | | | | 3850 | | | | 3855 | | |
| Met | Leu | Gly | Glu | Cys | Leu | Lys | Glu | Leu | Glu | Glu | Ser | His | Asp | Gln |
| | 3860 | | | | 3865 | | | | 3870 | | |
| His | Ala | Val | Leu | Val | Leu | Gln | Pro | Ala | Val | Glu | Ala | Phe | Phe | Leu |
| | 3875 | | | | 3880 | | | | 3885 | | |
| Val | His | Ala | Thr | Glu | Arg | Glu | Ser | Lys | Pro | Pro | Val | Arg | Asp | Thr |
| | 3890 | | | | 3895 | | | | 3900 | | |
| Arg | Glu | Ser | Gln | Leu | Ala | His | Ile | Lys | Asp | Glu | Pro | Pro | Pro | Leu |
| | 3905 | | | | 3910 | | | | 3915 | | |
| Ser | Pro | Ala | Pro | Leu | Thr | Pro | Ala | Thr | Pro | Ser | Ser | Leu | Asp | Pro |
| | 3920 | | | | 3925 | | | | 3930 | | |
| Phe | Phe | Ser | Arg | Glu | Pro | Ser | Ser | Met | His | Ile | Ser | Ser | Ser | Leu |
| | 3935 | | | | 3940 | | | | 3945 | | |
| Pro | Pro | Asp | Thr | Gln | Lys | Phe | Leu | Arg | Phe | Ala | Glu | Thr | His | Arg |
| | 3950 | | | | 3955 | | | | 3960 | | |
| Thr | Val | Leu | Asn | Gln | Ile | Leu | Arg | Gln | Ser | Thr | Thr | His | Leu | Ala |
| | 3965 | | | | 3970 | | | | 3975 | | |
| Asp | Gly | Pro | Phe | Ala | Val | Leu | Val | Asp | Tyr | Ile | Arg | Val | Leu | Asp |
| | 3980 | | | | 3985 | | | | 3990 | | |
| Phe | Asp | Val | Lys | Arg | Lys | Tyr | Phe | Arg | Gln | Glu | Leu | Glu | Arg | Leu |
| | 3995 | | | | 4000 | | | | 4005 | | |
| Asp | Glu | Gly | Leu | Arg | Lys | Glu | Asp | Met | Ala | Val | His | Val | Arg | Arg |
| | 4010 | | | | 4015 | | | | 4020 | | |
| Asp | His | Val | Phe | Glu | Asp | Ser | Tyr | Arg | Glu | Leu | His | Arg | Lys | Ser |
| | 4025 | | | | 4030 | | | | 4035 | | |
| Pro | Glu | Glu | Met | Lys | Asn | Arg | Leu | Tyr | Ile | Val | Phe | Glu | Gly | Glu |
| | 4040 | | | | 4045 | | | | 4050 | | |
| Glu | Gly | Gln | Asp | Ala | Gly | Gly | Leu | Leu | Arg | Glu | Trp | Tyr | Met | Ile |
| | 4055 | | | | 4060 | | | | 4065 | | |
| Ile | Ser | Arg | Glu | Met | Phe | Asn | Pro | Met | Tyr | Ala | Leu | Phe | Arg | Thr |
| | 4070 | | | | 4075 | | | | 4080 | | |
| Ser | Pro | Gly | Asp | Arg | Val | Thr | Tyr | Thr | Ile | Asn | Pro | Ser | Ser | His |
| | 4085 | | | | 4090 | | | | 4095 | | |
| Cys | Asn | Pro | Asn | His | Leu | Ser | Tyr | Phe | Lys | Phe | Val | Gly | Arg | Ile |
| | 4100 | | | | 4105 | | | | 4110 | | |
| Val | Ala | Lys | Ala | Val | Tyr | Asp | Asn | Arg | Leu | Leu | Glu | Cys | Tyr | Phe |
| | 4115 | | | | 4120 | | | | 4125 | | |
| Thr | Arg | Ser | Phe | Tyr | Lys | His | Ile | Leu | Gly | Lys | Ser | Val | Arg | Tyr |
| | 4130 | | | | 4135 | | | | 4140 | | |
| Thr | Asp | Met | Glu | Ser | Glu | Asp | Tyr | His | Phe | Tyr | Gln | Gly | Leu | Val |
| | 4145 | | | | 4150 | | | | 4155 | | |
| Tyr | Leu | Leu | Glu | Asn | Asp | Val | Ser | Thr | Leu | Gly | Tyr | Asp | Leu | Thr |
| | 4160 | | | | 4165 | | | | 4170 | | |
| Phe | Ser | Thr | Glu | Val | Gln | Glu | Phe | Gly | Val | Cys | Glu | Val | Arg | Asp |

-continued

```
               4175               4180               4185
Leu Lys Pro Asn Gly Ala Asn Ile Leu Val Thr Glu Glu Asn Lys
    4190                4195                4200

Lys Glu Tyr Val His Leu Val Cys Gln Met Arg Met Thr Gly Ala
    4205                4210                4215

Ile Arg Lys Gln Leu Ala Ala Phe Leu Glu Gly Phe Tyr Glu Ile
    4220                4225                4230

Ile Pro Lys Arg Leu Ile Ser Ile Phe Thr Glu Gln Glu Leu Glu
    4235                4240                4245

Leu Leu Ile Ser Gly Leu Pro Thr Ile Asp Ile Asp Asp Leu Lys
    4250                4255                4260

Ser Asn Thr Glu Tyr His Lys Tyr Gln Ser Asn Ser Ile Gln Ile
    4265                4270                4275

Gln Trp Phe Trp Arg Ala Leu Arg Ser Phe Asp Gln Ala Asp Arg
    4280                4285                4290

Ala Lys Phe Leu Gln Phe Val Thr Gly Thr Ser Lys Val Pro Leu
    4295                4300                4305

Gln Gly Phe Ala Ala Leu Glu Gly Met Asn Gly Ile Gln Lys Phe
    4310                4315                4320

Gln Ile His Arg Asp Asp Arg Ser Thr Asp Arg Leu Pro Ser Ala
    4325                4330                4335

His Thr Cys Phe Asn Gln Leu Asp Leu Pro Ala Tyr Glu Ser Phe
    4340                4345                4350

Glu Lys Leu Arg His Met Leu Leu Leu Ala Ile Gln Glu Cys Ser
    4355                4360                4365

Glu Gly Phe Gly Leu Ala
    4370
```

METHOD FOR IDENTIFYING COMPOUNDS THAT INHIBIT THE ACTIVITY OF MYC

RELATED APPLICATIONS

This application claims priority to European Patent Application EP 04011505.7, filed May 14, 2004. The contents of which are incorporated herein.

DISCLOSURE OF THE INVENTION

The present invention relates to the therapy of cancer. In particular, the present invention relates to methods for identifying compounds that have the potential to inhibit the activity of the proto-oncogene Myc and may thus be useful for the therapy of cancer.

The proto-oncogene c-myc encodes a transcription factor (Myc) that can both activate and repress transcription. Myc activates transcription as part of a binary complex with its partner protein, Max. The complex binds to specific DNA sequences, termed E-boxes, and recruits a number of co-activators to DNA; indeed, four distinct classes of co-activators have been described that may mediate transcriptional activation by Myc.

First, a short conserved domain in the amino-terminus of Myc ("MycboxII") binds to the TRRAP protein and Myc recruits the histone acetyl-transferases, Tip60 and GCN5 via binding to TRAPP. Similarly, Myc recruits the p300 and CBP acetyl-transferases though a direct interaction of the terminus-terminus of Myc with each protein. Second, Myc interacts with mediator complexes in vitro and recruits mediator to E-boxes in vivo independently of histone acetylation, suggesting that interactions with mediator complexes contribute to transcriptional activation by Myc. Third, Myc recruits the E3-ligase Skp2 to DNA and recruitment of Skp2 contributes to transcriptional activation by Myc. Fourth, Myc binds to BAF53, a subunit of the chromatin-remodeling BAF complex, implying chromatin-remodeling as a mechanism that may contribute to Myc-dependent gene activation. The precise contribution of each co-factor to the activation of individual genes by Myc is largely unknown.

Myc represses transcription at least in part through the formation of a ternary complex that contains Max and the transcription factor, Miz1. Miz1 binds to the start site of several Myc-repressed genes and activates these genes. Myc does not bind to the start sites of Myc-repressed genes directly but is recruited to these sites through interaction with Miz1. In contrast to free Miz1, the Myc/Miz1 complex acts as a transcriptional repressor complex.

Free Miz1 requires p300 as co-activator and binding of Myc to Miz1 displaces p300 from Miz1, explaining in part how Myc inhibits transactivation by Miz1. However, transcriptional repression by Myc requires domains in the amino-terminus that are not required for displacement of p300 from Miz1, suggesting that additional co-factors contribute to transcriptional repression by Myc.

The (c-) MYC gene and two of its relatives, MYCN or MYCL, contribute to the genesis of a wide variety of human tumors. In these tumors, the expression of MYC genes is enhanced relative to the surrounding or normal tissue, arguing that there is a selective pressure for high expression of Myc proteins during tumor development. For example, the MYCN gene is amplified in a subset of childhood neuroblastoma, correlating with extremely poor prognosis of the affected children (Brodeur et al., 1984; Schwab et al., 1983). In other tumors, expression of a MYC family gene is increased because mutations occur in the signaling pathway that control their expression: one example are the mutations in the APC pathway that affect cMYC expression in colorectal carcinomas (He et al., 1998; van de Wetering et al., 2002).

Besides colon cancer, elevated or deregulated expression of c-Myc has been detected in a wide range of human cancers and is often associated with aggressive, poorly differentiated tumors. Such cancers include breast, cervical, small cell lung carcinomas, osteosarcomas, glioblastomas, melanoma and myeloid leukemias (reviewed in Pelengaris et al., 2002b).

Examples of Myc-activated target genes, whose activation results in stimulation of tumor growth, proliferation and survival are cyclin D2 and CDK4, which are important for cell cycle progression, the translation initiation factors eIF4 and eIF2 that are important for cell growth, as well as ornithine decarboxylase and carbamyl-phosphate synthase, enzymes required for polyamine and pyrimidine biosynthesis, respectively (reviewed in Grandori and Eisenman, 1997; Pelengaris et al., 2002b). Examples of Myc-repressed genes, whose repression results in cell proliferation, are the cell cycle inhibitors p15ink4b and p21Cip1.

Inhibition of Myc activity is a highly attractive approach for drug discovery in oncology, since recent experimental data suggest that even a brief inhibition of Myc expression may be sufficient to permanently stop tumor growth and induce regression of tumors. Jain et al. (2002) engineered a conditional transgenic mouse to overexpress Myc, which induced formation of highly malignant osteogenic sarcoma. A brief loss of Myc overexpression caused the tumor cells to differentiate into mature osteocytes that formed histologically normal bone. Felsher and Bishop (1999) showed that transgenic mice expressing the myc oncogene in hematopoietic cells developed malignant T cell leukemias and acute myeloid leukemias. However, when this gene was switched off the leukemic cells underwent proliferative arrest, differentiation, and apoptosis. Pelengaris et al. (1999) targeted expression of an inducible form of the c-Myc protein to the epidermis of mice and observed formation of angiogenic premalignant skin lesions, which regressed when the c-Myc protein was deactivated.

In general, specific pharmacological interference with the function of transcription factors has been difficult to achieve. This is particularly true for Myc: despite its obvious value as a potential target for tumor therapy, no drugs have emerged that specifically interfere with its function. For example, screens aimed at disrupting the Myc/Max interface have only yielded compounds with extremely low potency (Berg et al., 2002).

It was an object of the invention to elucidate the mechanisms that regulate the activation and thus the transcriptional activity of Myc. The knowledge about such mechanisms is the key for providing screening assay methods for identifying compounds that have the potential to interfere with the activation of Myc and thus to be useful in the therapy of cancer.

As mentioned above, it has been suggested that Myc may exist in an activating and in a repressive state, potentially depending on the site its binds to DNA and/or its site-specific interaction partners.

In the experiments of the invention, it has surprisingly been found that the E3-ligase HectH9 ubiquitinates Myc on lysine residues close to the carboxyl-terminus of Myc. It could be shown that ubiquitination does not target Myc for degradation, but is required for the recruitment of the co-activator p300. It was shown that ubiquitination of Myc by HectH9 is inhibited by Miz1. Since Miz1 binds to the start site of many Myc-repressed genes but is absent from E-box elements in vivo, the findings of the invention show a mechanism how the transcriptional properties of Myc are regulated by the local chromatin environment. In particular, the findings of the present invention show for the first time the critical role of the E3-ligase HectH9 for Myc activation.

Miz1 is a zinc finger transcription factor that carries at its amino-terminus a POZ-domain. POZ domains are protein-protein interaction modules; in Miz1, the POZ-domain is required for transcriptional activation by Miz1.

In order to understand the function of this domain in more detail, the inventor performed a two-hybrid screen looking for novel interaction partners. In this screen, the inventor obtained multiple clones that are derived from a single gene, which encodes a HECT-domain E3-ligase alternatively named "HectH9", LASU1 (GenBank Accession Nos. AB071605 and BAC06833) or KIAA0312 (GenBank Accession No. AB002310) (FIG. 1a). A protein corresponding to the carboxyl-terminus of HectH9 has also been described as a DNA binding protein ("UREB 1; Upstream-element-binding protein 1" SwissProt Accession No. Q7Z6Z7; Gu et al. 1994). The full-length HectH9 protein is available as GenBank Accession No. NP_113584 (SEQ ID NO:2; DNA sequence SEQ ID NO:1). Although UREBl has been described as a DNA binding protein, the inventor has been unable to confirm a significant DNA binding activity of HectH9.

HectH9 belongs to the HECT-domain family of ubiquitin ligases ("homologous to E6AP carboxy-terminus"), which are characterized by a conserved carboxy-terminal catalytic domain. Among the conserved amino acids is a cysteine residue, which is required for thioester formation with ubiquitin. The clones recovered in the two-hybrid screen conducted in the experiments of the invention define a small region sufficient for interaction with Miz1. The amino-terminus of HectH9 contains two UBA (ubiquitin associated motif) domains, that are known to bind ubiquitin in several ubiquitin-binding proteins, a WWE protein-interaction domain and two putative nuclear localization signals (NLS). Consistent with the presence of two NLS, two different antibodies directed against HectH9 detected the endogenous protein in the cell nucleus of Hela cells (FIG. 1b and data not shown). Controls using cells that were stably transfected with a pSUPER vector, which directs the synthesis of a siRNA against HectH9, showed that the signal detected in the immune-fluorescence is specific for HectH9 (FIG. 1b, middle panel). Immunoblots confirmed that cells transfected with pSUPER-HectH9 expressed lower levels of protein than cells transfected with an empty pSUPER vector (FIG. 1b, lower panel).

To test whether HectH9 binds to Miz1 in vitro, Miz1 and HectH9 were synthesized by coupled transcription-translation in a reticulocyte lysate in the presence of $^{35}$S-methionine (FIG. 1c). After synthesis, lysates were mixed and immuno-precipitated either with antibodies directed against HectH9 or a control serum. Miz1 was clearly detectable in anti-HectH9 immunoprecipitates, whereas control precipitates contained significantly lower levels of Miz1. To test whether the POZ domain of Miz1 is required for binding, the experiment was repeated with ΔPOZ 1. No ΔPOZ-Miz1 was recovered in anti-HectH9 precipitates, demonstrating that the POZ-domain of Miz1 mediates binding to HectH9 in vitro. The inventor also tested whether HectH9 binds to Myc in vitro and did not detect an interaction between HectH9 and Myc in these experiments.

To test whether Miz1 binds to HectH9 in vivo, the inventor transfected HeLa cells with expression vectors encoding Miz1, Miz1ΔPOZ and HectH9. Miz1 was recovered in anti-HectH9 immunoprecipitates, whereas control immunoprecipitates contained significantly less Miz1. No specific binding of Miz1 ΔPOZ to HectH9 could be detected in vivo, consistent with the in vitro and two-hybrid data. α-HectH9 immunoprecipitates contained significant amounts of Myc, demonstrating that Myc binds to HectH9 in vivo. Most likely, therefore, binding of Myc to HectH9 is stabilized by additional proteins in vivo.

Hect-domain proteins act as E3-ligases that ubiquitinate proteins to which they bind. To test whether HectH9 ubiquitinates either Miz1 or Myc, the inventor transfected cells with expression plasmids encoding Myc, Miz1, HectH9 and a histidine-tagged ubiquitin. Transfected cells were lysed and ubiquitinated proteins were isolated by binding to Ni-agarose. Immunoblots of the eluates were probed with antibodies directed against Miz1 and Myc (FIG. 2a and data not shown). In these experiments, the inventor did not detect any activity of HectH9 against Miz1. In contrast, HectH9 efficiently ubiquitinated Myc when both protein were co-expressed in the absence of Miz1. In these experiments, the inventor noted ubiquitinated forms of Myc up to a molecular weight of 250 kd, strongly suggesting that HectH9 catalyzes the transfer of multiple ubiquitin moieties on Myc. Co-expression of Miz1 essentially abolished ubiquitination of Myc by Miz1. Progressive amino-terminal deletions in HectH9 revealed that the Miz1 binding domain on HectH9 is required for ubiquitination of Myc, suggesting that Myc and Miz1 compete for binding to HectH9 (data not shown).

HectH9 might catalyze ubiquitination of Myc in two different manners: it might either catalyze the complex formation of Myc with an unknown E3-ligase or itself be the catalytically active E3-ligase. To distinguish between the two possibilities, the inventor introduced a single point mutation into the carboxyl-terminus of HectH9 that replaces the catalytic cysteine with a serine. HectH9CS, in contrast to wild type HectH9, did not ubiquitinate Myc in vivo, demonstrating that the catalytic activity of HectH9 is required for ubiquitination of Myc in vivo (FIG. 2b).

Surprisingly, neither overexpression nor depletion of HectH9 had any detectable effect of Myc stability in several assays (data not shown). In order to be able to assess the functional consequences of HectH9-mediated ubiquitination of Myc, the inventor therefore decided to map the lysine residues in Myc that are targeted by HectH9 (FIG. 3). To do so, the inventor measured in parallel both binding to HectH9 and ubiquitination by HectH9 of a series of both N-terminal and C-terminal deletion mutants described by Tansey and colleagues (FIG. 3a). In these experiments, full-length Myc bound efficiently to HectH9 and was efficiently ubiquitinated by HectH9, as described above (FIG. 3b). Deletion from the amino-terminus led to a progressive loss of both binding and ubiquitination: for both ΔN1Myc and ΔN2Myc, residual binding could be detected and there was some residual ubiquitination. In contrast, ΔN3Myc neither bound HectH9 nor was ubiquitinated by HectH9. Most likely, therefore, the amino-terminus of Myc is required for binding to HectH9 and the loss of ubiquitination of amino-terminally deleted mutants of Myc by HectH9 is an indirect consequence of the reduction in binding of such proteins.

Both ΔC1Myc and ΔC2Myc bound efficiently to Myc in vivo (FIG. 3c). ΔC1Myc was ubiquitinated by HectH9 to the same extent as wild type Myc. In contrast, ΔC2Myc was not detectably ubiquitinated by HectH9. Since ΔC2Myc bound to HectH9 but was not ubiquitinated, the inventor speculated that the region between AC1 and AC2 might contain the target lysines for HectH9. To test this idea, the inventor replaced the six lysines in this region by arginine in full-length Myc, generating MycKR$_6$.

Immunofluorescence experiments revealed that K6R was localized in the cell nucleus, demonstrating that replacement of the lysines in the nuclear localisation signal by arginine did not induce gross alterations in the subcellular localisation. The inventor next repeated the ubiquitination assays using wild type Myc and MycKR$_6$ in parallel. Ubiquitination of MycKR$_6$ by HectH9 was strongly reduced relative to wild type Myc (FIG. 3d), although it was not completely abolished. Strikingly, also the basal ubiquitination that occurs in the absence of co-expressed HectH9 was strongly reduced relative to wild-type Myc, demonstrating that a significant percentage of ubiquitination of Myc occurs on one or more of the six lysine residues the inventor has identified (FIG. 3d, lower panel).

To test whether ubiquitination of Myc at these sites triggers degradation of Myc, the inventor infected NIH3T3 cells with recombinant retroviruses that express Myc or MycKR$_6$. Pools of infected cells were treated with cycloheximide for different lengths of time (FIG. 4a). Cell lysates were prepared and immunoblots were probed with the monoclonal antibody 9E10, which specifically recognizes human Myc. In these experiments, the inventor observed that the rate of degradation of wild type Myc and MycKR$_6$ was identical. Quantitation of the results (FIG. 4b) showed that the half-time of MycKR$_6$ was unaltered relative to wild type Myc. From these results and those described above, the inventor concluded that ubiquitination by HectH9 does not regulate the stability of the Myc protein.

Several types of poly-ubiquitin chains can be attached to target proteins and only those, in which ubiquitin is linked through lysine-48 target proteins for proteasomal degradation. In contrast, poly-ubiquitin chains with a lysine-63 linkage do not target proteins to the proteasome. In order to determine the type of linkage, which HectH9 transfers to Myc, the inventor performed ubiquitination assays using specific point mutants of his-tagged ubiquitin, in which either lysine 48 or lysine 63 is replaced by an arginine (FIG. 4c). Mutation of lysine 48 did not affect the ability of HectH9 to transfer ubiquitin on Myc; in contrast, mutation of lysine 63 abolished the ability of HectH9 to transfer ubiquitin on Myc. The inventor concluded that HectH9 catalyzes the assembly of a lysine-63 linked poly-ubiquitin chain on Myc.

Polyubiquitination can affect the function of the protein in different ways. In order to test how ubiquitination affects the function of Myc, the inventor initially performed transient reporter assays. No difference was seen in the ability of MycKR$_6$ to inhibit Miz1 dependent transactivation in these assays (data not shown). Also, no difference was seen in the ability of Myc and MycKR$_6$ to activate an E-box dependent reporter derived from the prothymosin-α gene, in transient transfection assays.

In order to test whether these effects extend to the regulation of endogenous target genes by Myc, the inventor infected NIH3T3 cells with retroviruses expressing either Myc, MycKR$_6$ or an empty control vector (pBabepuro). Cells were then serum-starved for 48 hours to deplete endogenous Myc and then RNA was extracted and subjected to an array analysis using an 11.5 k cDNA array (FIG. 5b). This analysis revealed a class of genes that was consistently downregulated in cells expressing KR6 relative to cells expressing wildtype Myc. Comparison with a database of Myc target genes revealed that 80% of these genes were known target for activation of Myc. RT-PCR analysis confirmed the differences in expression of these genes between cells expressing Myc and MycKR$_6$ (FIG. 5c). However, not all targets of Myc were differentially expressed between cells expressing Myc and MycKR$_6$: for example, nucleolin and Rbb2 were induced equally well by both Myc and MycKR$_6$. Taken together, the data show that MycKR$_6$ is deficient in activation of a subset of Myc target genes in vivo.

The six lysines that are replaced by arginines in KR6 are located in a domain that has recently been shown to be involved in binding of the p300 and CBP co-activator. The inventor therefore speculated that ubiquitination of Myc might be required for efficient recruitment of p300. To test this idea, the inventor co-transfected cells with HA-tagged p300 and either Myc or MyckKR$_6$, either by itself or in the presence of HectH9. Lysates were then immunoprecipitated with antibodies against the HA-tag of p300 and the precipitates probed with antibodies directed against Myc (FIG. 5c). In these experiments, efficient complex formation between Myc and p300 was observed in the presence of HectH9, but not in its absence. Importantly, the efficiency of complex formation was reduced for MycKR$_6$, suggesting that the lysine residues need to be ubiquitinated for complex formation to occur. The data strongly suggest that MycKR$_6$ is deficient in transactivation of some target genes becuase binding of Myc to p300 requires ubiquitination at one or more of the six lysines targeted by HectH9.

One prediction from this model is that Myc should recruit p300 sleectively to E-box elements, but not to Miz1 sites, since Miz1 inhibits ubiquitination by HectH9 (see FIG. 2a). The inventor tested this model using a cell line that carries a tetracyclin-inducible Myc. Chromatin-immunoprecipitation was performed both before and after induction of Myc; as targets, the inventor chose nucleolin (E-box dependent activation by Myc) and c/EBPα (a Miz1-dependent target of repression), since initial experiments had shown that the amount of Myc bound to both loci is comparable to each other and higher than for several other genes tested (FIG. 5d, and data not shown). Induction of Myc led to a similar increase of Myc binding at both loci. At the nucleolin locus, there was a clear increase in binding of p300; in contrast, the amount of p300 at the c/EBPα locus remained unaltered. Similar experiments using antibodies directed against TRRAP, p400, Tip60 and Tip48/49 did not reveal a similar difference (data not shown), arguing that MycboxII-dependent interactions occur at both sites of activation and repression.

In summary, the experiments of the present invention have shown that the HECT-domain E3-Ligase HectH9 ubiquitinates Myc; Miz1 inhibits ubiquitination of Myc. Ubiquitination of Myc by HectH9 does not regulate Myc stability, since the polyubiquitin chain is linked via lysine-63 of ubiquitin. Rather, ubiquitination is required for transactivation of specific Myc target genes and for recruitment of the co-activator, p300. From this it is concluded that the transcriptional properties of Myc are regulated by site-specific ubiquitination. These findings make, for the first time, the cancer target Myc accessible for screening assays that allow for identifying Myc inhibitors useful in cancer therapy. (In the context of Myc inhibition, "activation of Myc" and "activity of Myc" are used interchangeably).

WO 01/75145 describes a method for assaying ubiquitin ligase, in which the amount of a tagged ubiquitin that is bound to an E3 is measured, without using a specific target. While HECT domain E3-ligases are mentioned and exemplified by the mammalian E6AP-E6 complex, which functions as a ubiquitin ligase for the tumor suppressor p53, WO 01/75145 does not mention HectH9, neither as such nor in the context with myc.

U.S. Pat. No. 5,968,761 describes an assay for identifying an inhibitor of ubiquitin-mediated proteolysis of a cell-cycle regulatory protein, inter alia myc, in which the level of ubiquitination of the regulatory protein is measured. Again, apart from the fact that this assay aims at identifying inhibitors of proteolysis of a cell-cycle regulatory protein and not of its activation, HectH9 is not among the E3-ligases that are mentioned. The same is true for the review article by Sun, 2003, which suggests targeting E3 ubiquitin ligases for cancer therapy.

BRIEF SUMMARY OF THE INVENTION

Figure 1A:
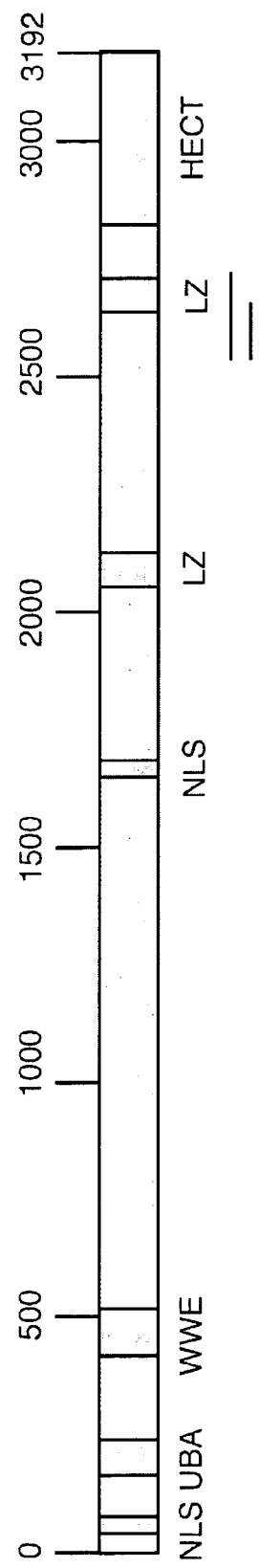
FIG. 1a-1d shows the interaction of Myc and Miz1 with HectH9
Figure 1B:
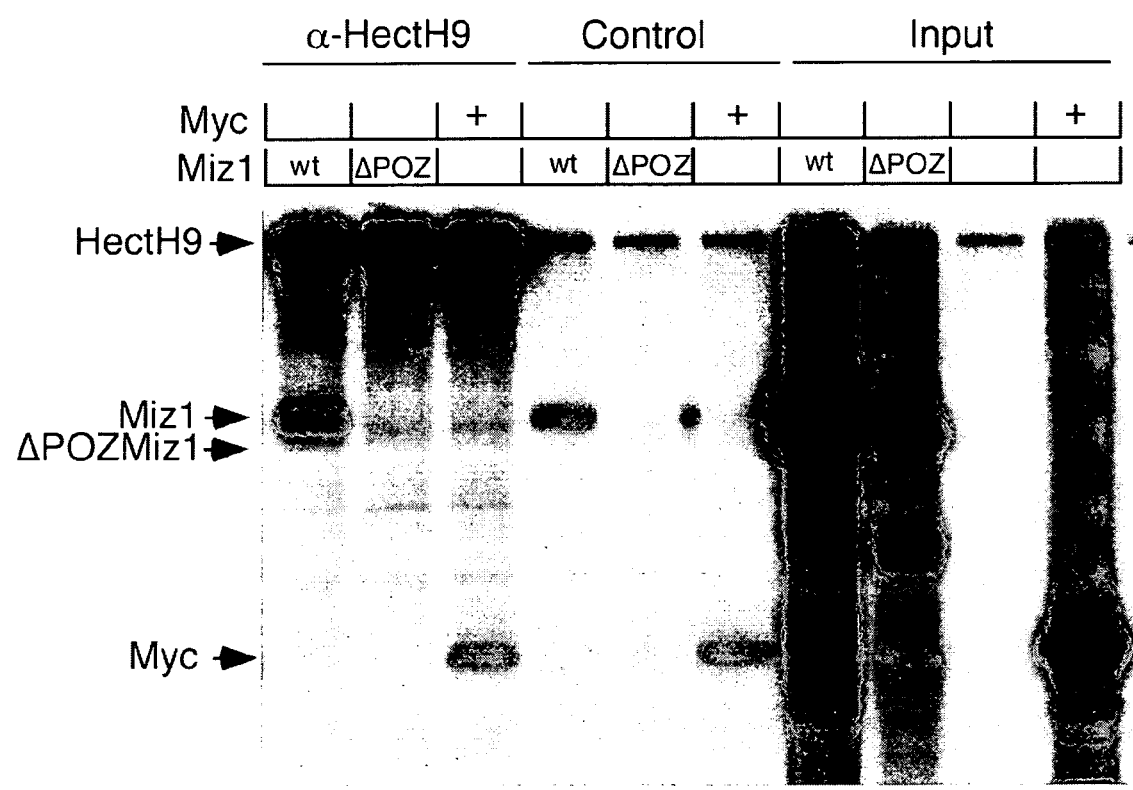
Figure 1C:
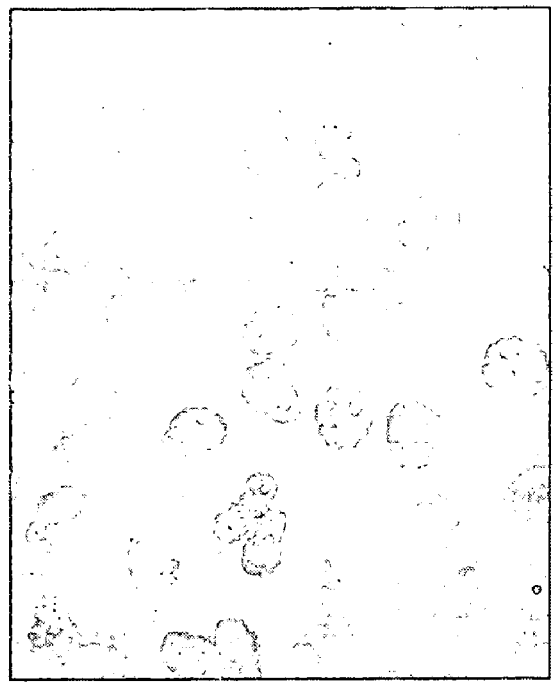
Figure 1C:
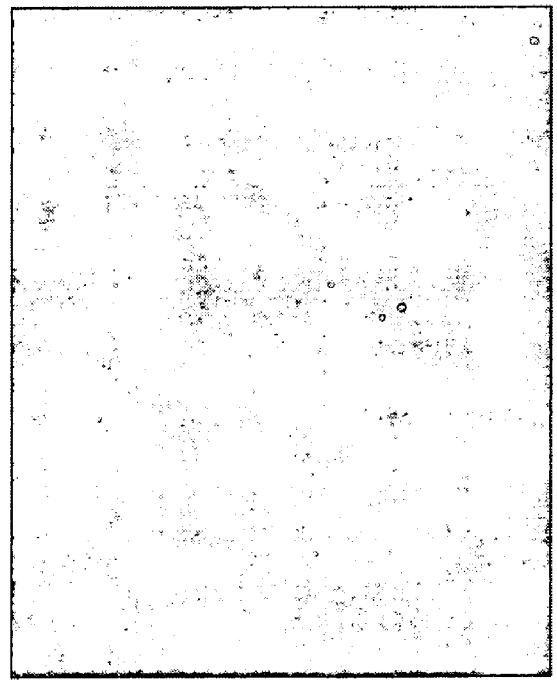
Figure 1D:
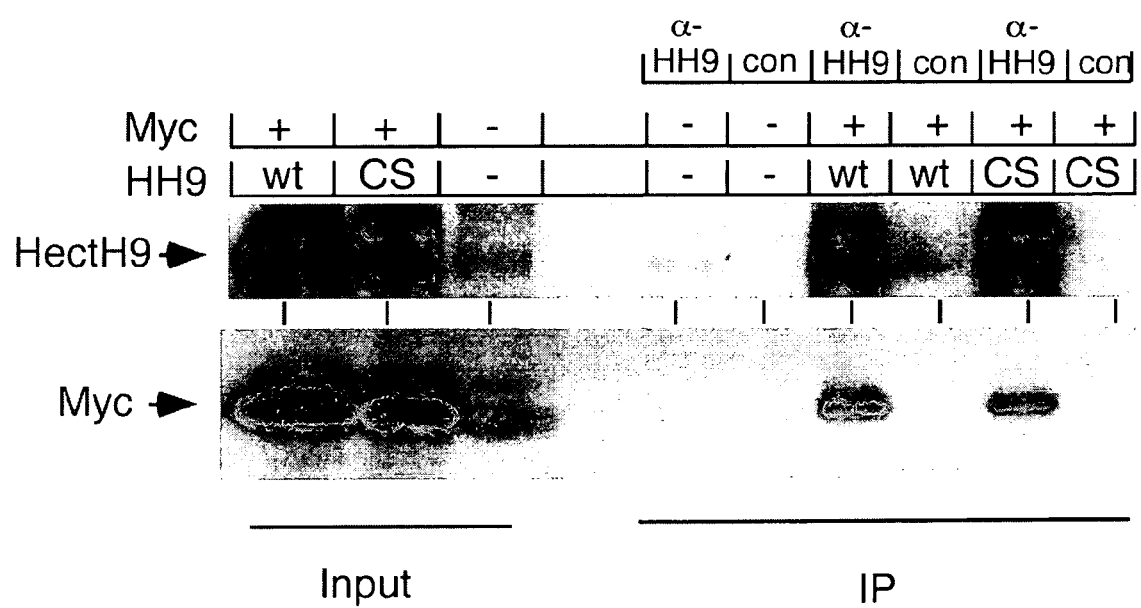
Figure 2A:
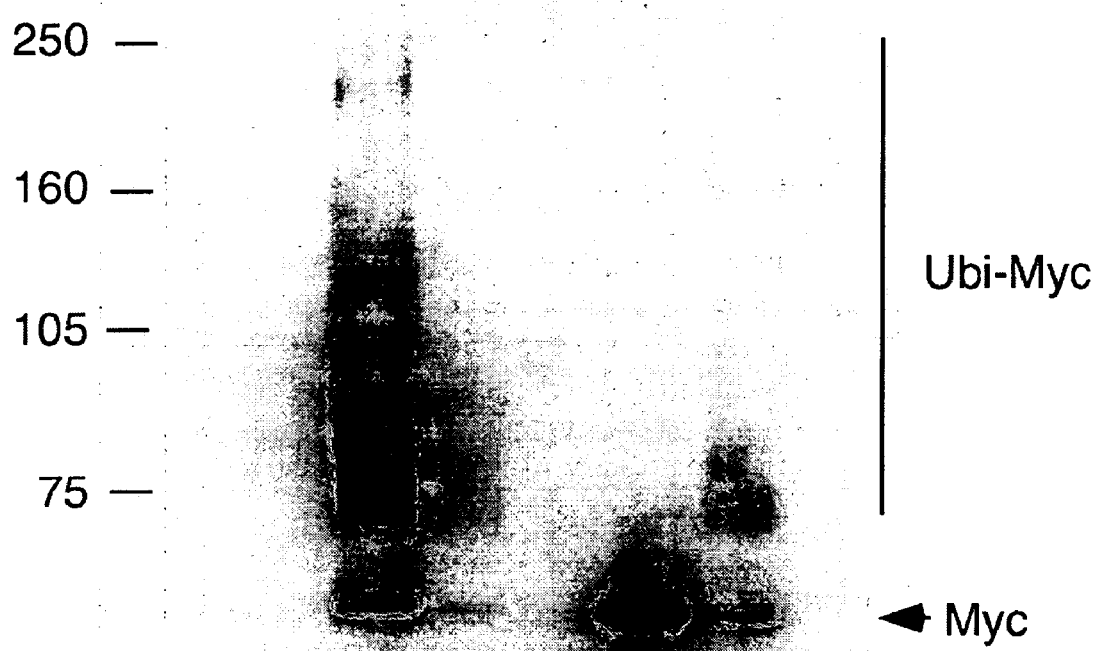
FIG. 2a-b shows the ubiquitination of Myc by HectH9
Figure 2B:
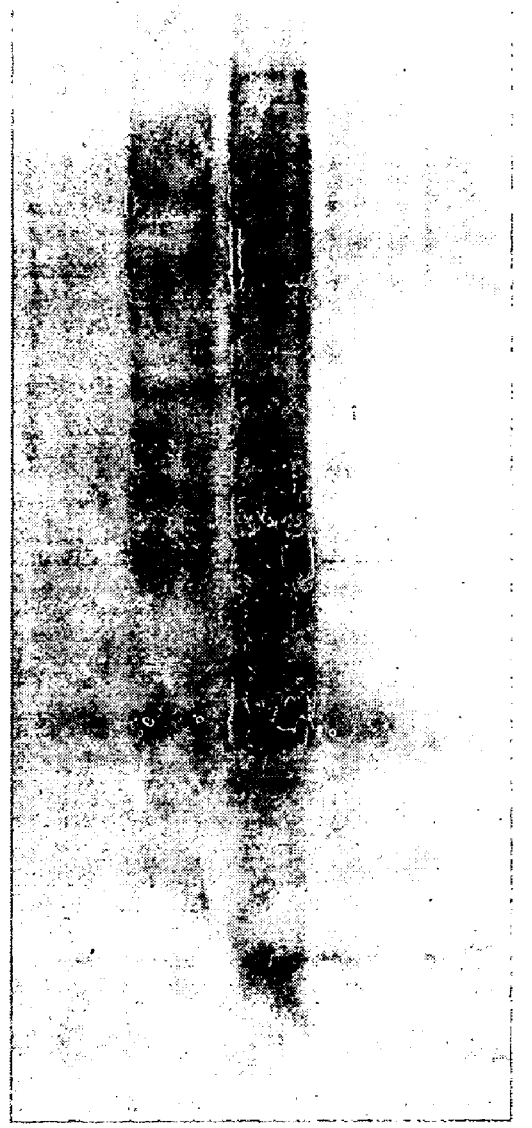

The present invention relates to a method for determining whether a compound has the potential to inhibit the activation of Myc, wherein a test compound's ability to interfere with the activity of the E3-ligase HectH9, which has the amino acid sequence shown in SEQ ID NO:2, or of a fragment or variant thereof that has E3-ligase activity, is determined, said HectH9 activity being selected from a) the transfer of ubiquitin from a ubiquitin conjugating enzyme E2 to HectH9, which has the amino acid sequence shown in SEQ ID NO:2, or a fragment or variant thereof that has E3-ligase activity; or b) the transfer of ubiquitin from HectH9 to Myc, and wherein a decrease in the level of HectH9 activity in the presence of the test compound, as compared to the level of HectH9 activity in the absence of the test compound, is indicative of the compound's potential to inhibit the activation of Myc.

DETAILED DESCRIPTION AND EMBODIMENTS OF THE INVENTION

In the following, the term "HectH9" or "HectH9 activity", respectively, encompasses HectH9 and variants and fragments thereof that have an E3-ligase activity similar to that of the naturally occurring HectH9 (SEQ ID NO:2), whereby "similar" means that such E3-ligase activity may be enhanced or decreased as compared to the naturally occurring HectH9. Since E3-ligase activity is determined by the HECT domain, it is essential that this domain, which contains the active site, is present.

For the present invention, the term "Myc" encompasses the HectH9 substrate c-Myc or any of its relatives that are activated in vivo by a ubiquitination reaction mediated by HectH9 (n-Myc or l-Myc). With regard to the method of the invention, "Myc" refers to a protein corresponding to the naturally occurring Myc protein or a fragment of variant thereof to which ubiquitin can be transferred in a quantifiable way.

In the embodiment a), the present invention relates to a method for identifying compounds that inhibit transfer of ubiquitin from a ubiquitin-conjugating enzyme E2 to HectH9, i.e. ubiquitination of HectH9. In this method, HectH9 is incubated, together with a ubiquitin activating enzyme (E1), a ubiquitin conjugating enzyme (E2), ubiquitin and ATP for a period of time sufficient to obtain a measurable level of ubiquitin associated with HectH9, and the level of ubiquitination of HectH9 in the presence or absence of a test compound is compared, and wherein a decrease in the level of HectH9 ubiquitination in the presence of the test compound, as compared to the level of HectH9 ubiquitination in the absence of the test compound, is indicative of the compound's ability to inhibit the activation of Myc.

The reaction that this embodiment of the invention is based on is a thioester formation between the active site cysteine of HectH9 and the terminal glycine of ubiquitin.

The components for this type of assay can be obtained as follows:

The proteins used in the method of the invention are preferably recombinant proteins, which can be obtained according to conventional methods by transforming a suitable host with a plasmid carrying the sequence encoding the protein. Alternatively, the recombinant proteins may be obtained by in vitro translation or coupled in vitro transcription/translations systems, which are commercially available, e.g. from Roche. The proteins obtained by such systems, optionally in already radioactively labeled form, may be used without further purification. In an embodiment of the invention, the substrate protein Myc is obtained by that method.

If the assay components, in particular HectH9, E1, E2 and/or ubiquitin, are produced recombinantly by expression in host cells, the host cells may, inter alia, be insect cells that are combined with the well-established baculovirus expression system, or bacterial cells, in particular *E. coli* cells. The cDNA sequences encoding the protein components are available from the literature and from databases:

The assay components HectH9, E2 and ubiquitin are usually produced and purified as fusion proteins. The proteins may be fused to an affinity tag, which is a protein suitable for affinity purification, such as gluthathion S-transferase (GST, Amersham Pharmacia), maltose binding protein (MBP, New England Biolabs), chitin binding domain (New England Biolabs), the myc-epitope (EQKLISEEDL) or the His(6) tag (Qiagen, Novagene). The fusion protein can be expressed, e.g. in *E. coli*, and purified according to standard protocols.

E1 may be produced and purified as the other assay components; advantageously it is purified due to its reversible interaction with ubiquitin according to known methods (e.g. Hatfield and Vierstra, 1990 and 1992). In the case of using untagged ubiquitin, a commercially available product (e.g. from Sigma, Fluka) may be used as this assay component.

In the method of the invention, preferably human HectH9 is used, whose DNA and protein sequences are readily available, as described above: GenBank Accession No. BAC06833 ("Lasu1"); GenBank Accession No. NP_113584 (full-length HectH9 protein, SEQ ID NO:2), GenBank Accession No. NM_031407 (DNA sequence encoding full-length HectH9, corresponding to SEQ ID NO:1).

The ubiquitin activating enzyme (E1) can be selected from a variety of E1 molecules; an example for a suitable E1 is the wheat UBAI E1 (GenBank Accession No. M55604), however, UBAI E1 from other species, e.g. from *Xenopus laevis* or human (GenBank Accession No. M58028) or from mouse (SwissProt P30138) may also be used. Other E1 molecules have been described in WO 01/75145; their suitability in the method of the invention can be easily tested in preliminary experiments by combining E1 candidates with the other assay components and testing the functionality of the E1 candidates in the desired assay format. E1 can be purified on a ubiquitin affinity matrix according to published procedures (e.g. Hatfield and Vierstra, 1990 and 1992).

Also, the ubiquitin conjugating enzyme (E2) can be selected from a variety of E2 molecules; an example is the human variant UBCH5b (GenBank Accession No. U39317), which has proven useful in the present invention, although, also in this case, UBCH5b homologues from other species, e.g. *Xenopus laevis*, may be employed. Alternatively, UBCH5a (GenBank Accession No. AAH05980) or UBCH5c (GenBank Accession No. AAH66917) can be used. Alternatively, ubiquitin conjugating enzymes different from UBCH5a, b or c can be used, as long as these enzymes support the transfer of ubiquitin to the HectH9 protein. Other E2 molecules have been described in WO 01/75145 the contents of which are incorporated herein; their suitability in the method of the invention can be easily tested in preliminary experiments, as described above for E1. Preferably, the ubiquitin conjugating enzyme E2 is fused to an affinity tag which is selected from the ones listed above as suitable for HectH9, but different from the tag chosen for HectH9. For example, in the case that GST-HectH9 is used, His(6) or another tag different from GST is used for tagging E2.

Preferably, the naturally occurring proteins are used as assay components; however, the proteins may contain deviations from the natural amino acid sequence as long as these deviations do not impair their functional activity.

Thus, the components used in the method of the invention may also be variants or fragments of the above-mentioned protein components, e.g. ubiquitin, E1, E2 and/or HectH9 variants or fragments. The variants may be substitutional, insertional or deletional variants that can be obtained by site specific mutagenesis of nucleotides in the DNA encoding the respective protein, e.g. using PCR mutagenesis or other techniques well known in the art, to produce DNA encoding the variant or fragment, and thereafter expressing it, As long as such variants or fragments exhibit the same biological activity as the naturally occurring protein, they are useful in the method of the invention. Variants or fragments that have modified characteristics, e.g. a stronger enzymatic activity, can also be used. In order to improve the performance of a protein with a mutation at a given site, random mutagenesis may be conducted at the target codon or region and the expressed variants screened for the optimal desired activity. Techniques for making substitution mutations at predetermined sites in well known, e.g. PCR mutagenesis.

Since the full-length HectH9 protein is 4374 amino acids long, it is advantageous to use a HectH9 fragment, which can be more readily produced in recombinant form. Essential for the suitability of a HectH9 fragment for use in the present invention is that it contains the HECT domain, i.e. the C-terminal region comprising a stretch of ca. C-terminal 350 amino acids. To verify that a pre-selected HectH9 variant, in particular a fragment, is useful for the method of the present invention, it can be tested in preliminary tests by measuring whether it associates with ubiquitin at the active cysteine site (in its non-mutated form) within the HECT domain, which results, in the absence of a substrate, in formation of a polyubiquitin chain, which, in certain embodiments of the invention, is measured. By way of example, a HectH9 fragment that has been shown to have HectH9 activity for the purpose of the present invention, comprises the C-terminal 638 amino acids of HectH9 (or LASU1, respectively).

To sustain a sufficient ATP level during the entire ubiquitination reaction, a so-called "ATP regenerating system" (e.g. comprising 0.5 mM ATP, 60 μg/ml creatine phosphokinase, 6.6 mM phosphocreatine, 10 mM Tris-HCl, 0.5 mM $MgCl_2$, 1 mM KCl, 0.05 mM DTT) may be advantageously employed (Murray, 1991), in particular in assays that employ in vitro-translated proteins. When the assay employs purified proteins, ATP may be present by itself.

By "ubiquitin" is meant a polypeptide which is ligated to another polypeptide by ubiquitin ligase enzymes. Ubiquitin is a highly conserved 76 amino acid protein expressed in all eukaryotic cells. The ubiquitin used in the method of the present invention can be from any species of organism, preferably a eukaryotic species. Preferably, the ubiquitin is mammalian, in particular human (SwissProt Accession No. $PO_{2248}$). Ubiquitin is commercially available (Sigma), it may also be recombinantly produced; in this case it may be fused to various tags for purification, i.e. His(6), GST or for detection, i.e. myc-epitope, HA-epitope. In both cases, ubiquitin comprises the 76 amino acids that are required for its function. Preferably, a tagged ubiquitin is employed in the assay. The ubiquitin used in the assay may also carry a non-proteinacious tag, e.g. biotin. Other suitable ubiquitin tags have been described in WO 01/75145 the contents of which are incorporated herein.

The above-described assay essentially comprises the steps of the ubiquitination reaction itself and the step of measuring the extent of ubiquitin transfer to HectH9.

The first step comprises reacting the assay compounds listed above for a period of time sufficient to allow for the ubiquitination reaction, e.g. for 30 min.

The reaction may either be conducted in solution by simply mixing the assay components, or alternatively, the reaction may be carried out by using immobilized HectH9. In this case, HectH9 carries an affinity tag (GST or one of the alternative tags mentioned above) that is used for its binding to a solid phase carrying the ligand for the respective affinity moiety, e.g. glutathione agarose or sepharose beads or microtiter plates coated with antibodies against the affinity moiety, e.g. commercially available anti-GST antibodies After the reaction has been completed, the extent of ubiquitin associated with HectH9 can be measured in different ways:

In case the ubiquitination reaction has been carried out in solution, the affinity-tagged, e.g. GST-tagged, HectH9 is captured on microtiter plates that are coated with an antibody against GST (this step can be omitted in case the reaction has been carried out with HectH9 bound to a solid phase). The unbound GST-HectH9, the unincorporated ubiquitin and the other reaction partners are then washed off. Subsequently, the immobilized ubiquitin can be visualized by using an antibody that is directed against a tag epitope, e.g. the myc-epitope present in the recombinant tagged ubiquitin, which antibody carries a detectable label. Suitable labels are well known in the art, they have, inter alia, been described in WO 01/75145 the contents of which are incorporated herein. Examples are radioactive labels, e.g. $^{125}I$, enzymatic labels, e.g. horseradish peroxidase or alkaline phosphatase, or fluorometric labels. In a preferred embodiment, quenched fluorophors, e.g. Europium (Delphia System by Perkin Elmer/Wallac) that will be dequenched upon incubation with an enhancer solution (Perkin Elmer/Wallac), are used.

The obtained values are compared to values obtained from reactions without HectH9 (negative control, background) and to values obtained from a reaction mixture incubated in the presence of the solvent (usually DMSO) only (positive control).

Alternatively to using the ELISA-type assay described above to detect the amount of bound ubiquitin, the physical proximity of ubiquitin molecules associated with HectH9 (in the case of measuring the ubiquitin transfer to HectH9) or to the HectH9 substrate (in the case of determining ubiquitination of a HectH9 substrate; see below) upon incubation at 37° C. can be used to measure the extent of ubiquitin association with HectH9 or its substrate by fluorescence resonance energy transfer (FRET, as described by Gershkovich et al., 1996, or by Matayoshi et al., 1990, or recently reviewed by Selvin, 2000). FRET can only be achieved if certain conditions are fulfilled, i.e. fluorophor pairs with overlapping emission and excitation wavelengths, like europium/allophycocyanin, europium/Cy5, europium/PE (all commercially available from Perkin Elmer/Wallac) and an minimal proximity of these fluorophors below 5-10 nM. These fluorophors can be added either bound to antibodies directed against the affinity label, e.g. GST, or the epitope, e.g. the myc epitope, or can be directly coupled to HectH9, HectH9 substrate or ubiquitin (custom service of Wallac). When coupled to antibodies, the fluorophors are added to the reaction after its completion. No further washing steps are necessary and signals (excitation at 340 nm and emission measurement at 665 nm in the case of the FRET pair allophycocyanin and europium) are measured after incubation at 4° C. for 30 min, allowing the binding of the antibodies and the subsequent energy transfer between the fluorophors. In case of direct labeling of reaction components, i.e. ubiquitin or HectH9, real time measurements can be performed allowing the detection of kinetic differences in the reaction.

In the alternative embodiment b), the invention relates to a method for determining whether a compound has the ability to inhibit the transfer of ubiquitin from HectH9 to Myc, i.e. ubiquitination mediated by HectH9. In this embodiment HectH9 is incubated, together with a ubiquitin activating enzyme (E1), a ubiquitin conjugating enzyme (E2), ubiquitin, ATP and a HectH9 substrate protein (Myc) for a period of time sufficient to obtain a measurable level of ubiquitination of the substrate protein Myc and comparing the level of ubiquitination of Myc in the presence or absence of a test compound, wherein a decrease in the level of Myc ubiquitination in the presence of the test compound, as compared to the level of Myc ubiquitination in the absence of the test compound, is indicative of the compound's ability to inhibit the activation of Myc.

This embodiment is based on the observation obtained in the experiments of the invention that HectH9 is able to ubiquitinate substrate proteins, but not substrate proteins that have mutations at positions necessary for the attachment of ubiquitin.

In a preferred embodiment, Myc is the c-Myc oncoprotein.

With regard to the assay components and the reaction conditions, the features described for embodiment a), i.e. the assay based on transfer of ubiquitin to HectH9, also apply to embodiment b), i.e. the assay based on substrate (Myc) ubiquitination. These features refer both to assay components and their production as well as assays and the reaction conditions.

The substrate protein and DNA sequences are known from the literature and from data bases, e.g. c-Myc (Watt et al., 1983, GenBank Accession No. P01106), l-myc (GenBank Accession No. AA038672) or n-myc (Kohl et al., 1986, GenBank Accession No. $PO_{4198}$). Instead of using the full-length Myc protein, a C-terminal fragment that contains, as a minimum requirement, a relevant site for ubiquitination by HectH9 can be used. With respect to c-Myc, it has been shown in the experiments of the invention that the region from lysine 298 to lysine 355 is critical for ubiquitination. This means that at least one of the lysine residues in this region needs to be present, e.g. on a polypeptide encompassing approximately the region from lysine 298 to lysine 355. The size of the fragment may vary and can be easily determined in preliminary experiments by employing different sized Myc peptide fragments in the intended assay format and determining and selecting suitable (poly)peptides.

In the embodiment b) that uses the HectH9 substrate protein Myc, the substrate protein is captured by virtue of a tag, e.g. MBP, and the amount of associated ubiquitin is quantified in the presence or absence of test compounds.

Preferably, the method of the invention is in the form of a screening method in the high throughput format. By way of example, such a screening assay is performed in 96 or 384 well plates in a suitable reaction volume, e.g. 50 µl, in the presence or absence of the test compounds. The test compounds are usually dissolved in DMSO. In such a screening method, a test compound from a compound pool, e.g. from a chemical library, including combinatorial libraries, is applied to each well of an assay plate. Compounds that exhibit the desired properties, i.e. inhibit HectH9 activity, are hits that will be further evaluated.

Compounds identified as positive hits in the above-described primary screening assays according to embodiment a) and/or b) are next confirmed to be specific inhibitors of HectH9 activity and not to be inhibitors of any of the other enzymes present in the reaction mixture.

Compounds possibly obtained as unspecific ("false") hits are inhibitors of ubiquitin activating enzyme (E1) and ubiquitin conjugating enzyme (E2). E1 is necessary to activate ubiquitin for the subsequent reaction, as it is the only enzyme that is able to recognize free ubiquitin in solution. E1 forms a thioester with ubiquitin in an ATP-dependent manner and transfers this now activated ubiquitin molecule to an E2 enzyme, where another thioester between E2 and ubiquitin is formed. The thioester formation of E2 with ubiquitin is strictly dependent on the presence of E1, which means that E2 alone is unable to form a thioester with free ubiquitin. Compounds that inhibit any step in this cascade, i.e. compounds that interfere with the ATP binding to E1 or that prevent the formation of the thioesters between ubiquitin and E1 or ubiquitin and E2 like any reducing agent will subsequently inhibit the formation of multiubiquitin chains and appear as positive hits. The ATP-dependent thioester formation can be used to identify such false hits, i.e. compounds that inhibit this first step in the formation of multiubiquitin chains. Assays that are able to measure thioester formation and can thus be used in a secondary assay to exclude false hits, are known in the literature (Yu, et al., 1996). In brief, they are based on using the nature of a thioester with regard to reducibility by agents like dithiothreitol or β-mercapto ethanol. A mixture of E1, E2, ATP and ubiquitin is incubated at 37° C. in the presence of the compounds identified to inhibit the transfer of ubiquitin to HectH9 or DMSO as control. These samples are subsequently subjected to SDS-PAGE under non-reducing conditions; i.e. thioesters that have formed will not be broken up and transferred to PVDF or nitrocellulose membranes. Ubiquitin can be detected either by using monoclonal antibodies against ubiquitin (commercially available, e.g. from Santa Cruz) or by using and detecting tagged versions of ubiquitin (GST-ubiquitin, anti-GST antibodies; 3-9×myc-ubiquitin, 9E10 antibodies). In control reactions, free ubiquitin can be detected as well as ubiquitin associated with an approx. 20 kDa protein (E2) and an approximately 120 kDa protein (E1). Reduction or disappearance of these thioesters upon incubation with inhibitory compounds can be taken as indication for inactivation of either E1 or E2 or both and considered as unspecific.

Advantageously, a further secondary assay may be performed to confirm that the compounds identified in the assays of the invention are inhibitors specific for a HectH9-mediated ubiquitination reaction and not inhibitors of reactions mediated by other HECT domain containing proteins. Such (one or more) assay(s) use one or more other HECT domain containing protein(s), e.g. NEDD4 (GenBank Accession No. P46934), SMURFI (GenBank Accession No. Q9HCE7) or ITCHY (GenBank Accession No. Q96J02).

Alternatively, the activity of Myc can be inhibited by preventing the interaction of the transcriptional co-activator p300 and the ubiquitinated Myc or a variant or fragment thereof. A screening assay based on this principle is a protein-protein interaction assay, in which one of the interaction partners is usually bound to a solid support and binding of the other partner, which may carry a detectable epitope tag, is quantified. A compound that interferes with binding of the two proteins is a candidate for reduction of Myc activation.

Compounds identified in the screening methods of the invention, which function as inhibitors of HectH9 activity, are expected to completely or partially inhibit proliferation of tumor cells; this effect is expected to subsequently induce apoptotic cell death. Due to this ability, such compounds are drug candidates for the therapy of cancer.

To test the ability of a candidate compound to inhibit tumor cell proliferation, primary human tumor cells or various different human cell lines (e.g. the colon cancer cell line HCT116 or the breast cancer cell line MCF7) are incubated with the candidate compound identified by the method of the invention and the inhibition of tumor cell proliferation is tested by conventional methods, e.g. bromodesoxyuridine or $^3$H incorporation, Alamar BLUE. Compounds that exhibit an anti-proliferative effect in these assays may be further tested in tumor animal models and used for the therapy of tumors.

Animal models useful for testing these compounds include those described above (Felsher and Bishop, 1999; Jain et al., 2002; Pelengaris et al., 1999; Pelengaris et al., 2002a) that exhibit Myc-dependent tumorigenesis. Moreover, xenograft models of human cancer cell lines containing elevated and/or deregulated Myc, such as breast, colon, cervical, small cell lung carcinomas, osteosarcomas, glioblastomas, melanoma and myeloid leukemias, can be used to test the efficacy of such compounds.

Toxicity and therapeutic efficacy of the compounds identified as drug candidates can be determined by standard pharmaceutical procedures, which include conducting cell culture and animal experiments to determine the $IC_{50}$, $LD_{50}$, $ED_{50}$. The data obtained are used for determining the human dose range, which will also depend on the dosage form (tablets, capsules, aerosol sprays, ampules, etc.) and the administration route (oral, buccal, nasal, paterental or rectal). A pharmaceutical composition containing the compound as the active ingredient can be formulated in conventional manner using one or more physiologically active carriers and excipients. Methods for making such formulations can be found in manuals, e.g. "Remington Pharmaceutical Sciences".

The following Examples are provided to show how the invention can be practices they are not intended to limit the invention in any way. In the following Examples, if not otherwise stated, the following materials and methods were used:

Protein Interaction

To generate the bait plasmid, the POZ domain of Miz-1 (amino acids 1-117) was amplified by PCR and inserted into pGBT9 (Clontech). A total of 1×10$^6$ independent transformants of a human HeLa cDNA library fused to the GAL4 activation domain (Matchmaker, Clontech) were screened. In vitro transcription/translation was carried out in reticulocyte lysate (Promega) in the presence of [S$^{35}$]-methionine. The translated product were mixed and incubated for 90 min at 4° C. Immunoprecipitation was carried out using the indicated antibodies immobilized on protein G-sepharose beads. The beads were washed four times in 20 mM HEPES pH 7.8, 100 mM KCl, 5 mM MgCl$_2$, 0.5 mM DTT, 0.5% Igepal CA-630. Bound proteins were analyzed by SDS-gel electrophoresis and fluorography.

Cell Culture

HeLa cells were grown in DMEM supplemented with 10% heat-inactivated FCS, 2 mM L-glutamine, 100 U/ml penicillin and 100 µg/ml streptomycin. Recombinant retroviruses were generated and used as described (Peukert et al., 1997). Infected cells were selected and analyzed within 2 passages after selection.

Transfections and Expression Analysis

All transient transfection experiments were carried out using a standard CaPO$_4$-protocol. The prothyinosina-reporter plasmids have been described in (Desbarats et al., 1996). CMV-based expression plasmids encoding Myc, Miz1 and ΔPOZMiz1 have been described (Herold et al., 2002). Point mutants were introduced into Myc using the Quick-exchange kit from Stratagene. Expression plasmids encoding his-tagged ubiquitin and ubiquitin-mutants were a kind gift of Martin Scheffner (University of Cologne). A full-length cDNA encoding HectH9 was inserted into pcDNA3 (Invitrogen) to generate CMV-HectH9 (kind gift of Kristian Helin). pSUPER plasmids were a kind gift of Rene Bemards (Brummelkamp et al., 2002).

Antibodies

Immunofluorescence and immunoprecipitation was carried out as described previously (Staller et al., 2001). The following antibodies were used: Miz1: Monoclonal antibody 10E2; Myc: 9E10 (Evan et al., 1985) and N262 (Santa Cruz); HectH9: affinity-purified polyclonal antiserum against the carboxyl-terminus and monoclonal antibody Ax8D 1 (Kind gift of Kristian Helin).

Chromatin Immunoprecipitation (ChIP)

ChIP assays were performed as described previously (Bouchard et al., 2001) using the following antibodies: anti-Myc (N-262; sc-764), anti-p300 and control antibody. Immunoprecipitated DNA samples were amplified by real-time PCR (ABI-Prism) using a Eurogentech Cybr-Green Core kit and primers specific for the E-boxes of the indicated genes. Primer sequences are available upon request.

EXAMPLE 1

Two-Hybrid Screen for Identifying Novel Interaction Partners of Miz1.

Interaction of Myc and Miz 1 with HectH9

Figure 3A:
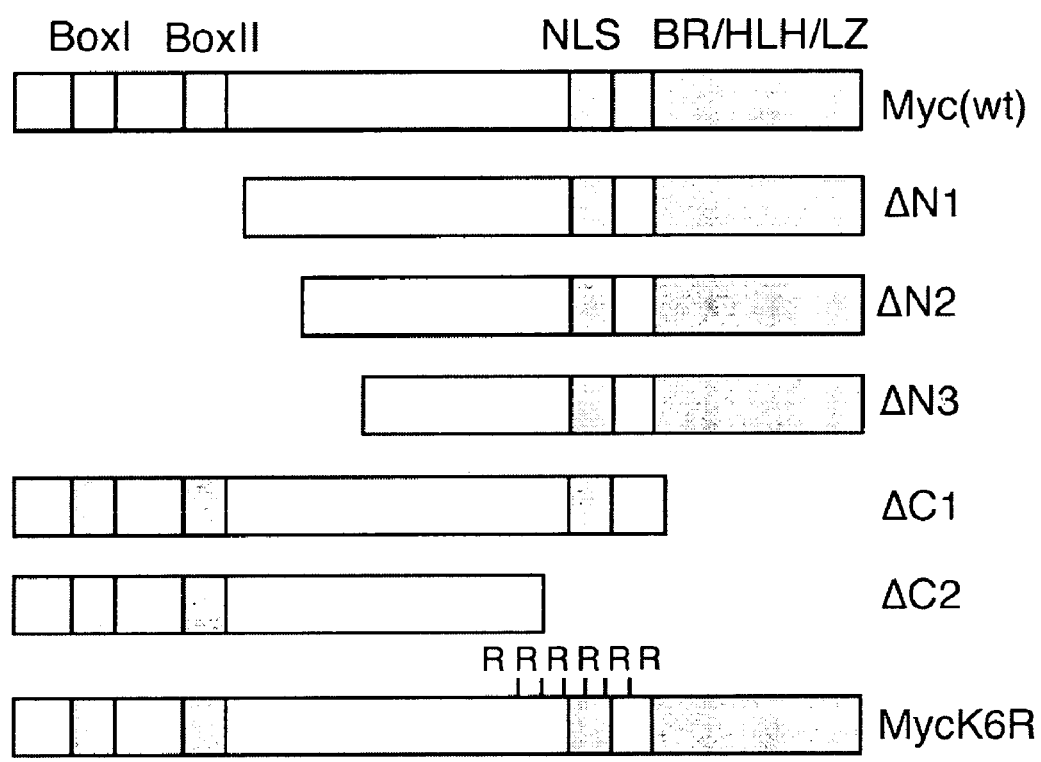
FIG. 3a, 3b1, 3b2, 3c and 3d show HectH9 targets lysines in the carboxyl-terminus of Myc
Figures 1, 3B:
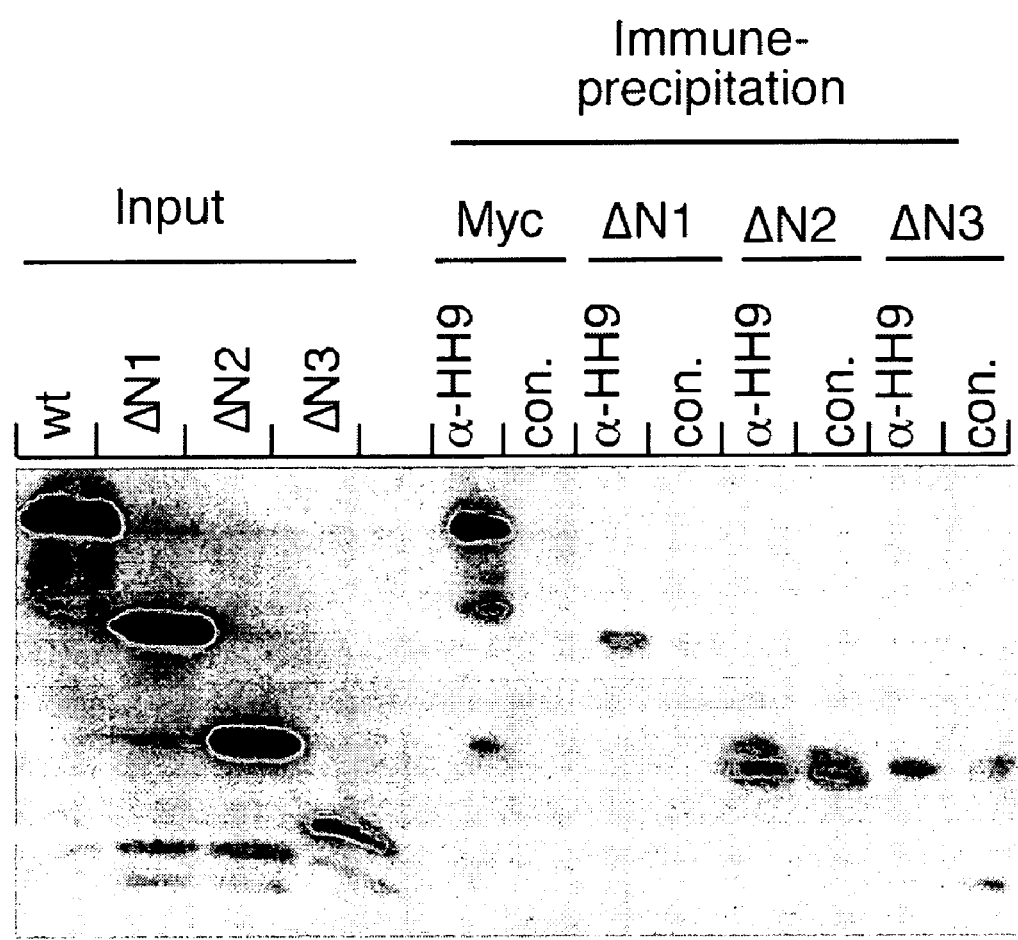

The results of the experiments are shown in FIG. 1:

Panel a: The schematic diagram shows the carboxyl-terminal catalytic domain ("HECT"), two putative nuclear localization signals ("NLS"), a leucine zipper ("LZ") and an UBA and a WWE domain. The sequence corresponding to the clones recovered in the two hybrid screens is underlined.

Panel b shows the in vitro interaction of HectH9 and Miz1. Miz1, ΔPOZMiz1 and Myc were translated in a reticulocyte lysate in the presence of $^{35}$S-methionine; after synthesis, the lysates containing the proteins indicated at the top were mixed and precipitated with the indicated antibodies. Shown is an autoradiogram of the precipitates; the input corresponds to 20% of the synthesized proteins.

Panel c shows that HectH9 is a nuclear protein. Shown are immunofluorescence pictures of HeLa cells stained with a polyclonal antiserum against HectH9. The top panel shows HeLa cells stably transfected with empty pSUPER; the bottom panel shows HeLa cell transfected with pSUPER-HectH9.

Panel d shows the in vivo interaction of HectH9 and Myc. HeLa cells were transiently transfected with expression plasmids encoding the indicated proteins. The lanes at the left show the input controls. The lanes on the right show the immunoprecipitates using the indicated antibodies. The top panel was probed with antibodies against HectH9, the bottom panel probed with antibodies against Myc.

Panel e shows that in vivo interaction of HectH9 and Miz1 depends on the POZ domain. The experiment was carried out as in panel d, except that Miz1 or ΔPOZMiz1 were co-expressed with HectH9. The blot was probed with antibodies against Miz1.

EXAMPLE 2

Analysis of whether HectH9 Ubiquitinates Miz 1 or Myc

HeLa cells were transfected with expression plasmids encoding the indicated proteins. Lysates were precipitated with Ni-agarose and the precipitates probed with antibodies against Myc.

Figures 2, 3B:
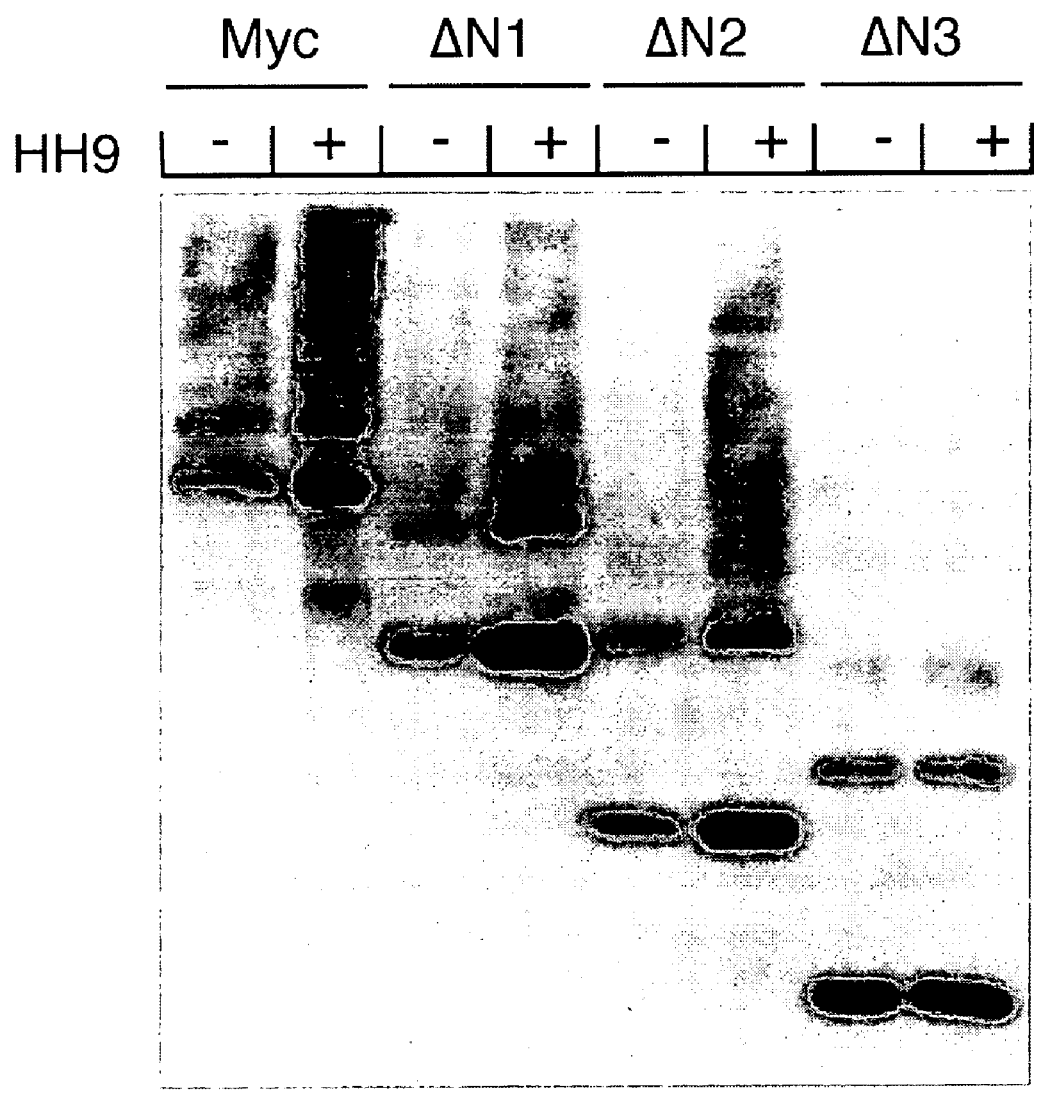
Figure 3C:
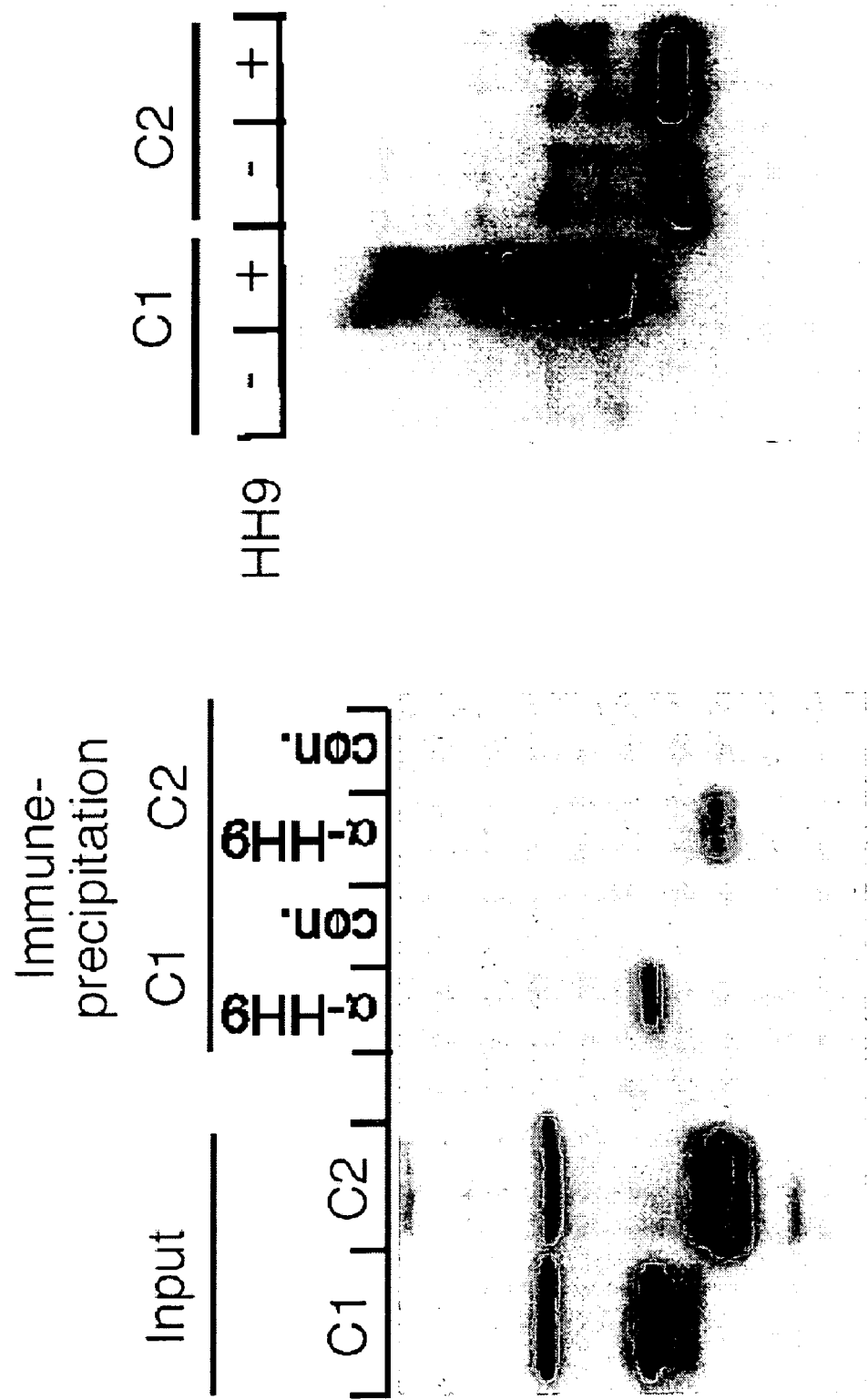
Figure 3D:
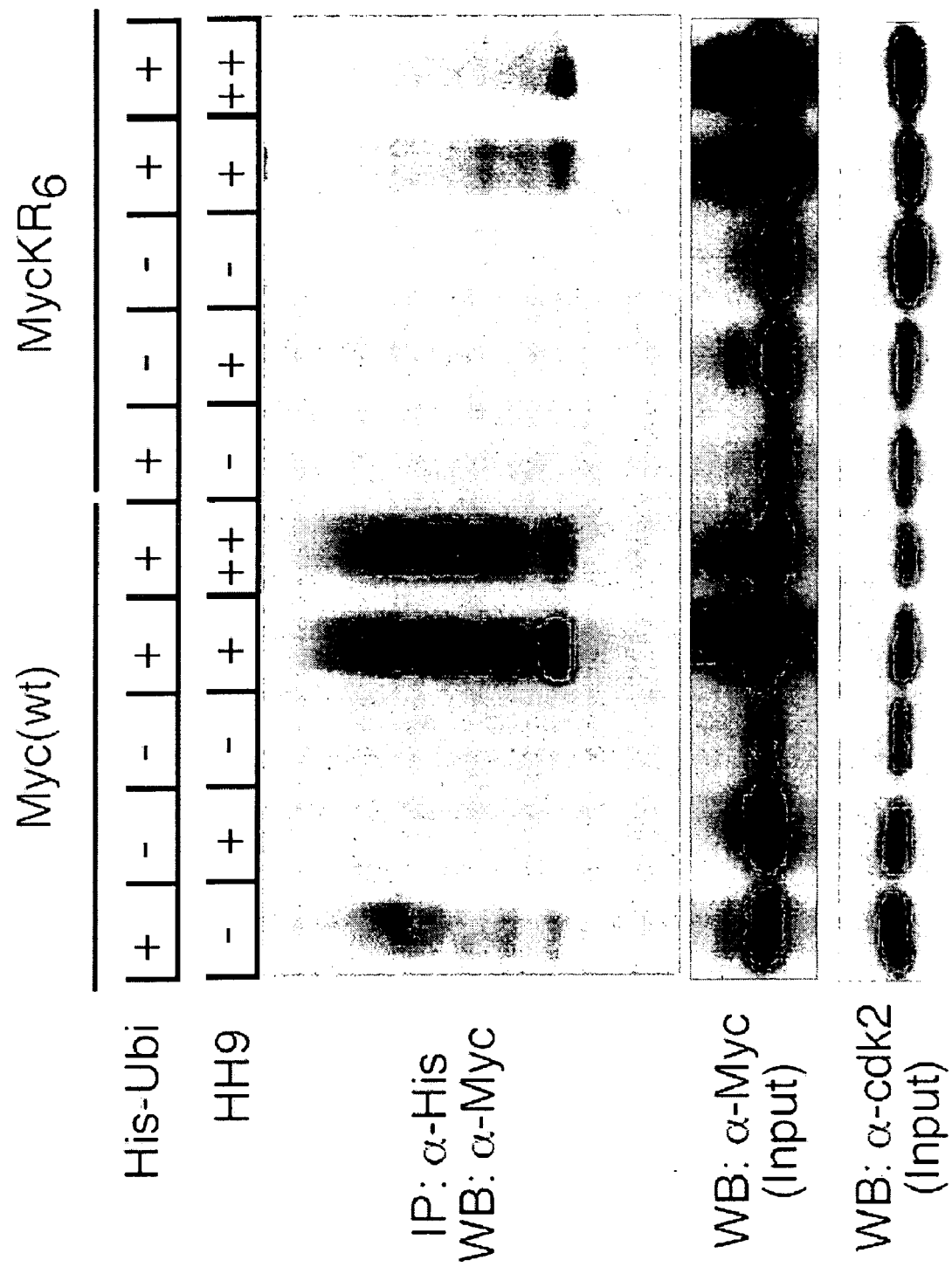

FIG. 2 shows that it is Myc that is ubiquitinated by HectH9.

EXAMPLE 3

Analysis of the Functional Consequences of HectH9-Mediated Ubiquitination of Myc To test the functional consequences of HectH9-mediated ubiquitination of Myc, the lysine residues in Myc that are targeted by HectH9 were mapped. It was found that HectH9 targets lysines in the carboxyl-terminus of Myc. The findings of these experiments are shown in detail in FIG. 3.

Panel a is a schematic drawing of the Myc mutants used in these experiments. Two conserved "Mycboxes" and the carboxyl-terminal BR/HLH/LZ-domain are shown. NLS indicates the nuclear localization signal.

Panel b shows the analysis of N-terminally truncated mutants of Myc. Top: HeLa cells were transfected with expression plasmids encoding HectH9 and the indicated mutants of Myc. Lysates were immunoprecipitated with the indicated antibodies and the precipitates probed with an α-Myc antibody (9E10, which recognizes an epitope in the carboxyl-terminus of Myc). Bottom: HeLa cells were transfected with expression plasmids encoding His-tagged ubiquitin, HectH9 (where indicated) and the indicated mutants of Myc. Lysates were precipitated with Ni-agarose and the precipitates probed with anti-Myc antibodies.

Panel c shows the binding and ubiquitination of carboxyl-terminal mutants of Myc by HectH9. The experiment was carried out as in "b", except that a different antibody (N262 raised against the amino-terminal 262 amino acids of Myc) was used to detect Myc proteins.

Panel d shows that a mutant of Myc that has six lysines replaced by arginine (MycKR$_6$) has reduced basal and HectH9-mediated ubiquitination.

The experiment was carried out as in panels b and c. The top panel shows Ni-agarose precipitates of lysates of transfected cells, which were probed with an antibody directed against Myc. The lower panels show immunoblots of aliquots of the transfected cells with α-Myc and α-Cdk2 antibodies showing equal expression of Myc and MycKR$_6$ after transfection.

EXAMPLE 4

Testing whether ubiquitination triggers degradation of Myc

Figure 4A:
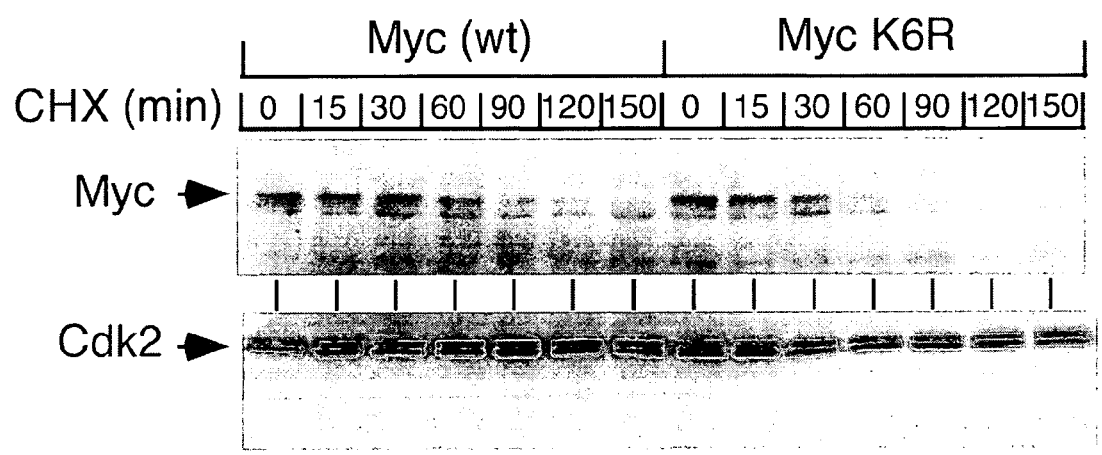
FIG. 4a-c shows that HectH9 mediates lysine-63 linked poly-ubiquitination of Myc
Figure 4B:
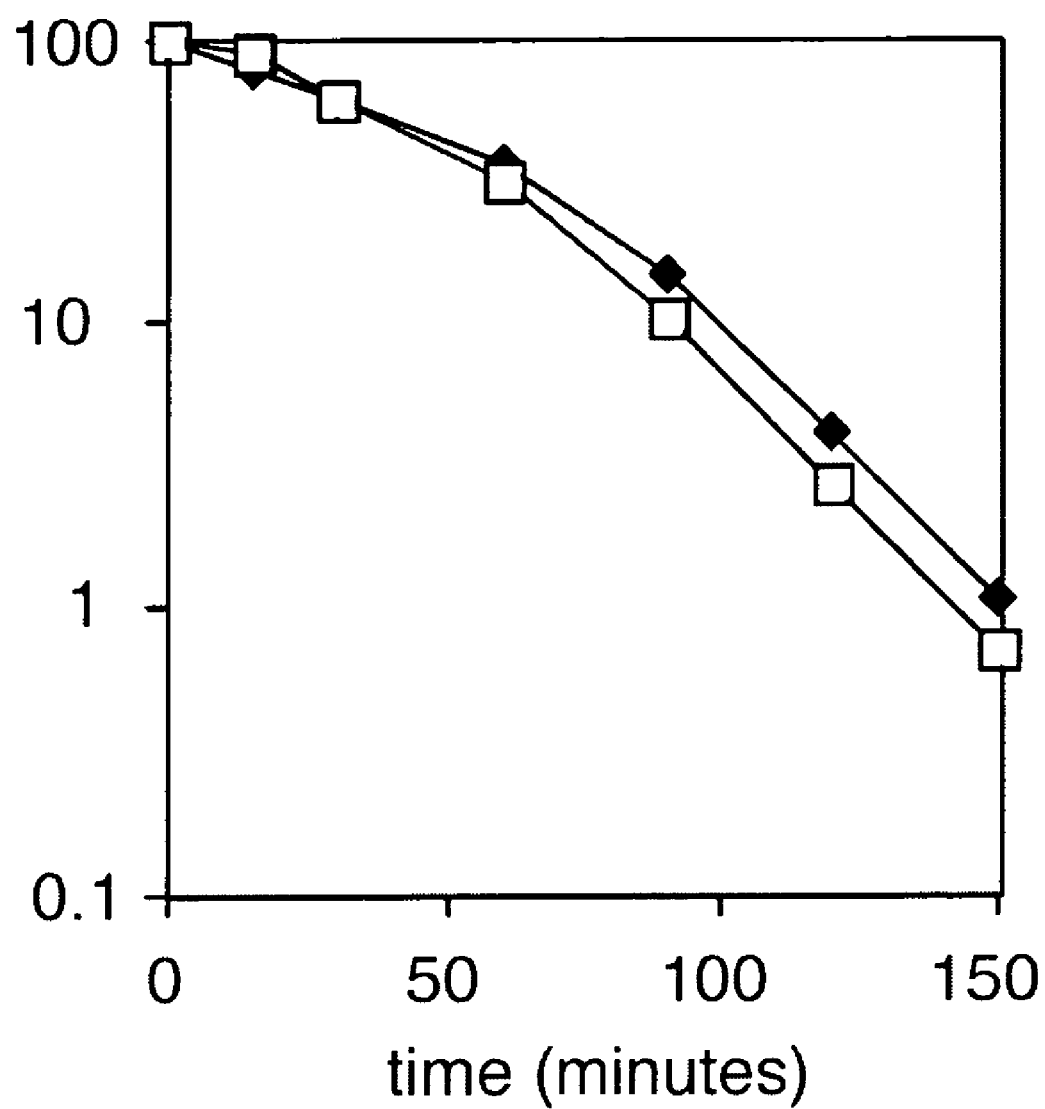
Figure 4C:
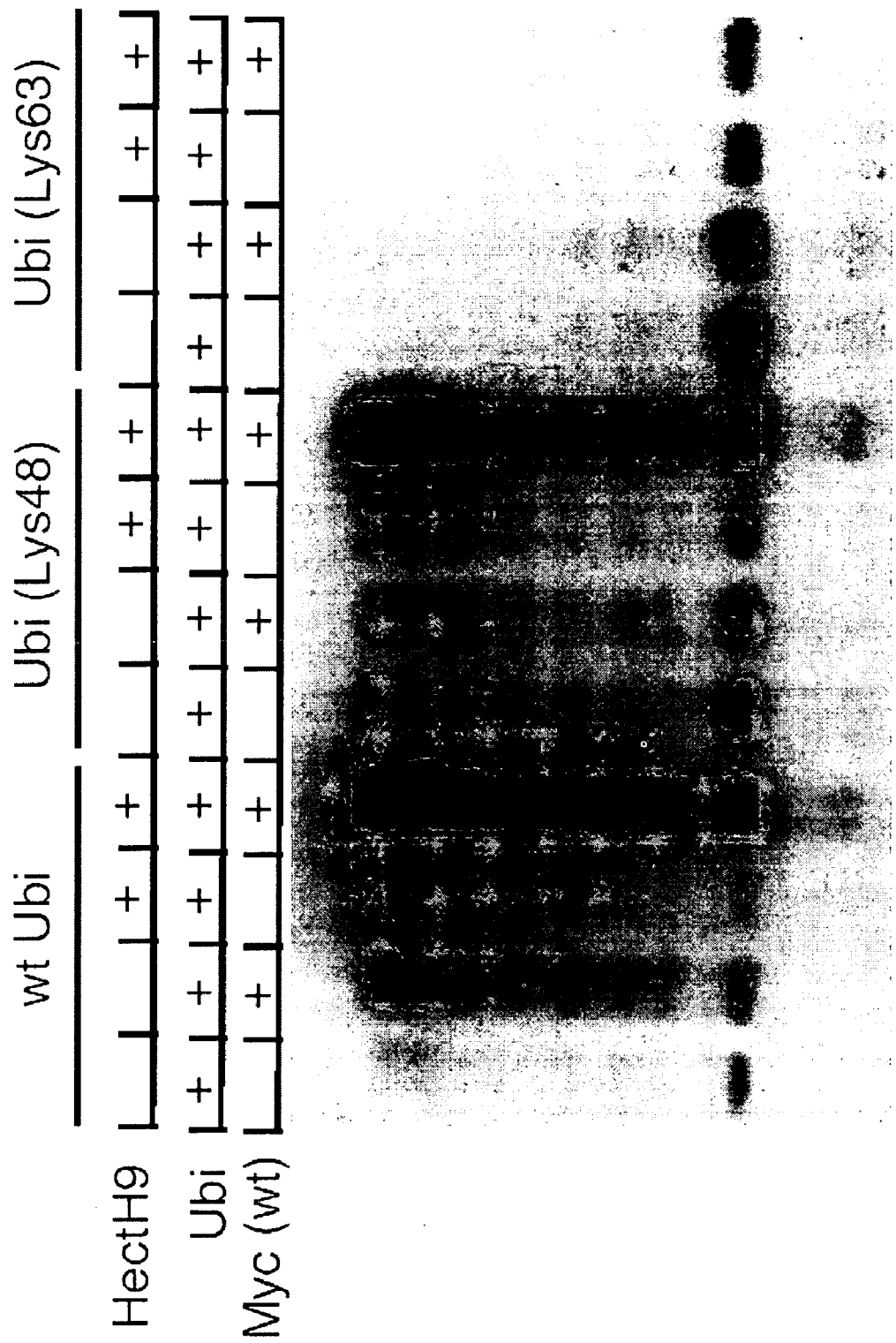
Figure 5A:
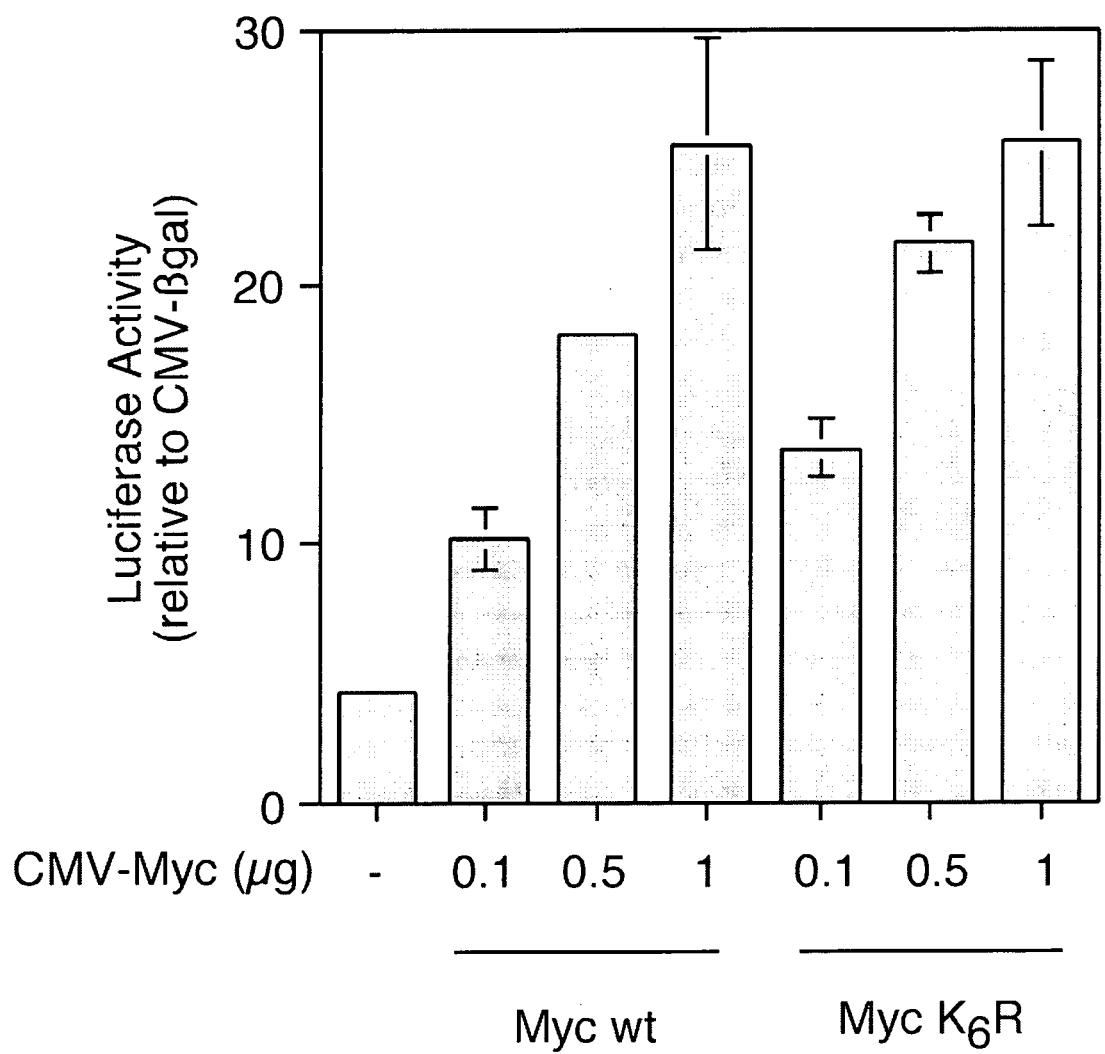
FIG. 5a-d shows transcriptional properties of Myc and MycKR
Figure 5B:
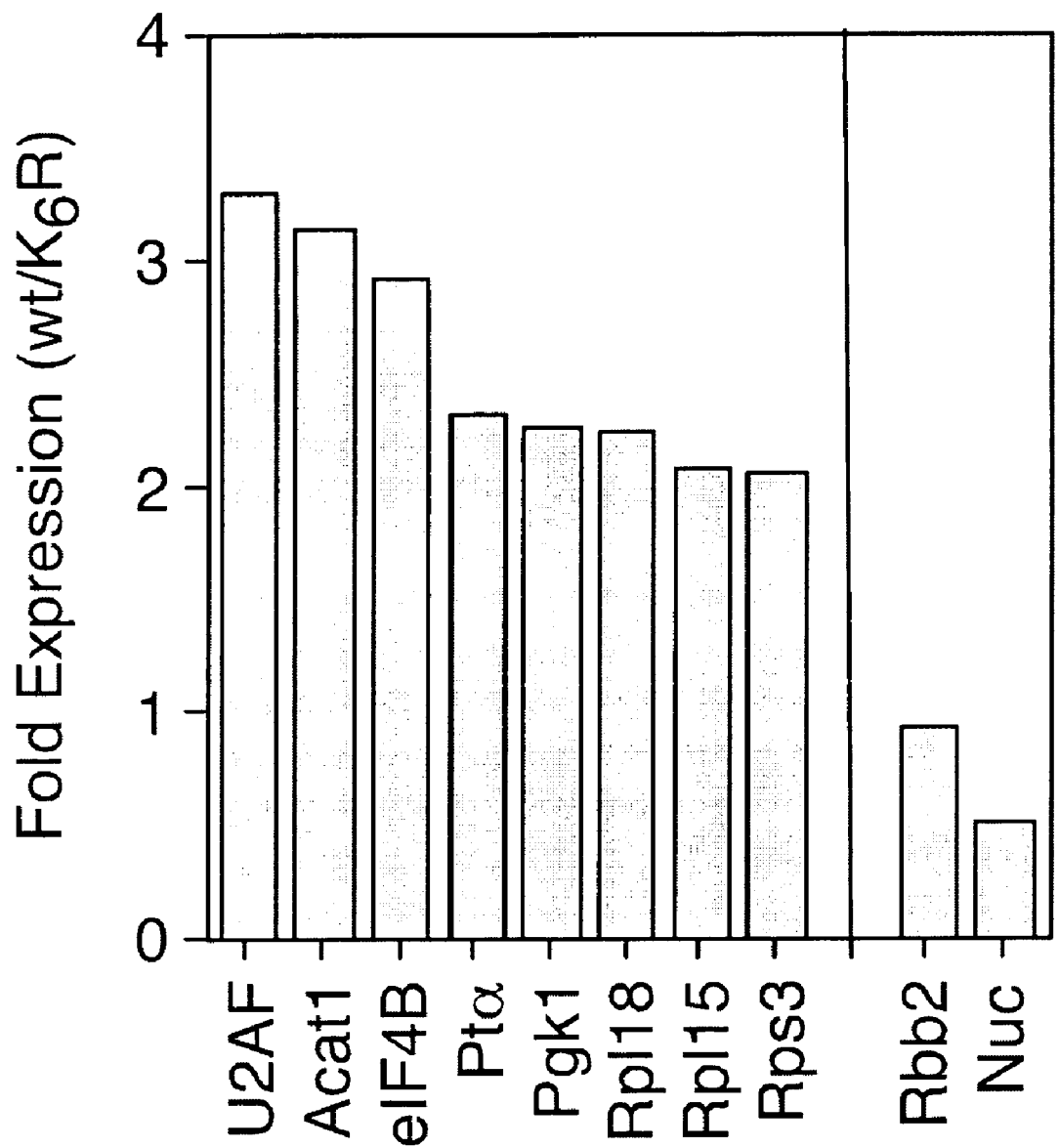
Figure 5C:
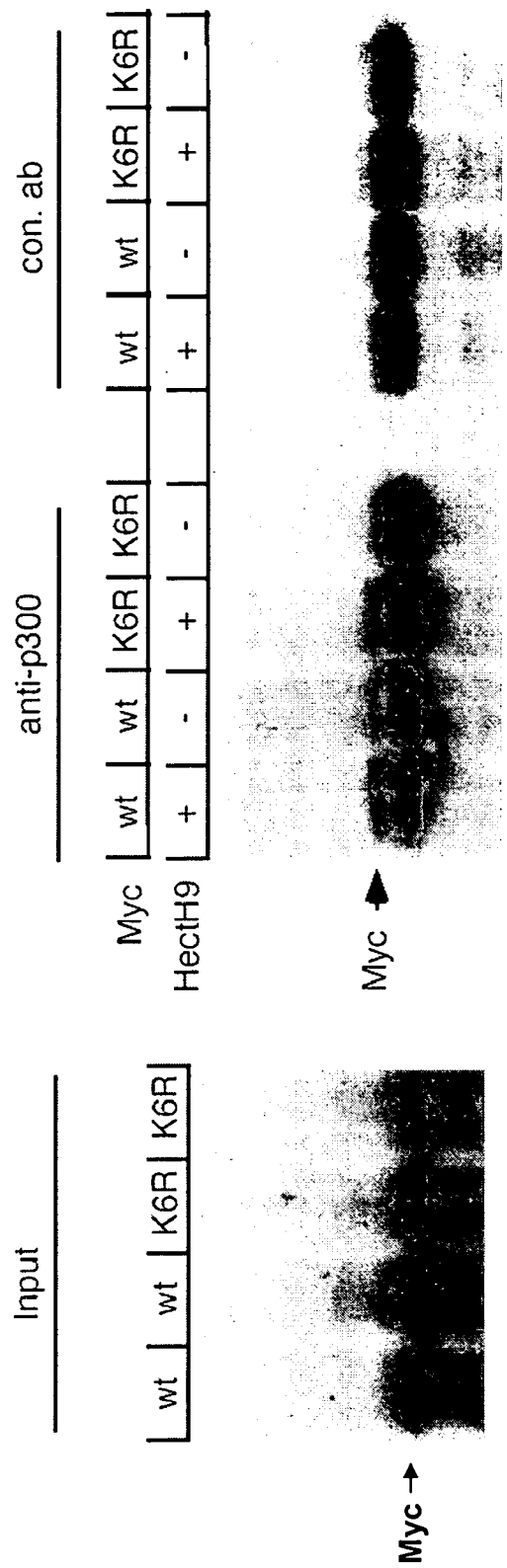
Figure 5D:
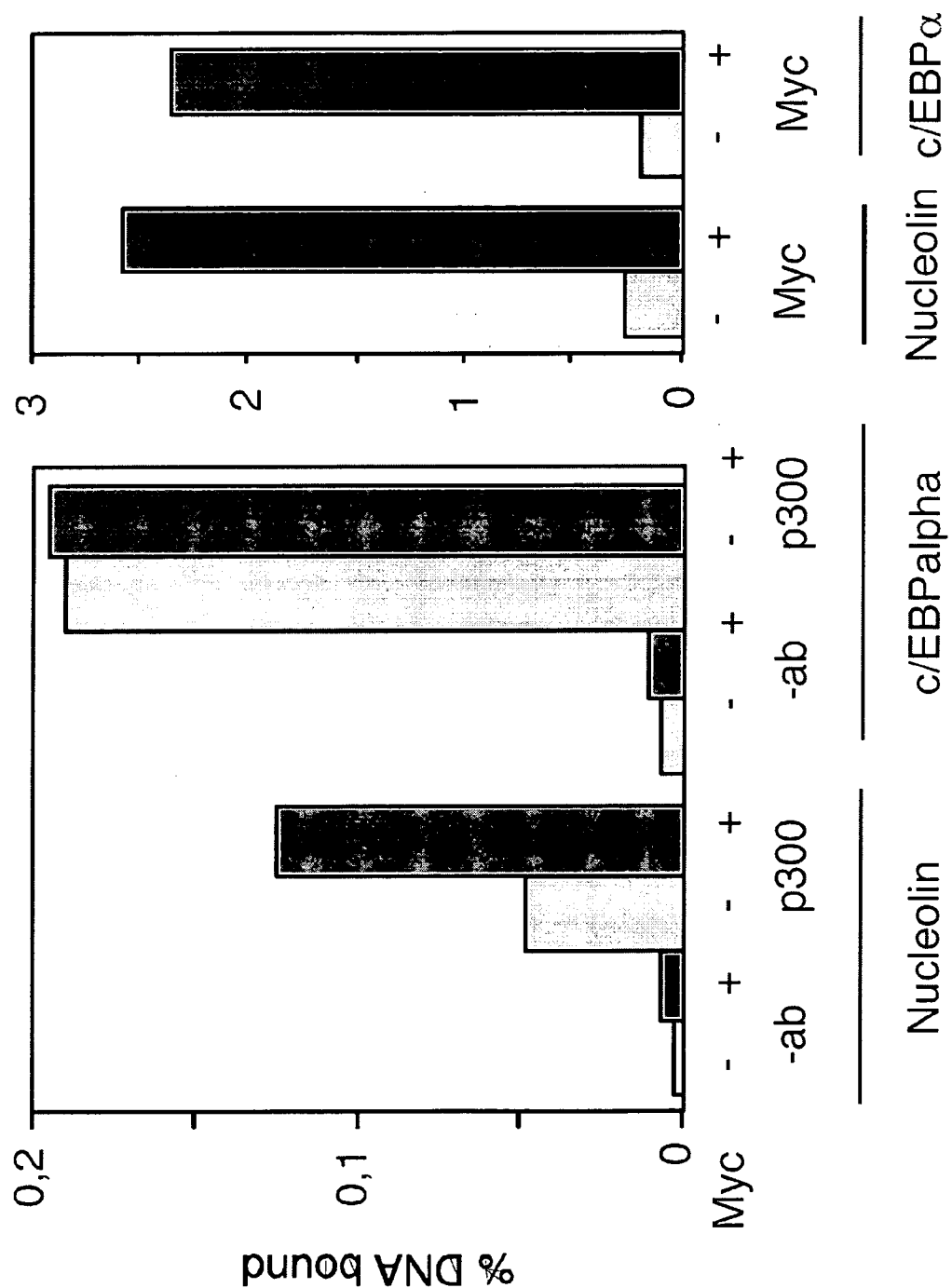
Figure 6:
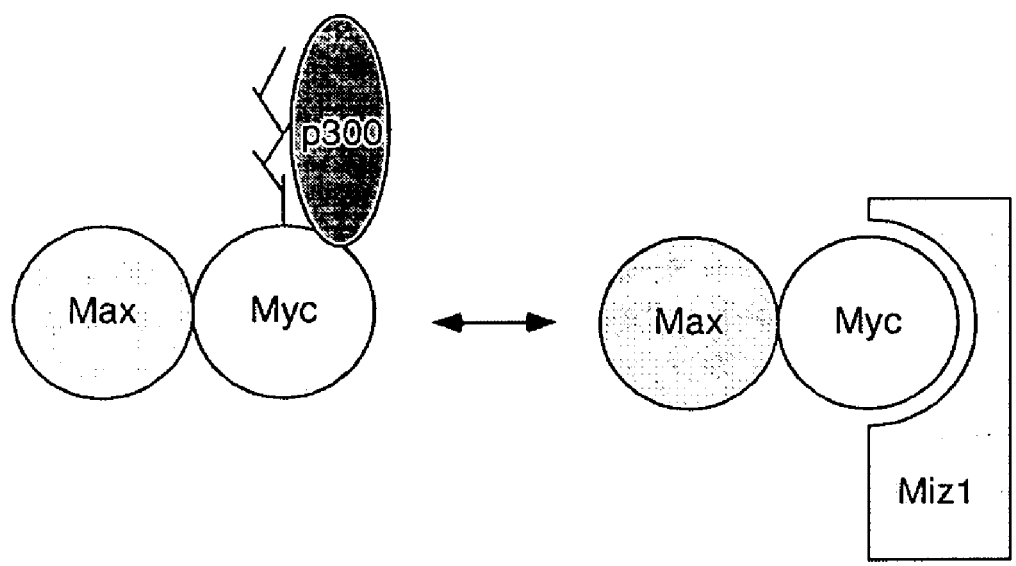
FIG. 6 shows a model of Myc activation and Myc repression.

The results of the experiments, which show that HectH9 mediates lysine-63 linked poly-ubiquitination of Myc, is depicted in FIG. 4:

Panel a shows unaltered stability of Myc and MycKR$_6$. NIH3T3 cells were infected with retroviruses expressing either Myc or MycKR$_6$ Cells were treated with cycloheximide for the indicated times and lysates were probed with antibody 9E 10, which is specific for human Myc.

Panel b presents the quantitation of the results show in panel a.

Panel c: Ubiquitination of Myc by HectH9 was carried out as in FIG. 2 in the presence of wither wild-type ubiquitin or the ubiquitin mutants in which the indicated residue is replaced by an arginine.

EXAMPLE 5

Testing how ubiquitination affects the function of Myc

The transcriptional properties of Myc and MycKR$_6$, obtained as a result of the transient reporter assays, are shown in FIG. 5:

Panel a: Transient transfection assays with the indicated amounts of expression plasmids for either Myc or MycKR$_6$ in HeLa cells using an E-box reporter plasmid derived from the prothymosin-a gene, a target of Myc.

Panel b: Relative expression levels of endogenous Myc target genes. NIH3T3 cells were infected with retroviruses expressing either Myc or MycKR$_6$ and serum-starved for 48 hours to deplete the endogenous Myc proteins. RNA was isolated and subjected to microarray analysis using an 11.5 kcDNA array. Shown are relative expression levels of selected direct target genes of Myc. The values show the fold expression in cells expressing wild type Myc relative to cells expressing MycKR$_6$.

Panel c: HectH9 stimulates binding of Myc to p300. HeLa cells were transfected with expression plasmids encoding HA-tagged p300, Myc or MycKR$_6$ and HectH9 where indicated. Lysates were precipitated with a-HA antibody and probed with antibodies directed against Myc. The left panel shows an input control.

Panel d: Myc recruits p300 selectively to E-Boxes, not to Miz1 binding sites in vivo. Shown are chromatin-immuno-precipitation (Chip) experiments with the indicated antibodies from a B-cell line harboring a tetracyclin-regulatable Myc gene. Chips were carried out either in the presence or absence of Myc with the indicated antibodies. The percentage DNA bound was calculated from real-time PCR amplifying the precipitates with primers for the indicated genes.

EXAMPLE 6

Screening assay in high throughput format for determining the transfer of ubiquitin to HectH9

The proteins used in the following example are obtained by recombinant expression in suitable host cells, i.e. *E. coli* JM 109, and purified by virtue of their fusion to an affinity tag.

In a 384 well amylase-coated microtiter plate (Pierce), an enzyme mixture containing 1 ng his-tagged UBAI (E1), 30 ng his-tagged UBCH5 (E2), 50 ng MBP-HectH9, consisting of the C-terminal 638 amino acids of HectH9, and 100 ng GST-ubiquitin are mixed in reaction buffer (20 mM Tris/HCl pH 7.5, 150 mM NaCl, 2 mM $MgCl_2$, 5% gylcerol, 0.5% DTT and 0.5% BSA) in a volume of 20 µl. This solution is mixed with 5 µl of the test compound (100 µM in 20% DMSO), being dispensed by aspirating from a compound source plate. The enzymatic reaction is started by the addition of 5 µl 4 mM ATP. Plates are incubated for 60 min at room temperature and washed 3 times in reaction buffer. Subsequently, Europium-labeled antibodies recognizing the GST protein (Wallac/Perkin Elmer) are added (30 µl of a solution containing 3 µg/ml labeled antibody in PBS containing 0.05% Tween 20). After incubation for 60 min, the plates are washed with PBST and fluorescence is enhanced by addition of DELFIA enhancement solution (Wallac/PerkinElmer). Europium fluorescence is measured in a fluorescence plate reader (i.e. $Victor^2$, Wallac/PerkinElmer) at an excitation wavelength of 340 nm and an emission wavelength of 615 nM. For normalization, each plate contains a column of negative controls with 5 µl 20% DMSO solution instead of test compound. The values of the negative control show the assays maximum signal intensity. Inhibition of GST-ubiquitin transfer to HectH9 leads to a reduced signal. Results are calculated using the following procedure: value of test compound divided by the average of the negative controls on the same plate, multiplied by 100 (=% control). Compounds that give a reduced signal are further evaluated whether they are specific inhibitors of HectH9 activity. Compounds confirmed to be specific are further tested by applying them to a panel of tumor cells and testing them for their anti-proliferative effect.

EXAMPLE 7

Screening Assay in High Throughput Format for Determining the Transfer of Ubiquitin from HectH9 to Myc In a 384 well amylase-coated microtiter plate (Pierce), an enzyme mixture containing 1 ng his-tagged UBAI (E1), 30 ng his-tagged UBCH5 (E2), 50 ng his-tagged HectH9, (all three assay components were obtained as described in Example 6) 50 ng of MBP-tagged c-Myc (the full-length protein obtained by in vitro translation using a kit from Roche) and 100 ng GST-ubiquitin (see Example 6) are mixed in reaction buffer (20 mM Tris/HCl pH 7.5, 150 mM NaCl, 2 mM $MgCl_2$, 5% glycerol, 0.5% DTT and 0.5% BSA) in a volume of 20 µl. This solution is mixed with 5 µl of the test compound (100 µM in 20% DMSO), being dispensed by aspirating from a compound source plate. The enzymatic reaction is started by the addition of an ATP regenerating system (1 mm ATP, 1 µg/µL creatine phosphokinase, 10 mm phosphocreatine). Plates are incubated for 60 min at room temperature and washed 3 times in reaction buffer. Subsequently, Europium-labeled antibodies recognizing the GST protein (Wallac/Perkin Elmer) are added (30 µl of a solution containing 3 µg/ml labeled antibody in PBS containing 0.05% Tween 20). After incubation for 60 min plates are washed with PBST and fluorescence is enhanced by addition of DELFIA enhancement solution (Wallac/PerkinElmer). Europium fluorescence is measured in a fluorescence plate reader (i.e. $Victor^2$, Wallac/PerkinElmer) at an excitation wavelength of 340 nm and an emission wavelength of 615 nM. For normalization, each plate contains a column of negative controls with 5 µl 20% DMSO solution instead of test compound. The values of the negative control show the assays maximum signal intensity. Inhibition of GST-ubiquitin transfer to Myc leads to a reduced signal. Results are calculated using the following procedure: value of test compound divided by the average of the negative controls on the same plate, multiplied by 100 (=% control). Compounds that give a reduced signal are further evaluated whether they are specific inhibitors of HectH9 activity. Compounds confirmed to be specific are further tested by applying them to a panel of tumor cells and testing them for their anti-proliferative effect.

REFERENCES

Berg, T., Cohen, S. B., Desharnais, J., Sonderegger, C., Maslyar, D. J., Goldberg, J., Boger, D. L. and Vogt, P. K. (2002) Small-molecule antagonists of Myc/Max dimerization inhibit Myc-induced transformation of chicken embryo fibroblasts. *Proc Natl Acad Sci USA*, 99, 3830-3835.

Bouchard, C., Dittrich, O., Kiermaier, A., Dohmann, K., Menkel, A., Eilers, M. and Luscher, B. (2001) Regulation of cyclin D2 gene expression by the Myc/Max/Mad network: Myc-dependent TRRAP recruitment and histone acetylation at the cyclin D2 promoter. *Genes Dev*, 15, 2042-2047.

Brodeur, G. M., Seeger, R. C., Schwab, M., Varmus, H. E. and Bishop, J. M. (1984) Amplification of N-myc in untreated human neuroblastomas correlates with advanced disease stage. *Science*, 224, 1121-1124.

Brummelkamp, T. R., Bernards, R. and Agami, R. (2002) A system for stable expression of short interfering RNAs in mammalian cells. *Science*, 296, 550-553.

Desbarats, L., Gaubatz, S. and Eilers, M. (1996) Discrimination between different E-box binding proteins at an endogenous target gene of Myc. *Genes Dev.*, 10, 447-460.

Evan, G. I., Lewis, G. K., Ramsay, G. and Bishop, J. M. (1985) Isolation of monoclonal antibodies specific for human c-myc proto-oncogene product. *Mol. Cell. Biol.*, 5, $3610-361_6$.

Felsher D W & Bishop J M (1999) Mol. Cell 4, 199-207.

Gershkovich, A. A. and Kholodovych, V. V. (1996), J Biochem Biophys Meth 33, 135

Grandori C & Eisenman R N (1997). Trends Biochem Sci. 22, 177-81.

Gu et al. (1994) Mol. Brain Res. 24 (1-4), 77-88

Hatfield P M, Callis J & Vierstra R D (1990) J Biol Chem 265, 15813-7

Hatfield P M & Vierstra R D (1992) Biol Chem 267, 14799-803 He, T. C., Sparks, A. B., Rago, C., Hermeking, H., Zawel, L., da Costa, L. T., Morin, P. J., Vogelstein, B. and Kinzler, K. W. (1998) Identification of c-MYC as a target of the APC pathway. Science, 281, 1509-1512.

Herold, S., Wanzel, M., Beuger, V., Frohme, C., Beul, D., Hillukkala, T., Syvaoja, J., Saluz, H. P., Hänel, F. and Eilers, M. (2002) Negative Regulation of the Mammalian UV Response by Myc through Association with Miz-1. Mol. Cell., 10, 509-521.

Jain, M. et al. (2002) Science 297, 102-4.

Kohl, N. E., Legouy, E., DePinho, R. A., Nisen, P. D., Smith, R. K., Gee, C. E. and Alt, F. W. (1986) Human N-myc is closely related in organization and nucleotide sequence to c-myc. Nature 319 (6048), 73-77

Matayoshi, E. D., Wang G T, Krafft G A, Erickson J. (1990), Science February 23; 247(4945):954-8

Murray, A. (1991) Methods Cell Biol. 36, 581-605

Pelengaris, S. et al., (1999) Mol. Cell 3, 565-77

Pelengaris, S. et al., (2002a) Cell 109, 321-34

Pelengaris, S., Khan, M. & Evan, G., (2002b). Nat Rev Cancer 2, 764-7.

Peukert, K., Staller, P., Schneider, A., Carmichael, G., Hanel, F. and Eilers, M. (1997) An alternative pathway for gene regulation by Myc. Embo J, 16, 5672-568.

Schwab, M., Alitalo, K., Klempnauer, K. H., Varmus, H. E., Bishop, J. M., Gilbert, F., Brodeur, G., Goldstein, M. and Trent, J. (1983) Amplified DNA with limited homology to myc cellular oncogene is shared by human neuroblastoma cell lines and a neuroblastoma tumour. Nature, 305, 245-248.

Selvin, (2000) Nature Structural Biol. 7(9), 730-734

Staller, P., Peukert, K., Kiermaier, A., Seoane, J., Lukas, J., Karsunky, H., Moroy, T., Bartek, J., Massague, J., Hanel, F. and Eilers, M. (2001) Repression of p15INK4b expression by Myc through association with Miz-1. Nat Cell Biol, 3, 392-399.

Sun Y. (2003). Targeting E3 ubiquitin ligases for cancer therapy. Cancer Biology and Therapy, vol. 2, no. 6, 623-629 van de Wetering, M., Sancho, E., Verweij, C., de Lau, W., Oving, I., Hurlstone, A., van der Horn, K., Batlle, E., Coudreuse, D., Haramis, A. P., Tjon-Pon-Fong, M., Moerer, P., van den Born, M., Soete, G., Pals, S., Eilers, M., Medema, R. and Clevers, H. (2002) The beta-catenin/TCF-4 complex imposes a crypt progenitor phenotype on colorectal cancer cells. Cell, 111, 241-250.

Watt, R., Stanton, L. W., Marcu, K. B., Gallo, R. C., Croce, C. M. and Rovera, G. (1983) Nucleotide sequence of cloned cDNA of human c-myc oncogene. Nature 303 (5919), 725-728

Yu, et al., "Identification oa a Novel ubiquitin-conjugating Enzym involved in Mitotic cyclin degradation", Current Biology vol. 6, no. 4, 1 Apr. 1996, pages 455-466, XP002039883

The invention claimed is:

1. A method for identifying a Myc activation inhibitor compound comprising the steps of measuring the ability of a test compound to interfere with the activity of the E3-ligase HectH9, which has the amino acid sequence of SEQ ID NO: 2, wherein HectH9 activity is measured by:
   a) the transfer of ubiquitin from a ubiquitin conjugating enzyme E2 to HectH9, or to a fragment thereof that has E3-ligase activity, or
   b) the transfer of ubiquitin from HectH9 to Myc or a C-terminal fragment thereof that contains a critical site for ubiquitination by HectH9,
   wherein said measurement is conducted after a period of time sufficient to allow for the ubiquitination reaction to occur; and wherein a decrease in the level of said HectH9 activity in the presence of a test compound, as compared to the level of said HectH9 activity in the absence of said test compound, is indicative of said compound's potential to inhibit the activation of Myc.

2. The method of claim 1, wherein Myc is c-Myc.

3. The method of claim 1, for determining whether a test compound has the ability to inhibit transfer of ubiquitin to HectH9, wherein HectH9 or a fragment thereof is incubated together with a ubiquitin activating enzyme (E1), a ubiquitin conjugating enzyme (E2), ubiquitin and ATP for a period of time sufficient to obtain a measurable level of ubiquitin associated with HectH9, and wherein the levels of ubiquitination, of HectH9 in the presence or absence of said test compound are compared, and wherein a decrease in the level of HectH9 ubiquitination in the presence of said test compound, as compared to the level of HectH9 ubiquitination in the absence of said test compound, is indicative of said compound's potential to inhibit the activation of Myc.

4. The method of claim 1, wherein said period of time is about 30 minutes.

5. The method of claim 1 for determining whether a compound has the ability to inhibit the transfer of ubiquitin from HectH9 to its substrate protein Myc, wherein HectH9 or a fragment thereof is incubated together together with a ubiquitin activating enzyme (E1), a ubiquitin conjugating enzyme (E2), ubiquitin, ATP and Myc or a fragment thereof for a period of time sufficient to obtain a measurable level of ubiquitination of Myc, wherein the levels of ubiquitination of Myc in the presence or absence of a test compound are compared and wherein a decrease in the level of Myc ubiquitination in the presence of said test compound, as compared to the level of Myc ubiquitination in the absence of said test compound, is indicative of said compound's potential to inhibit the activation of Myc.

6. The method of of claim 1, wherein the HectH9 fragment used is comprised of a HECT domain.

7. The method of claim 1, wherein said method is performed in a high throughput format.

8. The method of claim 7, wherein said high throughput format is comprised of a step that uses a 96 to 384 well format.

9. The method of claim 1, wherein the HectH9 activity is measured by the transfer of ubiquitin from HectH9 to a C-terminal fragment thereof that is comprised o lysine 298 and/or lysine 355.

* * * * *